US007101895B2

(12) United States Patent
Churcher et al.

(10) Patent No.: US 7,101,895 B2
(45) Date of Patent: Sep. 5, 2006

(54) CYCLOHEXYL SULPHONE DERIVATIVES AS GAMMA-SECRETASE INHIBITORS

(75) Inventors: Ian Churcher, Great Dunmow (GB); Timothy Harrison, Great Dunmow (GB); Sonia Kerrad, Huningue (FR); Paul Joseph Oakley, South Benfleet (GB); Duncan Edward Shaw, Bishops Stortford (GB); Martin Richard Teall, Bishops Stortford (GB); Susannah Williams, Basingstoke (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 184 days.

(21) Appl. No.: 10/679,557

(22) Filed: Oct. 6, 2003

(65) Prior Publication Data

US 2004/0122050 A1     Jun. 24, 2004

(30) Foreign Application Priority Data

Oct. 4, 2002     (GB)     ................................. 0223039.9

(51) Int. Cl.
*A01N 43/40* (2006.01)
*A61K 31/445* (2006.01)

(52) U.S. Cl. ...................... 514/317; 514/424; 514/557; 514/562; 514/602; 514/613; 514/210.01; 514/210; 548/542; 544/124; 544/158

(58) Field of Classification Search ................ 514/317, 514/210.01, 424, 557, 562, 602, 613; 546/216; 548/542; 544/124, 158
See application file for complete search history.

(56) References Cited

U.S. PATENT DOCUMENTS

| 2,802,013 | A | 8/1957 | Dodson | |
|---|---|---|---|---|
| 2,812,330 | A | 11/1957 | Dodson | |
| 2004/0082617 | A1 | 4/2004 | Harrison et al. | |
| 2004/0114496 | A1 | 6/2004 | Sogawa et al. | |
| 2004/0116404 | A1 | 6/2004 | Pineiro et al. | |
| 2004/0121995 | A1* | 6/2004 | Churcher et al. ...... | 514/210.01 |
| 2004/0171683 | A1 | 9/2004 | Pineiro | |
| 2004/0230054 | A1 | 11/2004 | Dinnell et al. | |
| 2005/0075320 | A1 | 4/2005 | Nadin et al. | |

FOREIGN PATENT DOCUMENTS

| CA | 2 473 374 | 7/2003 |
|---|---|---|
| EP | 0863134 | 9/1998 |
| EP | 1 466 898 | 10/2004 |
| JP | 56025149 | 3/1981 |
| JP | 56026847 | 3/1981 |
| JP | 56026866 | 3/1981 |
| WO | WO 00/50391 | 8/2000 |
| WO | WO 01/70677 | 9/2001 |
| WO | WO 02/081433 | 10/2002 |
| WO | WO 02/081435 | 10/2002 |
| WO | WO 03/018543 | 3/2003 |
| WO | WO 03/055850 | 7/2003 |
| WO | WO 03/059335 | 7/2003 |
| WO | WO 2004/013090 | 2/2004 |
| WO | WO 2004/031138 | 4/2004 |
| WO | WO 2004/048321 | 6/2004 |
| WO | WO 2004/101538 | 11/2004 |
| WO | WO 2004/101539 | 11/2004 |
| WO | WO 2005/000798 | 1/2005 |

OTHER PUBLICATIONS

L. Capuano, et al., "Cyclische S-Oxide", Chemische Berichte, vol. 112, pp. 1012-1022 (1979).
J.M. Decesare, et al.:, "Gamma- and Beta-epoxy sulfones. Formation of different ring-sized products upon reaction with CH3MgI or LiN[CH(CH$_3$)$_2$]$_2$", Canadian Journal of Chemistry., vol. 59, pp. 1415-1424 (1981).
O. Eisleb, "Neue Synthesen mittels Natriumamids", Berichte der Deutschen Chemischen Gesellschaft, vol. 74, pp. 1433-1450 (1978).
J. Golinski, et al., "Reactions of Organic Anions; XVIV. Catalytic Two-Phase Alkylations of Benzyl Sulfones and Sulfonamides", SYNTHESIS, No. 6, pp. 461-463 (1979).
P. Kisanga, et al., "Development, Synthetic Scope, and Mechanistic Studies of the Palladium-Catalyzed Cycloisomerization of Functionalized 1,6-Dienes in the Presence of Silane", Journal of the American Chemical Society, vol. 122, No. 41, pp. 10017-10026 (2000).
C. Koradin, et al., "Cesium Catalyzed Addition of Nitriles to Alkynes", SYNLETT, No. 10, pp. 1452-1454 (2000).

(Continued)

*Primary Examiner*—Johann Richter
*Assistant Examiner*—Chukwuma Nwaonicha
(74) *Attorney, Agent, or Firm*—John C. Todaro; Melvin Winokur

(57) ABSTRACT

Compounds of formula I:

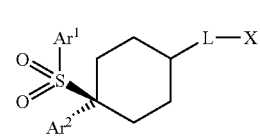

wherein $Ar^1$ and $Ar^2$ are optionally substituted aryl or heteroaryl, L is a bond, =CH— or —(CHR$^a$)$_n$—, and X is SCN, SR$^1$, S(O)R$^1$, (CR$^a$R$^b$)$_m$SO$_2$R$^1$, SO$_2$N(R$^2$)$_2$, SO$_2$NHCOR$^1$, SO$_2$NHN(R$^2$)$_2$, OSO$_2$N(R$^2$)$_2$, OS(O)N(R$^2$)$_2$, OSO$_2$NHCOR$^1$, COR$^4$, NHCOR$^1$, NHCO$_2$R$^1$, NHCON(R$^2$)$_2$, NHSO$_2$R$^1$ or NHSO$_2$N(R$^2$)$_2$, inhibit the processing of APP by gamma secretase, and hence are useful in treatment of Alzheimer's disease.

8 Claims, No Drawings

OTHER PUBLICATIONS

T. Oyuyama, et al., "Flash Photolytic Generation of a Dithio Carbocation from 1,3-Dithiolance Derivatives and Its Reaction with Nucleophiles", Bulletin of the Chemical Society of Japan, vol. 64, No. 9, pp. 2751-2756 (1991).

M. Makosza, et al., "Ambiphilic Reactivity of 2,4-Djnitrobenzyl p-Tolyl Sulfone Carbanion", Polish Journal of Chemistry, vol. 72, pp. 1198-1201 (1998).

R. K. Norris, et al., "The Stereochemistry of the $S_{RN}1$ Reaction In Some Cyclohexane Derivatives", TETRAHEDRON, vol. 38, No. 8, pp. 1051-1057 (1982).

J. P. Scott et al., "Expedient Diels-Alder assembly of 4-aryl-4-phenylsulfonyl cyclohexanones", Tetrahedron Letters, vol. 45, pp. 3345-3348 (2004).

E. W. Garbisch et al., "On the Mechanism of Benzylic Substituent Hydrogenolysis", Journal of the American Chemical Society, vol. 89(16), pp. 4233-4235 (1967).

R. K. Norris et al., "An Example of Substitution proceeding with Retention in the SRN1 Reaction. Trapping of a Pyramidal Benzylic Radical by Benzenethiolate Ion", J. of the Chem. Soc. Chem. Comm., Issue 3, pp. 79-80 (1981).

* cited by examiner

CYCLOHEXYL SULPHONE DERIVATIVES AS GAMMA-SECRETASE INHIBITORS

CROSS-REFERENCE TO RELATED APPLICATIONS

This application claims priority under 35 U.S.C. § 119 from Great Britain Application No. 0223039.9, filed Oct. 4, 2002.

The present invention relates to a novel class of compounds, their salts, pharmaceutical compositions comprising them, processes for making them and their use in therapy of the human body. In particular, the invention relates to novel cyclohexyl sulphones which inhibit the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are relatively few reports in the literature of compounds with inhibitory activity towards γ-secretase, as measured in cell-based assays. These are reviewed in WO 01/70677. Many of the relevant compounds are peptides or peptide derivatives.

WO 00/50391 discloses a broad class of sulphonamides as modulators of the production of β-amyloid, but neither discloses nor suggests the compounds of the present invention.

The present invention provides a novel class of cyclohexyl sulphones which are useful in the treatment or prevention of AD by inhibiting the processing of APP by the putative γ-secretase, thus arresting the production of Aβ.

According to the invention, there is provided a compound of formula I:

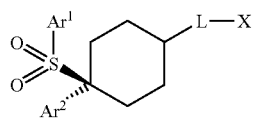

wherein

X represents SCN, $SR^1$, $S(O)R^1$, $(CR^aR^b)_mSO_2R_1$, $SO_2N(R^2)_2$, $SO_2NHCOR^1$, $SO_2NHN(R^2)_2$, $OSO_2N(R^2)_2$, $OS(O)N(R^2)_2$, $OSO_2NHCOR^1$, $COR^4$, $NHCOR^1$, $NHCO_2R^1$, $NHCON(R^2)_2$, $NHSO_2R^1$ or $NHSO_2N(R^2)_2$;

m is 0 or 1

$R^a$ represents H or $C_{1-4}$alkyl;

$R^b$ represents H, $C_{1-4}$alkyl, $CO_2H$, $C_{1-4}$alkoxycarbonyl or $C_{1-4}$alkylsulphonyl; or $R^b$ may combine with $R^1$ to form a 5- or 6-membered ring;

L represents a bond, =CH— or —(CHR$^a$)$_n$—; with the proviso that L does not represent a bond when X represents $NHCOR^1$, $NHCO_2R^1$ or $NHSO_2R^1$; and with the proviso that if L represents =CH—, X represents $SO_2R^1$ or $COR^4$;

n is 1, 2 or 3;

$R^1$ represents $CF_3$ or $C_{1-6}$alkyl, $C_{2-6}$alkenyl, $C_{3-9}$cycloalkyl or $C_{3-6}$cycloalkylC$_{1-6}$alkyl, any of which may bear up to 2 substituents selected from halogen, CN, $CF_3$, $OR^3$, $COR^3$, $CO_2R^3$, $OCOR^{3a}SO_2R^{3a}$, $N(R^5)_2$, and $CON(R^5)_2$, or $R^1$ represents aryl, arylC$_{1-6}$alkyl, C-heterocyclyl or C-heterocyclylC$_{1-6}$alkyl;

or $R^1$ may combine with $R^b$ to form a 5- or 6-membered ring;

each $R^2$ independently represents H, $C_{1-6}$alkoxy, or $C_{1-6}$alkyl, $C_{2-6}$alkenyl, $C_{3-9}$cycloalkyl or $C_{3-6}$cycloalkylC$_{1-6}$alkyl, any of which may bear up to 2 substituents selected from halogen, CN, $CF_3$, $OR^3$, $COR^3$, $CO_2R^3$, $OCOR^{3a}$, and $CON(R^5)_2$; or aryl, arylC$_{1-6}$alkyl, C-heterocyclyl or C-heterocyclylC$_{1-6}$alkyl;

or two $R^2$ groups together with a nitrogen atom to which they are mutually attached complete an N-heterocyclyl group;

$R^3$ represents H, $C_{1-4}$alkyl, phenyl or heteroaryl;

$R^{3a}$ represents $C_{1-4}$alkyl, phenyl or heteroaryl;

$R^4$ represents $(CR^aR^b)SO_2R^1$, pyridine N-oxide, or phenyl or heteroaryl which bear a substituent selected from $CO_2H$, methylenedioxy, difluoromethylenedioxy, $COR^3$, C-heterocyclyl, $C_{1-4}$alkylsulphonyl and substituted $C_{1-6}$alkyl, $C_{1-6}$alkoxy, $C_{2-6}$alkenyl or $C_{2-6}$alkenyloxy wherein the substituent is selected from halogen, CN, $CF_3$, $OR^3$, $CO_2R^3$, $OCOR^{3a}$, $N(R^5)_2$ and $CON(R^5)_2$;

$R^5$ represents H or $C_{1-4}$alkyl, or two $R^5$ groups together with a nitrogen atom to which they are mutually attached complete an azetidine, pyrrolidine, piperidine, morpholine, thiomorpholine or thiomorpholine-1,1-dioxide ring;

$Ar^1$ and $Ar^2$ independently represent phenyl or heteroaryl, either of which bears 0–3 substituents independently selected from halogen, CN, $NO_2$, $CF_3$, $CHF_2$, OH, $OCF_3$, CHO, CH=NOH, $C_{1-4}$alkoxy, $C_{1-4}$alkoxycarbonyl, $C_{2-6}$acyl, $C_{2-6}$alkenyl and $C_{1-4}$alkyl which optionally bears a substituent selected from halogen, CN, $NO_2$, $CF_3$, OH and $C_{1-4}$alkoxy;

"aryl" at every occurrence thereof refers to phenyl or heteroaryl which optionally bear up to 3 substituents selected from halogen, CN, $NO_2$, $CF_3$, $OCF_3$, $OR^3$, $COR^3$, $CO_2R^3$, $OCOR^{3a}$, $N(R^5)_2$, $CON(R^5)_2$ and optionally-substituted $C_{1-6}$alkyl, $C_{1-6}$alkoxy, $C_{2-6}$alkenyl or $C_{2-6}$alkenyloxy wherein the substituent is selected from halogen, CN, $CF_3$, phenyl, $OR^3$, $CO_2R^3$, $OCOR^{3a}$, $N(R^5)_2$ and $CON(R^5)_2$; and "C-heterocyclyl" and "N-heterocyclyl" at every occurrence thereof refer respectively to a heterocyclic ring system bonded through carbon or nitrogen, said ring system being non-aromatic and comprising up to 10 atoms, at least one of which is O, N or S, and optionally bearing up to 3 substituents selected from oxo, halogen, CN, $NO_2$, $CF_3$, $OCF_3$, $OR^3$, $COR^3$, $CO_2R^3$, $OCOR^{3a}$, $OSO_2R^{3a}$, $N(R^5)_2$, $CON(R^5)_2$ and optionally-substituted phenyl, $C_{1-6}$alkyl, $C_{1-6}$alkoxy, $C_{2-6}$alkenyl or $C_{2-6}$alkenyloxy wherein the substituent is selected from halogen, CN, $CF_3$, $OR^3$, $CO_2R^3$, $OCOR^{3a}$, $N(R_5)_2$ and $CON(R^5)_2$;

or a pharmaceutically acceptable salt thereof.

Where a variable occurs more than once in formula I, the individual occurrences are independent of each other, unless otherwise indicated.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expression "$C_{3-9}$cycloalkyl" as used herein refers to nonaromatic monocyclic or fused bicyclic hydrocarbon ring systems comprising from 3 to 9 ring atoms. Examples include cyclopropyl, cyclobutyl, cyclopentyl, cyclohexyl, cyclohexenyl and bicyclo[2.2.1]heptyl. Monocyclic systems of 3 to 6 members are preferred.

The expression "$C_{3-6}$cycloalkyl$C_{1-6}$alkyl" as used herein includes cyclopropylmethyl, cyclobutylmethyl, cyclopentylmethyl and cyclohexylmethyl.

The expression "$C_{2-6}$acyl" as used herein refers to $C_{1-5}$alkylcarbonyl groups in which the alkyl portion may be straight chain, branched or cyclic, and may be halogenated. Examples include acetyl, propionyl and trifluoroacetyl.

The expression "heterocyclyl" as defined herein includes both monocyclic and fused bicyclic systems of up to 10 ring atoms selected from C, N, O and S. Mono- or bicyclic systems of up to 7 ring atoms are preferred, and monocyclic systems of 4, 5 or 6 ring atoms are most preferred. Examples of heterocyclic ring systems include azetidinyl, pyrrolidinyl, 3-pyrrolinyl, terahydrofuryl, 1,3-dioxolanyl, tetrahydrothiophenyl, tetrahydropyridinyl, piperidinyl, piperazinyl, morpholinyl, thiomorpholinyl, imidazolidinyl, oxazolidinyl, thiazolidinyl, 2,5-diazabicyclo[2.2.1]heptyl, 2-aza-5-oxabicyclo[2.2.1]heptyl and 1,4-dioxa-8-azaspiro[4.5]decanyl. Unless otherwise indicated, heterocyclyl groups may be bonded through a ring carbon atom or a ring nitrogen atom where present. "C-heterocyclyl" indicates bonding through carbon, while "N-heterocyclyl" indicates bonding through nitrogen.

The expression "heteroaryl" as used herein means a monocyclic system of 5 or 6 ring atoms, or fused bicyclic system of up to 10 ring atoms, selected from C, N, O and S, wherein at least one of the constituent rings is aromatic and comprises at least one ring atom which is other than carbon. Monocyclic systems of 5 or 6 members are preferred. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine. Pyridine rings may be in the N-oxide form.

Where a phenyl group or heteroaryl group bears more than one substituent, preferably not more than one of said substituents is other than halogen or alkyl.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, benzenesulphonic acid, methanesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, X represents SCN, $SR^1$, $S(O)R^1$, $(CR^aR^b)_mSO_2R^1$, $SO_2N(R^2)_2$, $SO_2NHCOR^1$, $SO_2NHN(R^2)_2$, $OSO_2N(R^2)_2$, $OS(O)N(R^2)_2$, $OSO_2NHCOR^1$, $COR^4$, $NHCOR^1$, $NHCO_2R^1$, $NHCO_2N(R^2)_2$, $NHSO_2R^1$ or $NHSO_2N(R^2)_2$. In a preferred embodiment, X is selected from $SR^1$, $(CR^aR^b)_mSO_2R^1$, $SO_2N(R^2)_2$, $OSO_2N(R^2)_2$, $COR^4$, $NHCOR^1$, $NHCO_2R^1$, $NHCON(R^2)_2$, $NHSO_2R^1$ and $NHSO_2N(R^2)_2$.

When X represents $(CR^aR^b)_mSO_2R^1$, m is 0 or 1. In one embodiment, m is 0. In an alternative embodiment, m is 1.

When m is 1, $R^a$ represents H or $C_{1-4}$alkyl such as methyl, ethyl or propyl. When m is 1, $R^b$ represents H, $C_{1-4}$alkyl (such as methyl, ethyl or propyl), $CO_2H$, $C_{1-4}$alkoxycarbonyl (such as $CO_2Me$ or $CO_2Et$) or $C_{1-4}$alkylsulphonyl (such as methanesulphonyl); or $R^b$ may combine with $R^1$ to form a 5- or 6-membered ring, in particular a tetrahydrothiophene-1,1-dioxide ring or a tetrahydrothiopyran-1,1-dioxide ring.

When m is 1, preferred identities for the moiety —$CR^aR^b$— include:

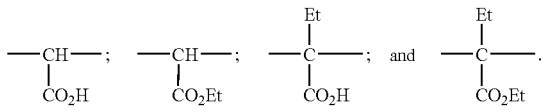

L represents a bond, =CH— or —$(CHR^a)_n$—; but when L represents a bond, X cannot represent $NHCOR^1$, $NHCO_2R^1$ or $NHSO_2R^1$; and when L represents =CH—, X must represent $SO_2R^1$ or $COR^4$.

When L represents a bond or —$(CHR^a)_n$—, the moiety -L-X is preferably in the cis stereoconfiguration relative to the $Ar^1SO_2$ moiety.

When L represents —$(CHR^a)_n$—, n is 1, 2 or 3 (preferably 1 or 2), and each $R^a$ is independently H or $C_{1-4}$alkyl such as methyl or ethyl (especially methyl), but L preferably comprises not more than one $R^a$ group that is other than H.

Particularly preferred examples of L include a bond, —$CH_2$— and —$CH_2CH_2$—.

$R^1$ is preferably $CF_3$, aryl or arylalkyl, or an alkyl, cycloalkyl or cycloalkylalkyl group, optionally substituted as described previously. Preferred substituents include halogen (especially fluorine or chlorine), $CF_3$, CN, $OR^3$ (especially OH, OMe and OEt), $COR^3$ (especially acetyl), $CO_2R^3$ (especially $CO_2H$, $CO_2Me$ and $CO_2Et$) and $CON(R^5)_2$ (especially $CONH_2$).

Examples of alkyl groups represented by $R^1$ include methyl, ethyl, n-propyl, isopropyl, t-butyl, isobutyl, 2,2,2-trifluoroethyl, cyanomethyl, 2-hydroxyethyl, 2-methoxyethyl, 2-hydroxy-2-methylpropyl, carboxymethyl, ethoxycarbonylmethyl, 1-carboxyethyl, 1-ethoxycarbonylethyl, carbamoylmethyl and $MeCOCH_2$—.

Examples of cycloalkyl and cycloalkylalkyl groups represented by $R^1$ include cyclopropyl, cyclobutyl, cyclopentyl, cyclohexyl, cyclopropylmethyl and cyclopentylmethyl.

When $R^1$ represents aryl or arylalkyl, the aryl group may be phenyl or heteroaryl, optionally substituted as defined previously. Preferred substituents include halogen (especially chlorine or fluorine), $CF_3$, $OCF_3$, alkyl (especially methyl), OH and alkoxy (especially methoxy). Preferred heteroaryl groups include pyridine, pyrimidine, furan, thiophene, thiazole, imidazole, triazole, thiadiazole and tetrazole.

Examples of aryl groups represented by $R^1$ include phenyl, 2-fluorophenyl, 4-fluorophenyl, 2,4-difluorophenyl, 2-chlorophenyl, 2-, 3- and 4-hydroxyphenyl, 2-trifluoromethoxyphenyl, 2-methoxyphenyl, 2-pyridyl (and the corresponding N-oxide), 4-pyridyl, 2-pyrimidinyl, 2-furyl, 2-thienyl, 2-thiazolyl, 2-imidazolyl, 2-methylfuran-3-yl, 4-methylthiazol-3-yl, 5-methyl-1,3,4-thiadiazol-2-yl, 1-methylimidazol-2-yl, 1-methyl-1,2,3,4-tetrazol-5-yl, 1,2,4-triazol-3-yl, 1-methyl-1,2,4-triazol-3-yl, 2-methyl-1,2,4-triazol-3-yl and 4-methyl-1,2,4-triazol-3-yl.

Arylalkyl groups represented by $R^1$ are typically optionally substituted benzyl, phenethyl, heteroarylmethyl or heteroarylethyl groups. Examples include benzyl, 2-furylmethyl, 2-thienylmethyl and 1-(2-thienyl)ethyl.

When X represents $SO_2NHCOR^1$ or $OSO_2NHCOR^1$, $R^1$ is very aptly $CF_3$, $C_{1-6}$alkyl or $C_{3-6}$cycloalkyl, for example methyl.

When X represents $S(O)R^1$, $R^1$ very aptly represents aryl, for example 2-pyridyl or 1-methyl-1,2,3,4-tetrazol-5-yl.

When X represents $NHCO_2R^1$, $R^1$ very aptly represents $C_{1-6}$alkyl (for example methyl) or arylalkyl (for example benzyl).

When X represents $NHCOR^1$, $R^1$ very aptly represents $C_{1-6}$alkyl (for example methyl) or substituted $C_{1-6}$alkyl (for example 2,2,2-trifluoroethyl or 1-hydroxy-2,2,2-trifluoroethyl).

For any $N(R^2)_2$ fragment, preferably either at least one of the $R^2$ groups represents H or $C_{1-6}$alkyl such as methyl, or the two $R^2$ groups complete an N-heterocyclyl group. When one $R^2$ group represents $C_{1-6}$alkoxy (such as methoxy), the other preferably represents $C_{1-6}$alkyl (such as methyl).

When $N(R^2)_2$ does not represent N-heterocyclyl, preferably one $R^2$ is H or methyl and the other is H, methoxy, aryl (such as phenyl) or optionally substituted alkyl or cycloalkyl. Preferred substituents include $CF_3$, $OR^3$ (such as OH and OMe), $CO_2R^3$ (such as t-butoxycarbonyl) and $OCOR^{3a}$ (such as acetoxy). Within this embodiment, preferred identities for $N(R^2)_2$ include $NH_2$, NHMe, NHEt, $NH^iPr$, $NH^tBu$, $NMe_2$, N(Me)OMe, NHPh, NH-cyclobutyl, $NHCH_2CF_3$, $NHCH_2CO_2{}^tBu$, $NHCH_2CH_2OCOMe$ and $NHCH_2CH_2OH$.

When $N(R^2)_2$ represents N-heterocyclyl, the heterocyclic ring is typically an optionally substituted azetidine, pyrrolidine, 3-pyrroline, piperidine, morpholine, thiomorpholine or 2-aza-5-oxabicyclo[2.2.1]heptane ring. Azetidine and pyrrolidine are preferred, and azetidine is particularly preferred. Preferred substituents include oxo, halogen (especially fluorine), $CF_3$, $OR^3$ (especially OH), $OCOR^{3a}$ (especially acetoxy and trimethylacetoxy), $OSO_2R^{3a}$ (especially methanesulphonyloxy), $CO_2R^3$ (especially $CO_2H$ and $CO_2Me$), $N(R^5)_2$ (especially dimethylamino) and alkyl (especially methyl). Examples of preferred N-heterocyclyl groups include azetidin-1-yl, pyrrolidin-1-yl, 3-pyrrolin-1-yl, piperidin-1-yl, morpholin-4-yl, thiomorpholin-4-yl, 2-aza-5-oxabicyclo[2.2.1]hept-2-yl, 3-oxo-azetidin-1-yl, 3-hydroxyazetidin-1-yl, 3-acetoxyazetidin-1-yl, 3-(dimethylamino)azetidin-1-yl, 3-methanesulphonyloxyazetidin-1-yl, 3,3-difluoroazetidin-1-yl, 3-hydroxy-3-methylazetidin-1-yl, 2-carboxypyrrolidin-1-yl, 2-methoxycarbonylpyrrolidin-1-yl, 3-fluoropyrrolidin-1-yl, 3,3-difluoropyrrolidin-1-yl, 2-(trifluoromethyl)pyrrolidin-1-yl, 3-oxo-pyrrolidin-1-yl, 3-hydroxypyrrolidin-1-yl, 3-hydroxy-3-methylpyrrolidin-1-yl, 3-(trimethylacetoxy)pyrrolidin-1-yl, 4-(trifluoromethyl)piperidin-1-yl and 4,4-difluoropiperidin-1-yl.

When X represents $SO_2NHN(R^2)_2$, $OS(O)N(R^2)_2$ or $NHCON(R^2)_2$, very aptly both $R^2$ groups represent methyl, or one $R^2$ represents H and the other represents $C_{1-6}$alkyl, such as methyl or ethyl.

In the embodiments in which X represents $COR^4$, $R^4$ is selected from $(CR^aR^b)SO_2R^1$, pyridine N-oxide, or phenyl or heteroaryl which is substituted as defined previously.

When $R^4$ represents $(CR^aR^b)SO_2R^1$, $R^a$ and $R^b$ preferably independently represent H or $C_{1-4}$alkyl, or $R^b$ together with $R^1$ completes a 5- or 6-membered ring. Suitable rings include tetrahydrothiophene-1,1,-dioxide and tetrahydrothiopyran-1,1-dioxide. Tetrahydrothiophene-1,1,-dioxide is preferred. In this context, $R^1$ is very aptly optionally-substituted $C_{1-6}$alkyl, especially methyl, or else completes a ring with $R^b$. Examples of preferred groups represented by $R^4$ in this embodiment include $CH_2SO_2Me$, $CH(Me)SO_2Me$, $C(Me)_2SO_2Me$ and 1,1-dioxo-tetrahydrothiophen-2-yl.

When $R^4$ represents pyridine N-oxide, the pyridine ring may be bonded through the 2-, 3- or 4-position, but the 2-position is preferred.

$R^4$ may alternatively represent phenyl or heteroaryl, either of which must bear a substituent selected from $CO_2H$, methylenedioxy, difluoromethylenedioxy, $COR^3$, C-heterocyclyl, $C_{1-4}$alkylsulphonyl and substituted $C_{1-6}$alkyl, $C_{1-6}$alkoxy, $C_{2-6}$alkenyl or $C_{2-6}$alkenyloxy wherein the substituent is selected from halogen, CN, $CF_3$, $OR_1$, $CO_2R^3$, $OCOR^{3a}$, $N(R^5)_2$ and $CON(R^5)_2$. In this context, preferred heteroaryl groups are 5-membered, such as furan, pyrrole and thiophene, furan and pyrrole being particularly preferred and furan most preferred. Examples of preferred substituents include $CO_2H$, difluoromethylenedioxy, formyl, 1,3-dioxolan-2-yl, methanesulphonyl, hydroxymethyl, allyl, allyloxy, —$(CH_2)_x$—$CO_2R^3$, —$O(CH_2)_y$—$CO_2R^3$, —CH=CH—$CO_2R^3$, —$(CH_2)_x$—$N(R^5)_2$ and —$O(CH_2)_y$—$N(R^5)_2$, where x is 1, 2 or 3 and y is 2 or 3. In this context $R^3$ is very aptly H, methyl or ethyl, and $N(R^5)_2$ is very aptly morpholin-4-yl or 1,1-dioxo-thiomorpholin-4-yl.

$Ar^1$ and $Ar^2$ independently represent optionally substituted phenyl or heteroaryl. $Ar^1$ is preferably selected from optionally substituted phenyl and optionally substituted 6-membered heteroaryl. Preferred 6-membered heteroaryl embodiments of $Ar^1$ include optionally substituted pyridyl, in particular optionally substituted 3-pyridyl. $Ar^1$ is preferably selected from 6-(trifluoromethyl)-3-pyridyl and phenyl which is optionally substituted in the 4-position with halogen, CN, vinyl, allyl, acetyl, methyl or mono-, di- or trifluoromethyl. In one preferred embodiment of the invention $Ar^1$ represents 4-chlorophenyl. In another preferred embodiment $Ar^1$ represents 4-trifluoromethylphenyl. In a further preferred embodiment $A^1$ represents 6-(trifluoromethyl)-3-pyridyl.

$Ar^2$ preferably represents optionally substituted phenyl, in particular phenyl bearing 2 or 3 substituents selected from halogen, CN, $CF_3$ and optionally-substituted alkyl. $Ar^2$ is typically selected from phenyl groups bearing halogen substituents (preferably fluorine) in the 2- and 5-positions or in the 2-, 3- and 6-positions, or from phenyl groups bearing a fluorine substituent in the 2-position and halogen, CN, methyl or hydroxymethyl in the 5-position. In a preferred embodiment of the invention, Ar represents 2,5-difluorophenyl.

In a particular embodiment, $Ar^1$ is 4-chlorophenyl or 4-trifluoromethylphenyl or 6-(trifluoromethyl)-3-pyridyl and $Ar^2$ is 2,5-difluorophenyl.

A subclass of the compounds of the invention comprises the compounds of formula II:

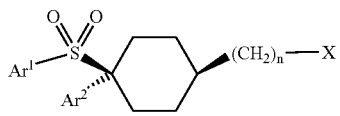

II wherein n, X, $Ar^1$ and $Ar^2$ have the same definitions and preferred identities as before;

and pharmaceutically acceptable salts thereof.

Preferably n is 1 or 2.

In a subset of the compounds of formula II, X is selected from $NHCOR^1$, $NHCO_2R^1$ and $NHSO_2R^1$ where $R^1$ has the same definition and preferred identities as before.

A second sub-class of the compounds of the invention comprises the compounds of formula III:

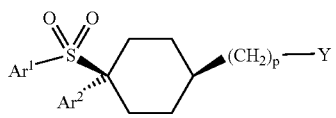

III wherein p is 0, 1, 2 or 3;

Y is SCN, $SR^1$, $S(O)R^1$, $(CR^aR^b)_mSO_2R^1$, $SO_2N(R^2)_2$, $SO_2NHCOR^1$, $SO_2NHN(R^2)_2$, $OSO_2N(R^2)_2$, $OS(O)N(R^2)_2$, $OSO_2NHCOR^1$, $COR^4$, $NHCON(R^2)_2$ or $NHSO_2N(R^2)_2$;

and m, $R^a$, $R^b$, $R^1$, $R^2$, $R^4$, $Ar^1$ and $Ar^2$ have the same definitions and preferred identities as before;

and pharmaceutically acceptable salts thereof.

Preferably p is 0, 1 or 2.

In a subset of the compounds of formula III, Y is selected from SCN, $SR^1$, $S(O)R^1$, $(CR^aR^b)_mSO_2R_1$, $SO_2N(R^2)_2$, $SO^2NHCOR^1$ and $SO_2NHN(R^2)_2$; preferably from SCN, $SR^1$, $(CR^aR^b)_mSO_2R_1$ and $SO_2N(R^2)_2$; and most preferably from $(CR^aR^b)_mSO_2R^1$ and $SO_2N(R^2)_2$. Within this subset, p is preferably 1 or 2. In one preferred embodiment Y is $(CR^aR^b)_mSO_2R^1$. In another preferred embodiment Y is $SO_2N(R^2)_2$, in which case p is very aptly 1 and $N(R^2)_2$ is very aptly N-heterocyclyl.

In a second subset of the compounds of formula III, Y is selected from $OSO_2N(R^2)_2$, $OS(O)N(R^2)_2$, $OSO_2NHCOR^1$, $NHCON(R^2)_2$, $NHSO_2N(R^2)_2$ and $COR^4$. Within this subset, p is preferably 0 or 1. In one preferred embodiment p is 0 and Y is $OSO_2N(R^2)_2$. In another preferred embodiment, p is 1 and Y is $NHCON(R^2)_2$. In a further preferred embodiment, p is 1 and Y is $COR^4$. In a further preferred embodiment, p is 0 and Y is $NHSO_2N(R^2)_2$. In a further preferred embodiment, p is 1 and Y is $NHSO_2N(R^2)_2$.

A third sub-class of the compounds of the invention comprises the compounds of formula IV:

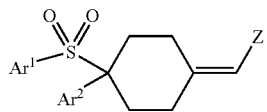

IV wherein Z represents $SO_2R^1$ or $COR^4$;

and $R^1$, $R^4$, $Ar^1$ and $Ar^2$ have the same definitions and preferred identities as before;

and pharmaceutically acceptable salts thereof.

In a preferred embodiment, Z is $SO_2R^1$.

Examples of individual compounds in accordance with the invention are provided in the Examples section appended hereto.

The compounds of formula I have an activity as modulators of the processing of APP by γ-secretase.

The invention also provides pharmaceutical compositions comprising one or more compounds of formula I or the pharmaceutically acceptable salts thereof and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 250 mg, for example 1, 2, 5, 10, 25, 50, 100, 200 or 250 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β3-amyloid deposition such as Alzheimer's disease.

The present invention further provides the use of a compound of formula I or a pharmaceutically acceptable salt thereof in the manufacture of a medicament for treating or preventing Alzheimer's disease.

The present invention further provides a method of treatment of a subject suffering from or prone to a condition associated with the deposition of β-amyloid which comprises administering to that subject an effective amount of a compound according to formula I or a pharmaceutically acceptable salt thereof. Preferably the condition is a neurological disease having associated β-amyloid deposition such as Alzheimer's disease.

For treating or preventing Alzheimer's Disease, a suitable dosage level is about 0.01 to 250 mg/Kg per day, preferably about 0.10 to 100 mg/Kg per day, especially about 1.0 to 50 mg/Kg, and for example about 10 to 30 mg/Kg of body weight per day. Thus, a dose of about 500 mg per person per day may be considered. The compounds may be administered on a regimen of 1 to 4 times per day. In some cases, however, dosage outside these limits may be used.

Compounds of formula I in which L is —$(CH_2)_p$— and X represents SCN, $SR^1$ or $(CR^aR^b)_mSO_2R^1$ may be prepared by reaction of, respectively, MSCN, $MSR^1$ or $M(CR^aR^b)_mSO_2R^1$ with a compound of formula (1):

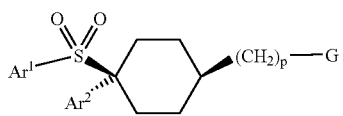

(1)

where M is a metal cation (preferably an alkali metal cation, such as Li or Na), G is a leaving group, and $R^1$, $R^a$, $R^b$, $Ar^1$, $Ar^2$, m and p have the same meanings as before. Suitable identities for G include halide (especially bromide or iodide) and alkyl- or arylsulphonate. Iodide and mesylate are particularly suitable. The metallated derivatives $MSR^1$ and $M(CR^aR^b)_mSO_2R^1$ may be generated by reaction of the corresponding hydrides with NaOH, LiOH, NaH, BuLi, LiN(iPr)$_2$ or similar, and are typically reacted in situ with the compounds (1).

Compounds of formula I in which X represents $S(O)R^1$ may be prepared from the corresponding compounds in which X represents $SR^1$ by oxidation with one equivalent of m-chloroperoxybenzoic acid. The oxidation takes place at ambient temperature in a dichloromethane-water mixture. Oxidation of the same compounds with two equivalents of m-chloroperoxybenzoic acid, or with sodium periodate in the presence of $RuO_2$ catalyst, provides an alternative route to compounds in which X represents $(CR^aR^b)_mSO_2R^1$ and m is 0.

Compounds of formula I in which L is —$(CH_2)_p$— and X represents, $SO_2N(R^2)_2$ or $SO_2NHN(R^2)_2$ may be prepared by reaction of $(R^2)_2NH$ or $(R^2)_2NNH_2$ respectively with a sulphonyl chloride of formula (2):

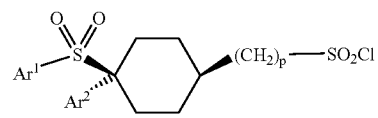

(2)

where $R^2$, $Ar^1$, $Ar^2$ and p have the same meanings as before. The reaction is typically carried out in dichloromethane at ambient temperature, either using excess of the amine or using an additional base such as potassium carbonate, pyridine or triethylamine.

Compounds of formula I in which X represents $SO_2NHCOR^1$ may be prepared from the corresponding compounds in which X represents $SO_2NH_2$ by coupling with $R^1CO_2H$. Any of the standard peptide coupling procedures may be used, for example the use of dimethylaminopyridine and 1-(3-dimethylaminopropyl)-3-ethylcarbodiimide.

Compounds of formula I in which L is —$(CH_2)_p$— and X represents $OSO_2N(R^2)_2$ may be prepared by reaction of a sulphamoyl chloride $(R^2)_2NSO_2Cl$ with an alcohol of formula (3):

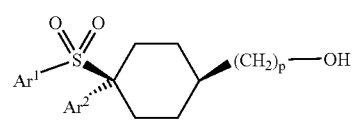

(3)

where $R^2$, $Ar^1$, $Ar^2$ and p have the same meanings as before. The reaction is typically carried out in dichloromethane at ambient temperature in the presence of a base such as pyridine or triethylamine. The sulphamoyl chlorides $(R^2)_2NSO_2Cl$ are available by reaction of $(R^2)_2NH$ with sulphuryl chloride in acetonitrile at ambient temperature.

Compounds of formula I in which X represents $OSO_2NHCOR^1$ may be prepared from the corresponding compounds in which X represents $OSO_2NH_2$ by coupling with $R^1CO_2H$. Any of the standard peptide coupling procedures may be used, for example the use of dimethylaminopyridine and 1-(3-dimethylaminopropyl)-3-ethylcarbodiimide.

Compounds of formula I in which L is —$(CH_2)_p$— and X represents $OS(O)N(R^2)_2$ may be prepared by treating an alcohol of formula (3) first with thionyl chloride, and then with $(R^2)_2NH$. The reaction with thionyl chloride is typically carried out at −78° C., and the resulting intermediate reacted in situ with the amine at the same temperature, then allowed to warm to ambient temperature.

Compounds of formula I in which L is —$(CH_2)_p$— and X represents $NHCOR^1$, $NHCO_2R^1$, $NHSO_2R^1$ or $NHSO_2N(R^2)_2$ may be prepared by reacting an amine of formula (4) with, respectively, $R^1COCl$, $R^1OCOCl$, $R^1SO_2Cl$ and $(R^2)_2NSO_2Cl$:

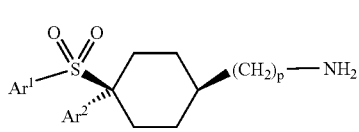

(4)

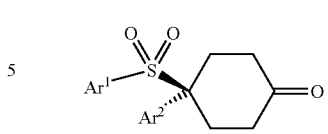

(7)

where $R^1$, $Ar^1$, $Ar^2$ and p have the same meanings as before. The reaction is typically carried out in dichloromethane at ambient or reduced temperature, in the presence of a base such as pyridine or triethylamine. Alternatively, the compounds in which X represents $NHCOR^1$ may be prepared by coupling of amines (4) with $R^1CO_2H$. Any of the standard peptide coupling procedures may be used, for example the use of 1-hydroxybenzotriazole or dimethylaminopyridine and 1-(3-dimethylaminopropyl)-3-ethylcarbodiimide.

An alternative route to the compounds of formula I in which L is $—(CH_2)_p—$ and X represents $NHSO_2N(R^2)_2$ involves reacting an amine of formula (4) with catechol sulphate and reacting the resulting sulphamate with $(R^2)_2NH$. The first step is typically carried out in THF at 0° C., and the second step at 80° C. in dioxan.

Compounds of formula I in which L is $—(CH_2)_p—$ and X represents $NHCON(R^2)_2$ may be prepared by treating an carboxylic acid of formula (5) first with diphenylphosphoryl azide, and then with $(R^2)_2NH$:

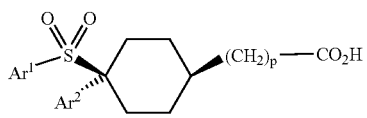

(5)

where $R^2$, $Ar^1$, $Ar^2$ and p have the same meanings as before. The first step is typically carried out in toluene at 110° C. in the presence of triethylamine, and the second step at ambient temperature in the same solvent.

Compounds of formula I in which X represents $COR^4$, and $R^4$ represents substituted phenyl or heteroaryl, may be prepared by reaction of a compound of formula (6a) with $R^4$-$M^1$:

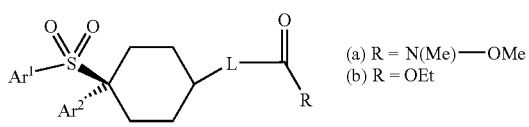

(6)

(a) R = N(Me)—OMe
(b) R = OEt where $M^1$ represents Li or MgBr and $Ar^1$, $Ar^2$ and L have the same meanings as before. The reaction is typically carried out in THF or diethyl ether at reduced temperature. When $M^1$ is MgBr, $R^4$ preferably represents substituted phenyl.

Compounds of formula I in which X represents $COR^4$, and $R^4$ represents $(CR^aR^b)SO_2R^1$, may be prepared by reaction of a compound of formula (6b) with $R^4$—Li. The reaction is typically carried out in THF or diethyl ether at reduced temperature.

Compounds of formula I in which L represents =CH— and X represents $SO_2R^1$ may be prepared by reaction of a cyclohexanone (7):

with $CH_3$—$SO_2R^1$, followed by dehydration of the resulting tertiary alcohol; where $R^1$, $Ar^1$ and $Ar^2$ have the same meanings as before. The first step is typically carried out in THF at −78° C. in the presence of strong base such as lithium diisopropylamide. The dehydration may be effected by converting the alcohol to the corresponding mesylate and treating the latter with 1,8-diazabicyclo[5.4.0]undec-7-ene in THF at ambient temperature.

The compounds of formula (1) in which G is iodide may be obtained by reaction of the corresponding compounds of formula (5) with iodosobenzene diacetate and iodine under irradiation. The compounds of formula (1) in which G is alkyl- or arylsulphonate are available from the reaction of the corresponding compounds of formula (3) with the appropriate sulphonyl chloride.

The sulphonyl chlorides of formula (2) may be obtained by reaction of the compounds of formula (1) with potassium thioacetate, hydrolysis of the resulting thioester to give the corresponding thiol, then treatment of the thiol with potassium nitrate and sulphuryl chloride.

The alcohols of formula (3) in which p is 1, 2 or 3 are available by reduction of the acids of formula (5), the value of p increasing by 1 in the process. The alcohols of formula (3) in which p is 0 are available from the reduction of the cyclohexanones of formula (7). Reduction with L-Selectride™ provides the cis isomer selectively. Reduction with sodium borohydride provides a mixture of cis and trans isomers which may be separated by chromatography.

The amines of formula (4) are available from the carboxylic acids (5) by sequential reaction with oxalyl chloride, sodium azide and benzyl alcohol, followed by hydrolysis of the resulting carbamate. Alternatively, they may be obtained from the mesylates of the alcohols (3) by displacement with azide ion, followed by reduction.

The carboxylic acids of formula (5) in which p is 0 are available from the alcohols (3) in which p is 0 by formation of the mesylate ester, followed by nucleophilic displacement with cyanide ion and hydrolysis of the resulting nitrile. The corresponding acids in which p is 1 are formed by condensation of cyclohexanones (7) with ethyl (diethoxyphosphinyl)acetate, followed by reduction of the resulting alkenyl ester (i.e. (6b) where L is =CH—) and hydrolysis of the ester group. The corresponding acids in which p is 2 or 3 are obtainable by standard methods of homologation. For example, reduction of an acid (5) in which p is 1 provides an alcohol (3) in which p is 2, and mesylation, displacement with cyanide, and hydrolysis provides the corresponding acid in which p is 2. Repeating this process provides the acid (5) in which p is 3.

The N-methoxyamides (6a) are obtained from the corresponding carboxylic acids by treatment first with oxalyl chloride and then with N,O-dimethylhydroxylamine.

Detailed procedures for the synthesis of compounds of formulae (1)–(6), and cyclohexanones (7), are provided in the Examples section.

It will be apparent to those skilled in the art that individual compounds of formula I prepared by the above routes may be converted into other compounds in accordance with formula I by means of well known synthetic techniques such as alkylation, esterification, amide coupling, hydrolysis, oxidation and reduction. Such techniques may likewise be carried out on precursors of the compounds of formula I. For example, a compound of formula I in which X is SCN may be treated with trimethyl(trifluoromethyl)silane and tetrabutylammonium fluoride to provide the corresponding compound in which X is $SCF_3$, which in turn may be oxidised to the corresponding compound wherein X is $SO_2CF_3$. Similarly, a compound of formula I wherein X is $(CR^aR^b)SO_2R^1$ or $CO(CR^aR^b)SO_2R^1$ and one or both of $R^a$ and $R^b$ is H may be alkylated so as to provide the corresponding compound in which one or both of $R^a$ and $R^b$ is alkyl. Alternatively, if in the aforesaid compound $R^b$ is $CO_2H$, decarboxylation via refluxing with sodium chloride in DMSO provides the corresponding compound in which $R^b$ is H.

Also, substituents on the aromatic groups $Ar^1$ or $Ar^2$ may be added or interconverted by means of standard synthetic processes carried out on the compounds of formula I or their precursors. For example, in esters (6b) a chlorine or bromine atom on $Ar^1$ or $Ar^2$ may be replaced by vinyl by treatment with vinyltributyltin in the presence of tri-t-butylphosphine, cesium fluoride and tris(dibenzylideneacetone)dipalladium (0). Ozonolysis of the vinyl group provides the corresponding formyl derivative, which may be transformed in a variety of ways, including oxidation to the corresponding acid, reduction to the corresponding benzyl alcohol, and conversion to the corresponding nitrile by treatment with hydroxylamine then triphenylphosphine and carbon tetrachloride.

Compounds of formula I in which L comprises a pendant alkyl group are obtainable by alkylation of the corresponding compounds wherein L is —$(CH_2)_n$—, or by alkylation of a precursor such as an ester (6b) wherein L is —$(CH_2)_n$—.

Pyridine groups may be oxidised to the corresponding N-oxides by treatment with urea hydrogen peroxide and trifluoroacetic anhydride in dichloromethane at 0° C.

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, $3^{rd}$ ed., 1999. The protecting groups may be removed at a convenient subsequent stage using methods known from the art.

An assay which can be used to determine the level of activity of compounds of the present invention is described in WO01/70677. A preferred assay to determine such activity is as follows:
1) SH-SY5Y cells stably overexpressing the βAPP C-terminal fragment SPA4CT, are cultured at 50–70% confluency. 10 mM sodium butyrate is added 4 hours prior to plating.
2) Cells are plated in 96-well plates at 35,000 cells/well/100 μL in Dulbecco's minimal essential medium (DMEM) (phenol red-free)+10% foetal bovine serum (FBS), 50 mM HEPES buffer (pH7.3), 1% glutamine.
3) Make dilutions of the compound plate. Dilute stock solution 18.2× to 5.5% DMSO and 11× final compound concentration. Mix compounds vigorously and store at 4° C. until use.
4) Add 10 μL compound/well, gently mix and leave for 18 h at 37° C., 5% $CO_2$.
5) Prepare reagents necessary to determine amyloid peptide levels, for example by Homogeneous Time Resolved Fluorescence (HTRF) assay.
6) Plate 160 μL aliquots of HTRF reagent mixture to each well of a black 96-well HTRF plate.
7) Transfer 40 μL conditioned supernatant from cell plate to HTRF plate. Mix and store at 4° C. for 18 hours.
8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.
9) Add 10 μL/well MTS/PES solution to the cells; mix and leave at 37° C.
10) Read plate when the absorbance values are approximately 0.4–0.8. (Mix briefly before reading to disperse the reduced formazan product).
11) Quantitate amyloid beta 40 peptide using an HTRF plate reader. Alternative assays are described in *Biochemistry*, 2000, 39(30), 8698–8704. See also, *J. Neuroscience Methods*, 2000, 102, 61–68.

The Examples of the present invention all had an $ED_{50}$ of less than 1 μM, typically less than 0.5 μM, in most cases less than 100 nM, and in preferred cases less than 10 nM, in at least one of the above assays.

The following examples illustrate the present invention.

EXAMPLES

Intermediate A

4-[(4-Chlorophenyl)sulfonyl]-4-(2,5-difluorophenyl)cyclohexanone

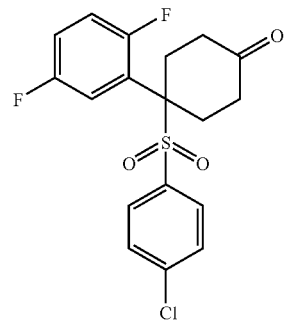

4-Chlorothiophenol (3.6 g, 0.025 mol) in dichloromethane (100 mL) was treated with 2,5-difluorobenzyl bromide (5.17 g, 0.025 mol) and triethylamine (3.9 ml, 0.028 mol). The reaction was stirred for 2 hours then diluted with dichloromethane (250 mL) and washed with water (100 mL) and brine (100 mL). The separated organic layer was dried (MgSO$_4$), evaporated to dryness, and the product purified by passing down a plug of silica eluting with hexane-ethyl acetate mixtures to give 4-chlorophenyl 2,5-difluorobenzyl sulfide (5.12 g). $^1$H NMR CDCl$_3$ 7.23 (4H, s), 6.69–6.86 (3H, m) and 4.04 (2H, s).

This thioether (5.12 g, 0.018 mol) in dichloromethane (100 mL) was treated with m-chloroperoxybenzoic acid (50% w/w, 14.3 g, 0.042 mol) and stirred for 2 hours. The reaction was washed with sodium sulfite (5% aqueous, 100 mL) and brine (50 mL), dried (MgSO$_4$) and evaporated to dryness. The sulphone product was purified by flash chromatography on silica eluting with hexane-ethyl acetate mixtures to give the sulfone (3.6 g). $^1$H NMR (CDCl$_3$) δ 7.61 (2H, d, J=8.6 Hz), 7.45 (2H, d, J=8.6 Hz), 7.13–7.08 (1H, m), 7.05–7.01 (1H, m), 6.99–6.87 (1H, m) and 4.36 (2H, s).

A solution of this sulfone (1 g, 3.31 mmol) and methyl acrylate (0.84 mL, 9.27 mmol) in tetrahydrofuran (30 mL) was treated dropwise with potassium $^t$butoxide (1M solution in tetrahydrofuran, 3.64 mL, 3.64 mmol). The reaction was stirred for 2 hours, diluted with ethyl acetate (100 mL) and washed with water (50 mL) and brine (50 mL). The organic phase was separated, dried (MgSO$_4$) and evaporated to dryness, and the product purified by flash chromatography on silica eluting with hexane-ethyl acetate mixtures to give 1.0 g cyclised product. $^1$H NMR (CDCl$_3$) δ 12.0 (1H, s), 7.41 (4H, s), 7.06–7.0 (2H, m), 6.87–6.81 (1H, s), 3.81 (3H, s), 3.38 (1H, dd, J=3.2, 15.8 Hz), 3.02–2.92 (2H, m), 2.52 (1H, dd, J=5.7, 18.5 Hz), 2.3–2.2 (1H, m) and 2.2–2.1 (1H, m).

The ester from the foregoing step (1.0 g, 2.25 mmol) in dimethylsulfoxide (10 mL) was treated with sodium chloride (0.3 g, 4.96 mmol) and water (0.9 mL, 4.96 mmol) and heated at 150° C. for 2 hours. The cooled reaction mixture was diluted with ethyl acetate (100 mL), washed with saturated aqueous ammonium chloride solution (100 mL), dried (MgSO$_4$) and evaporated to dryness. The product was purified by flash chromatography on silica eluting with hexane-ethyl acetate mixtures to give the cyclohexanone (0.5 g). $^1$H NMR (CDCl$_3$) δ 7.43–7.37 (4H, m), 7.22–7.1 (2H, m), 6.97–6.9 (1H, m), 3.05–2.98 (2H, m), 2.61–2.53 (4H, m) and 2.25–2.15 (2H, m).

Intermediate B

[4-(4-Chloro-benzenesulfonyl)-4-(2,5-difluoro-phenyl)-cyclohexyl]-acetic acid ethyl ester

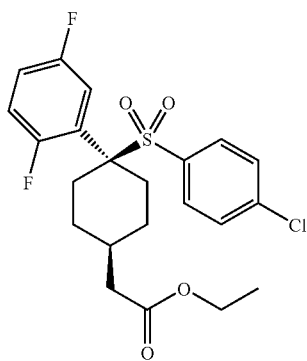

Ethyl (diethoxyphosphinyl)acetate (5.16 mL, 26 mmol) was added dropwise to a slurry of sodium hydride (60% dispersion in mineral oil, 988 mg, 24.7 mmol) in tetrahydrofuran (60 mL) and the mixture was stirred at room temperature for 1 h. Intermediate A (5 g, 13 mmol) in tetrahydrofuran (50 mL) was added dropwise over 20 min. and the mixture was stirred at room temperature for 18 h. Water was added and the mixture was extracted with ethyl acetate. The combined organic fractions were washed with water, dried (MgSO$_4$) and the solvent was evaporated under reduced pressure. The residue was purified by flash column chromatography on silica gel, eluting with isohexane:ethyl acetate (85:15), to give the product as a white solid (5.2 g, 88%). $^1$H NMR (400 MHz, CDCl$_3$) δ 7.41–7.36 (4H, m), 7.18–7.13 (1H, m), 7.11–7.05 (1H, m), 6.93–6.86 (1H, m), 5.64 (1H, s), 4.14–4.10 (2H, m), 3.99–3.96 (1H, m), 2.91–2.80 (2H, m), 2.42–2.38 (1H, m), 2.31–2.04 (3H, m), 1.89–1.78 (1H, m), 1.28–1.24 (3H, m).

The foregoing unsaturated ester (1 g, 2.2 mmol) in dry tetrahydrofuran (10 mL), was treated with L-Selectride™ (1.0 M solution in tetrahydrofuran, 2.64 mL) at 0° C. The reaction was stirred for 2 h, quenched with aqueous hydrochloric acid (1N, 10 mL) and the product extracted into ethyl acetate (2×20 mL). The combined organic layers were washed with brine (20 mL), dried (MgSO$_4$), filtered and evaporated to dryness. Pure product (0.51 g) was obtained after silica chromatography eluting with hexane-ethyl acetate mixtures (10–30%).

$^1$H NMR (400 MHz, CDCl$_3$) 7.37–7.30 (4H, m), 7.09–7.00 (2H, m), 6.86–6.79 (1H, m), 4.14 (2H, q, J=7.1 Hz), 2.47 (2H, d, J=7.6 Hz), 2.46–2.38 (2H, m), 2.19–2.14 (1H, m), 1.76–1.71 (2H, m), 1.57–1.48 (4H, m), 1.27 (3H, t, J=7.1 Hz).

Intermediate C

[4-(4-Chlorophenylsulfonyl)-4-(2,5-difluoro-phenyl)-cyclohexyl]-acetic acid

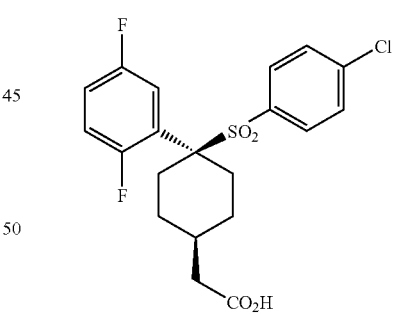

Lithium hydroxide (350 mg, 14.57 mmol) was added to a solution of Intermediate B (1.33 g, 2.91 mmol) in ethanol (40 mL) which was then degassed and stirred at room temperature under nitrogen gas for 5 h. The mixture was poured into aqueous hydrochloric acid (1M), extracted with ethyl acetate, the organic extract dried (MgSO$_4$), and the solvent evaporated under reduced pressure to give a white solid which was then crystallized from 2-propanol to give the product as a white solid (950 mg, 76%). $^1$H NMR (400 MHz, CD$_3$OD) δ 7.51–7.49 (2H, m), 7.40–7.37 (2H, m), 7.19–7.10 (2H, m), 7.00–6.94 (1H, m), 2.51–2.35 (6H, m), 2.13–2.10 (1H, m), 1.78–1.74 (2H, m), 1.57–1.50 (2H, m).

Intermediate D

2-[4-(4-Chloro-benzenesulfonyl)-4-(2,5-difluoro-phenyl)-cyclohexyl]-ethanol

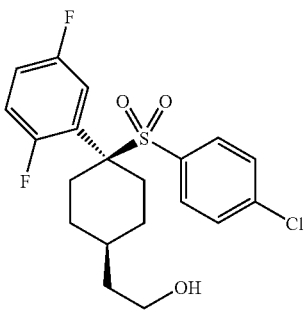

To Intermediate C (1 g, 2.3 mmol) in dry tetrahydrofuran (80 mL) at 0° C. under nitrogen were added triethylamine (0.4 mL, 2.8 mmol) and iso-butylchloroformate (0.36 mL, 2.8 mmol). The reaction was stirred for 1.5 h, filtered, the filtrate re-cooled to 0° C. and sodium borohydride (435 mg, 11 mmol) in water (10 mL) added dropwise. After stirring at 0° C. for 1 h the reaction was concentrated, diluted with ethyl acetate, washed with water and brine and then dried (MgSO$_4$), filtered and evaporated. The residue was purified by flash column chromatography on silica, eluting with iso-hexane/ethyl acetate (1:1), to give the alcohol as a white solid (960 mg).

$^1$H NMR (CDCl$_3$) δ 7.36 (2H, d, J=6.7 Hz), 7.33 (2H, d, J=6.7 Hz), 7.12–7.00 (2H, m), 6.88–6.78 (1H, m), 3.70 (2H, t, J=6.3 Hz). 2.42–2.40 (4H, m), 1.76–1.69 (4H, m), 1.65–1.45 (4H, m).

Intermediate E

Iodo-[4-(4-Chloro-benzenesulfonyl)-4-(2,5-difluoro-phenyl)-cyclohexyl]-methane

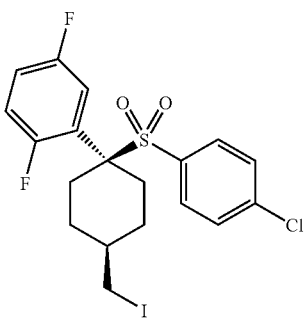

A stirred solution of Intermediate C (6.85 g, 16.0 mmol.), iodosobenzene diacetate (14.4 g, 44.7 mmol.) and iodine (6.20 g, 24 mmol.) in dry benzene (200 mL) was heated to reflux under irradiation by a 250 W tungsten lamp. After 45 minutes, further iodosobenzene diacetate (3.0 g, 9.3 mmol.) and iodine (1.5 g, 5.8 mmol.) were added and reflux under irradiation continued for a further 1 h. The reaction was cooled and diluted with ethyl acetate (200 mL) then washed with aqueous sodium thiosulfate (10%, 2×200 mL), water (200 mL), aqueous sodium hydroxide solution (1M, 200 mL) and brine (200 mL) then dried (MgSO$_4$) and evaporated to leave a residue which was purified by flash column chromatography on silica, eluting with ether:dichloromethane:iso-hexane (1:1:8), to afford iodo-[4-(4-chloro-benzenesulfonyl)-4-(2,5-difluoro-phenyl)-cyclohexyl]-methane (6.00 g, 74%). $^1$H NMR (CDCl$_3$) δ 7.36 (2H, d, J=8.8 Hz), 7.31 (2H, d, J=8.8 Hz), 7.09–7.02 (2H, m), 6.86–6.79 (1H, m), 3.35 (2H, d, J=7.5 Hz), 2.45–2.38 (4H, m), 2.04–1.91 (3H, m) and 1.64–1.53 (2H, m).

Intermediate F

2-Iodo-[4-(4-Chloro-benzenesulfonyl)-4-(2,5-difluoro-phenyl)-cyclohexy]-ethane

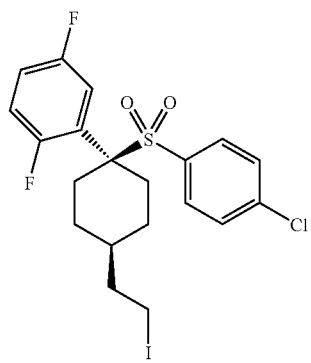

A solution of Intermediate D (414 mg, 1 mmol), imidazole (272 mg, 4 mmol) and triphenylphosphine (524 mg, 2 mmol) in toluene (15 mL) was stirred at room temperature for 10 minutes, then iodine (279 mg, 1.1 mmol) was added. The reaction was stirred at ambient temperature for 2.5 h then at 65° C. for 1 h. Upon cooling, the mixture was decanted and evaporated to dryness. The residue was extracted into ether (3×50 mL) and the combined organics evaporated then filtered through a plug of silica, eluting with ether:iso-hexane (1:4) to give the desired iodide (252 mg).
$^1$H NMR (CDCl$_3$) δ 7.36 (2H, d, J=8.8 Hz), 7.30 (2H, d, J=8.8 Hz), 7.08–7.01 (2H, m), 6.86–6.79 (1H, m), 3.21 (2H, t, J=7.0 Hz), 2.48–2.32 (4H, m), 1.98 (2H, q, J=7.0 Hz), 1.80–1.65 (3H, m) and 1.52–1.44 (2H, m)

Intermediate G 4-(4-Chloro-benzenesulfonyl)-4-(2,5-difluoro-phenyl)-cyclohexanol

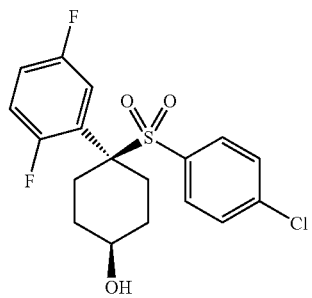

A solution of Intermediate A (10.05 g, 26 mmol) in tetrahydrofuran (200 mL) cooled to −78° C. was treated with L-Selectride™ (1.0 M solution in tetrahydrofuran, 31.4 mL, 31.4 mmol). After stirring at −78° C. for 2 hours the reaction was quenched with aqueous hydrochloric acid (2M). The solvent was evaporated and the product extracted into ethyl acetate and washed with water followed by brine, and evaporated to an oil which was purified by flash chromatography eluting with ethyl acetate:hexane 1:1 to afford the desired intermediate (6 g). $^1$H NMR (CDCl$_3$) δ 7.39–7.35 (4H, m), 7.14–7.03 (2H, m), 6.90–6.83 (1H, m), 3.95 (1H, m), 2.65–2.45 (4H, m), 1.92–1.80 (2H, m) and 1.50–1.38 (2H, m)

Intermediate H

2-[4-(4-Chloro-benzenesulfonyl)-4-(2,5-difluoro-phenyl)-cyclohexyl]-N-methoxy-N-methyl-acetamide

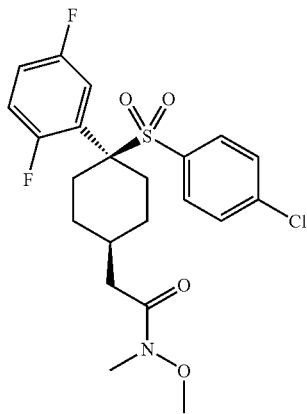

To a stirred solution of Intermediate C in THF (100 mL) was added oxalyl chloride (1.35 mL, 15.5 mmol.) then N,N-dimethylformamide (1 drop) and the effervescing reaction stirred at ambient temperature for 90 minutes then evaporated. The residue was azeotroped with toluene (50 mL), then taken up in dichloromethane (100 mL). N,O-dimethylhydroxylamine hydrochloride salt (1.74 g, 17.9 mmol.) was added followed by Hunig's base (6.2 mL, 35.7 mmol.). After stirring for 30 minutes the solvent was evaporated and the residue purified by flash column chromatography on silica, eluting with ethyl acetate:iso-hexane (2:3), to afford the desired product (4.4 g). $^1$H NMR (CDCl$_3$) δ 7.38–7.31 (4H, m), 7.09–7.01 (2H, m), 6.86–6.79 (1H, m), 3.73 (3H, s), 3.19 (3H, s), 2.57 (2H, d, J=7.5 Hz), 2.51–2.36 (4H, m), 2.24 (1H, m), 1.77–1.72 (2H, m) and 1.6–1.5 (2H, m). MS (ES+) 472 ([MH]$^+$).

Intermediate I

[4-(4-Chloro-benzenesulfonyl)-4-(2,5-difluoro-phenyl)-cyclohexyl]-methanethiol

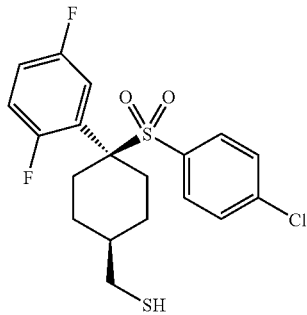

To a solution of Intermediate E (2.05 g, 4.0 mmol.) in N,N-dimethylformamide (80 mL) was added potassium thioacetate (2.3 g, 20 mmol.) and the solution stirred for 2 h. at ambient temperature then diluted with water (100 mL) and extracted into ether (2×100 mL). The combined organic layers were washed with water (3×100 mL) and brine (100 mL), dried (MgSO$_4$) and evaporated to leave the crude thioacetic acid 4-(4-chloro-benzenesulfonyl)-4-(2,5-difluoro-phenyl)-cyclohexylmethyl ester (1.81 g). This was dissolved in methanol (80 mL), 1M aqueous sodium hydroxide solution (20 mL) was added and the mixture vigorously stirred for 1 h. Water (50 mL) was added and the mixture extracted into ethyl acetate (2×100 mL). The combined organic layers were washed with water (100 mL) and brine (100 mL), dried (MgSO$_4$) and evaporated to leave a residue of the desired thiol (1.65 g, quant.). $^1$H NMR (CDCl$_3$) δ 7.36 (2H, d, J=8.8 Hz), 7.32 (2H, d, J=8.8 Hz), 7.11–7.00 (2H, m), 6.88–6.78 (1H, m), 2.68 (2H, t, J=8.0 Hz), 2.48–2.30 (4H, m), 2.0–1.9 (2H, m), 1.7–1.6 (1H, m), 1.58–1.45 (2H, m) and 1.32 (1H, t, J=8.0 Hz).

Intermediate J

C-[4-(4-Chloro-benzenesulfonyl)-4-(2,5-difluoro-phenyl)-cyclohexyl]-methylamine

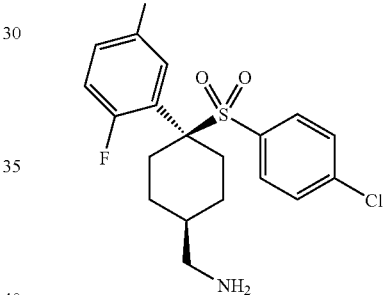

To a stirred solution of Intermediate C (75 mg, 0.18 mmol.) in tetrahydrofuran (10 mL) was added oxalyl chloride (0.02 mL, 0.23 mmol.) and N,N-dimethylformamide (1 drop) and the mixture stirred at ambient temperature for 90 minutes then evaporated. Toluene (10 mL) was added then evaporated and the residue taken up in benzene (2 mL) and cooled in an ice bath. A solution of tetrabutylammonium bromide (1 mg) and sodium azide (23 mg, 0.36 mmol.) in water (1 mL) was added, the cooling bath removed and the mixture allowed to stir at ambient temperature for 2 hours. The layers were separated and the organic phase washed with brine (10 mL), dried (MgSO$_4$) and filtered. Benzyl alcohol (0.1 mL) was added and the mixture heated to reflux for 18 hours then cooled and diluted with ethyl acetate (10 mL), washed with water (10 mL) and brine (10 mL), dried (MgSO$_4$) and evaporated to leave a residue which was purified by flash column chromatography on silica, eluting with ethyl acetate:iso-hexane (1:3), to afford the desired benzyl carbamate (60 mg). $^1$H NMR (CDCl$_3$) δ 7.37–7.28 (9H, m), 7.07–7.00 (2H, m), 6.86–6.79 (1H, m), 5.10 (2H, s), 4.85 (1H, t, J=6.0 Hz), 3.29 (2H, t, J=6.0 Hz), 2.49–2.31 (4H, m), 1.82–1.65 (3H, m) and 1.54–1.41 (2H, m). MS (ES+) 534 ([MH]$^+$).

To the foregoing carbamate (40 mg, 0.08 mmol.) was added hydrobromic acid (1 mL of a 45% w/v solution in acetic acid). The reaction was stirred for 90 minutes, diethyl ether (10 mL) and water (10 mL) added, the organic phase washed with aqueous hydrochloric acid (2N, 10 mL), the combined aqueous phases basified to pH 12 with 4N aqueous sodium hydroxide solution then extracted into ethyl acetate (2×10 mL). The combined organic layers were dried (MgSO$_4$) and evaporated to give the primary amine intermediate (26 mg) which was used without further purification. $^1$H NMR (CDCl$_3$) δ 7.36 (2H, d, J=8.8 Hz), 7.31 (2H, d, J=8.8 Hz), 7.10–7.00 (2H, m), 6.87–6.80 (1H, m), 2.81 (2H, d, J=7.3 Hz), 2.44–2.32 (4H, m), 1.86–1.81 (2H, m) and 1.6–1.44 (3H, m).

Intermediate K 4-(2,5-Difluoro-phenyl)-4-(4-trifluoromethyl-benzenesulfonyl)-cyclohexanone

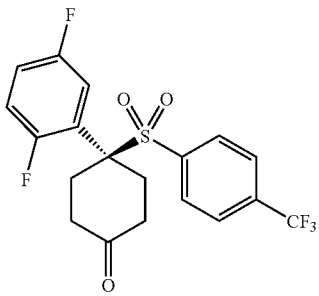

Prepared by the method of Intermediate A. $^1$H NMR (360 MHz, CDCl$_3$) δ 7.71–7.69 (2H, d, J=7.5 Hz), 6.62–6.60 (2H, d, J=7.5 Hz), 7.22–7.11 (2H, m), 6.95–6.88 (1H, m), 3.02–2.99 (2H, m), 2.63–2.54 (4H, m) and 2.25–2.16 (2H, m).

Intermediate L

[4-(2,5-Difluoro-phenyl)-4-(4-trifluoromethyl-benzenesulfonyl)-cyclohexyl]-acetic acid

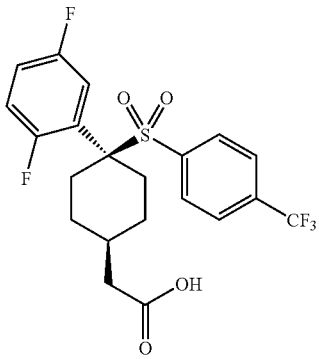

Prepared from the Intermediate K, by the method of Intermediate C. $^1$H NMR (360 MHz, CDCl$_3$) δ 1.52–1.61 (2H, m), 1.76–1.81 (2H, m), 2.20–2.26 (1H, m), 2.40–2.50 (4H, m), 2.54 (2H, d, J=7.5 Hz), 6.75–6.83 (1H, m), 7.01–7.08 (2H, m), 7.51 (2H, d, J=8.3 Hz) and 7.64 (2H, d, J=8.3 Hz). MS (ES+) 462 ([MH]$^+$).

Intermediate M

Iodo-[4-(2,5-Difluoro-phenyl)-4-(4-trifluoromethyl-benzenesulfonyl)-cyclohexyl]-methane

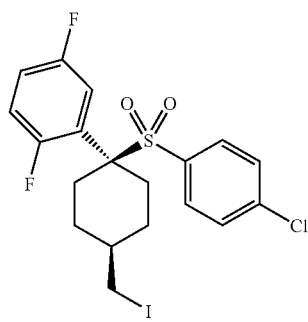

Prepared from Intermediate L by the method of Intermediate E. $^1$H NMR (CDCl$_3$) δ 1.55–1.65 (2H, m), 1.89–2.03 (3H, m), 2.30–2.50 (4H, m), 3.37 (2H, d, J=7.Hz), 6.76–6.84 (1H, m), 7.02–7.10 (2H, m), 7.51 (2H, d, J=7.4 Hz), 7.64 (2H, d, J=7.4 Hz).

Intermediate N

2-[4-(2,5-Difluoro-phenyl)-4-(4-trifluoromethyl-benzenesulfonyl)-cyclohexyl]-ethanol

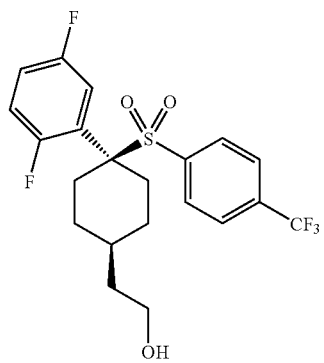

Intermediate L (14.1 g, 0.031 mol) in tetrahydrofuran (250 mL) was treated with triethylamine (5.1 mL, 0.036 mol) and $^t$butylchloroformate (4.64 mL, 0.036 mol) at 0° C. After stirring for 1.5 hours, the precipitate was filtered off and the filtrate re-cooled to 0° C., before being treated with sodium borohydride (1.9 g, 0.05 mol) in water (10 mL) and stirred for 1 hour. The reaction was concentrated, diluted with ethyl acetate and washed with water and brine. The separated organic phase was dried over magnesium sulfate, filtered and evaporated to dryness. The alcohol was purified by silica gel chromatography eluting with ethyl acetate and hexane mixtures to give 11.5 g. $^1$H NMR (360 MHz, CDCl$_3$) δ 7.64 (2H, d, J=8.3 Hz), 7.53 (2H, d, J=8.3 Hz), 7.10–7.0 (2H, m), 6.84–6.76 (1H, m), 3.71 (2H, t, J=6.3 Hz), 2.54–2.43 (4H, m) and 1.79–1.44 (8H, m).

Intermediate O

4-(2,5-Difluoro-phenyl)-4-(4-trifluoromethyl-benzenesulfonyl)-cyclohexanol

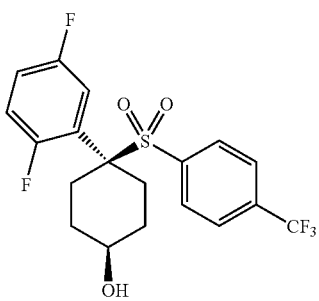

Prepared from Intermediate K by the method of Intermediate G. $^1$H NMR (CDCl$_3$) δ 7.67 (2H, d, J=7.5 Hz), 7.60 (2H, m, J=7.5 Hz), 7.14–7.03 (2H, m), 6.88–6.81 (1H, m), 3.95 (1H, t, J=2.1 Hz). 2.65–2.53 (4H, m), 1.89–1.85 (2H, m), 1.48 (1H, br s), 1.27–1.24 (2H, m).

Intermediate P

Methanesulfonic acid 2-[4-(2,5-difluoro-phenyl)-4-(4-trifluoromethyl-benzenesulfonyl)-cyclohexyl]-ethyl ester

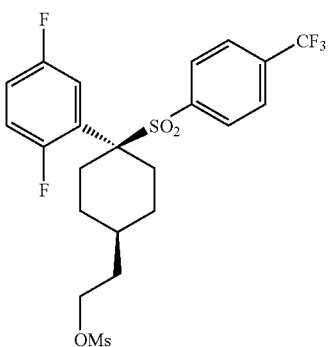

Intermediate N (3.80 g, 8.48 mmol) and triethylamine (1.17 mL) in dichloromethane (150 mL) was treated dropwise with mesyl chloride, maintaining the internal temperature below −40° C. After complete addition the reaction was allowed to warm to room temperature and stirred for 1 hour. The reaction mixture was washed with water (50 mL), 10% aqueous citric acid (50 mL) and saturated sodium bicarbonate solution (50 mL) then dried over magnesium sulfate. After evaporation to dryness, the product was triturated with diethyl ether to give 4.2 g. $^1$H NMR (CDCl$_3$) δ 7.65 (2H, d, J=8.2 Hz), 7.52 (2H, d, J=8.2 Hz), 7.26–7.02 (2H, m), 6.83–6.77 (1H, m), 4.29 (2H, t, J=6.4 Hz), 3.01 (3H, s), 2.45–2.42 (4H, m), 1.95–1.90 (2H, m), 1.83–1.73 (3H, m) and 1.58–1.54 (2H, m).

Intermediate Q

[4-(4-chloro-benzenesulfonyl)-4-(2,5-difluoro-phenyl)-cyclohexyl]-methanesulfonyl Chloride

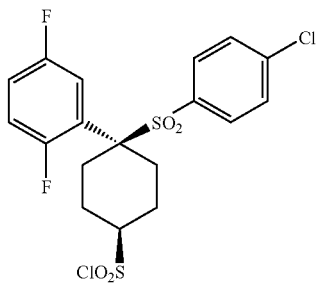

Intermediate I (1.65 g, 4.0 mmol.) in acetonitrile (120 mL) was cooled to 0° C. under nitrogen. Potassium nitrate (1.01 g, 10 mmol.) then sulfuryl chloride (0.80 mL, 10 mmol.) were added, the mixture stirred at 0° C. for 2 hours, then diluted with a saturated aqueous solution of sodium hydrogencarbonate (100 mL). The mixture was extracted into ethyl acetate (2×100 mL) and the combined organics washed with saturated aqueous sodium hydrogencarbonate (100 mL) and brine (100 mL), dried (MgSO$_4$) and evaporated to leave a residue which was purified by column chromatography on silica, eluting with diethyl ether:isohexane (1:2), to afford [4-(4-chloro-benzenesulfonyl)-4-(2,5-difluoro-phenyl)-cyclohexyl]-methanesulfonyl chloride as a colourless solid (0.81 g). $^1$H NMR (CDCl$_3$) δ 7.37 (2H, d, J=8.7 Hz), 7.30 (2H, d, J=8.7 Hz), 7.08–7.04 (2H, m), 6.87–6.80 (1H, m), 3.87 (2H, d, J=6.5 Hz), 2.56–2.41 (5H, m), 2.07–2.02 (2H, m) and 1.77–1.67 (2H, m).

Intermediate R

4-[(4-Chlorophenyl)sulfonyl]-4-(2,5-difluorophenyl) cyclohexylamine

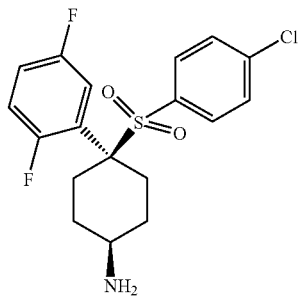

(1) Intermediate A (0.1 g, 0.26 mmol) in methanol (2 ml) was treated with NaBH$_4$ (0.098 g, 0.26 mmol) and stirred for 1 hour. The reaction was quenched with HCl (1N, 10 ml), diluted with ethyl acetate (20 ml), then the organic phase was separated, dried (MgSO$_4$) and evaporated to dryness. The trans 4-[(4-chlorophenyl)sulfonyl]-4-(2,5-difluorophenyl)cyclohexanol was purified on silica eluting with hexane-ethyl acetate mixtures. 0.052 g. $^1$H NMR CDCl$_3$ 7.39–7.33 (4H, m), 7.11–7.02 (2H, m), 6.88–6.82

(1H, m), 3.80–3.73 (1H, m), 2.80–2.60 (2H, m), 2.22–2.16 (2H, m), 2.08–2.04 (2H, m), 1.53 (1H, br) and 1.27–1.13 (2H, m).

(2) The trans alcohol (2.7 g, 6.9 mmol) and triethylamine (1.45 ml, 10.3 mmol) in dichloromethane (50 ml) were treated with methanesulphonyl chloride (0.645 ml, 8.9 mmol) at −30° C. After 30 minutes the mixture was washed with water (20 ml), 10% aqueous citric acid (20 ml) and saturated aqueous sodium hydrogen carbonate (50 ml), dried (MgSO$_4$) and evaporated to dryness. The solid was triturated with ether to give the trans mesylate (2.6 g) $^1$H NMR (CDCl$_3$) 7.40–7.37 (4H, m), 7.12–7.07 (2H, m), 6.92–6.83 (1H, m), 4.78–4.65 (1H, m), 2.96 (3H, s), 2.88–2.52 (2H, m), 2.29–2.21 (4H, m) and 1.59–1.47 (2H, m).

(3) The mesylate (1.5 g, 3.2 mmol) and sodium azide (315 mg, 4.8 mmol) in dimethylformamide (5 ml) were heated to 90° C. for 6 hrs. The mixture was treated with water (80 ml), and extracted with diethyl ether (3×50 ml), dried (MgSO$_4$) and evaporated to dryness. The solid was triturated with ether to give cis 4-azido-1-[(4-chlorophenyl)sulfonyl]-1-(2,5-difluorophenyl)cyclohexane (1.4 g) $^1$H NMR (CDCl$_3$) 7.40–7.34 (4H, m), 7.12–7.03 (2H, m), 6.90–6.83 (1H, m), 3.78–3.76 (1H, m), 2.62–2.41 (4H, m), 1.97–1.91 (2H, m) and 1.51–1.41 (2H, m).

(4) The cis azide (1 g, 2.55 mmol), in tetrahydrofuran (10 ml) and water (1 ml), was treated with triphenylphosphine (740 mg, 2.8 mmol) at room temperature for 15 mins and then water (5 ml) was added and the mixture was heated at reflux for 4 hrs. The mixture was allowed to cool to room temperature and then passed through SCX Varian Bond Elut™ cartridge. The basic fraction was evaporated to give the primary amine. $^1$H NMR (CDCl$_3$) 7.35 (4H, s), 7.12–7.01 (2H, m), 6.88–6.81 (1H, m), 3.13–3.11 (1H, m), 2.64–2.44 (4H, m), 1.78–1.68 (2H, m) and 1.52–1.39 (2H, m). MS MH+ 386 (388).

Intermediate S 4-(2,5-Difluorophenyl)-4-(4-trifluoromethylbenzenesulfonyl)-cyclohexylamine

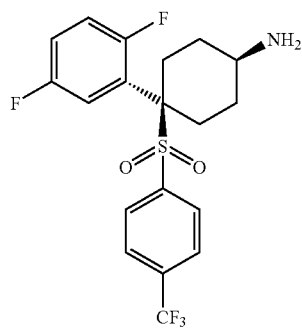

Prepared as for Intermediate R, using Intermediate K, except that the borohydride reduction was carried out at −20° C.

MS (ES+) MH+ 420

Intermediate T 4-(2,5-Difluorophenyl)-4-(6-trifluoromethyl-pyridine-3-sulfonyl)-cyclohexylamine

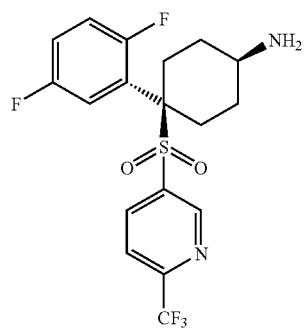

(1) A solution of 3-amino-6-(trifluoromethyl)pyridine (1.62 g, 0.01 mol) in concentrated hydrochloric acid (1.7 mL), was treated with ice (2 g) and cooled to 0° C. Sodium nitrite (0.71 g, 0.01 mol) in water (2 mL) was added slowly, the reaction mixture stirred for 5 minutes at 0° C. then treated slowly with a solution of potassium ethyl xanthate (1.92 g, 0.012 mol) in ethanol-water. The reaction mixture was heated at 50–55° C. for 30 minutes, cooled and diluted with diethyl ether and water. The organic layer was washed with brine, dried (MgSO$_4$) and evaporated in vacuo. The resulting xanthate was dissolved in ethanol (30 mL) and treated with potassium hydroxide (3 g) and refluxed (90° C.) for 2 h. After cooling and filtering, the filtrate was acidified with citric acid and diluted with diethyl ether. The organic layer was washed with brine, dried (MgSO$_4$) and evaporated in vacuo. Purification by column chromatography on silica gave the (trifluoromethyl)pyridinethiol as a yellow oil (0.79 g, 44%).

$^1$H NMR (360 MHz, CDCl$_3$) 8.57 (1H, d, J=2.0 Hz), 7.74 (1H, dd, J=8.1, 2.0 Hz), 7.54 (1H, d, J=8.1 Hz), 3.62 (1H, s).

(2) This thiol (0.5 g, 2.8 mmol) was reacted first with 2,5-difluorobenzyl bromide and subsequently with 3-chloroperoxybenzoic acid by the procedure described for Intermediate 1 to gave the pyridyl benzyl sulfone as a white powder (0.82 g, 87% over 2 steps).

$^1$H NMR (400 MHz, CDCl$_3$) δ 8.93 (1H, d, J=2.1 Hz), 8.18 (1H, dd, J=8.1, 2.1 Hz), 7.80 (1H, d, J=8.1 Hz), 7.21–7.17 (1H, m), 7.10–7.04 (1H, m), 6.93–6.88 (1H, m), 4.46 (2H, s).

(3) This sulfone (50 mg, 0.15 mmol) in tetrahydrofuran (5 mL) at 0° C. was treated with potassium tert-butoxide (17 mg, 0.15 mmol), then with 2,2-bis(2-iodoethyl)-1,3-dioxolane (H. Niwa et al, J. Am. Chem. Soc., 1990, 112, 9001) (86 mg, 0.23 mmol), stirred for 1 h at room temperature and then for 1 h at 70° C. The cooled reaction mixture was treated with more potassium tert-butoxide (1.2 equivalents) and 2,2-bis(2-iodoethyl)-1,3-dioxolane (0.3 equivalents). After heating at 70° C. for 1 h, then cooling to room temperature, the reaction mixture was diluted with diethyl ether and water, the layers separated and the organic layer washed with water and brine, dried (MgSO$_4$) and evaporated in vacuo. Purification by column chromatography on silica gave the desired cyclohexanone cyclic ketal (38 mg, 56%) as a white solid.

$^1$H NMR (360 MHz, CDCl$_3$) δ 8.68 (1H, d, J=2.0 Hz), 7.92 (1H, dd, J=2.0, 8.1 Hz), 7.73 (1H, d, J=8.1 Hz), 7.19–7.07 (2H, m), 6.90–6.82 (1H, m), 3.99–3.88 (4H, m), 2.7 (2H, vbrm), 2.5 (2H, vbrappt), 1.85 (2H, brappd), 1.54–1.26 (2H, m).

(4) This ketal (30 mg, 0.065 mmol) was heated at 50° C. overnight with p-toluenesulfonic acid (15 mg) in 80% acetic acid-water. The reaction mixture was partitioned between diethyl ether and water and the organic layer washed with saturated aqueous sodium hydrogencarbonate solution and brine, dried (MgSO$_4$) and evaporated in vacuo. Purification by column chromatography on silica gave the cyclohexanone (25 mg, 92%) as a white solid.

$^1$H NMR (400 MHz, CDCl$_3$) δ 8.67 (1H, d, J=2.0 Hz), 7.97 (1H, dd, J=8.1, 2.0 Hz), 7.77 (1H, d, J=8.1 Hz), 7.28–7.16 (2H, m), 6.99–6.90 (1H, m), 3.01–2.97 (2H, m), 2.68–2.57 (4H, m), 2.26–2.17 (2H, m).

(5) The cyclohexanone was converted to the title amine by the procedure of Intermediate R, except that the borohydride reduction was carried out at −78° C. M/Z 421 (MH$^+$).

Example 1

C-[4-(4-Chloro-benzenesulfonyl)-4-(2,5-difluoro-phenyl)-cyclohexyl]-N-phenyl-methanesulfonamide

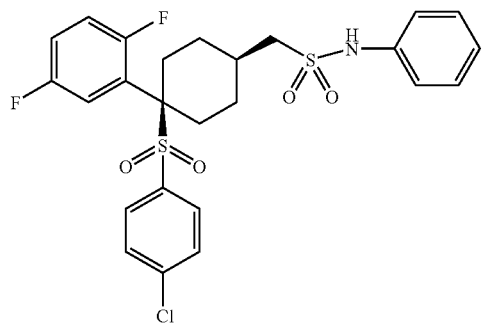

To a stirred solution of Intermediate Q (100 mg, 0.21 mmol) in tetrahydrofuran (10 mL) under nitrogen was added aniline (94.5 μL, 1.04 mmol). The mixture was stirred and heated to reflux for 12 hours, cooled, diluted with ethyl acetate and washed with hydrochloric acid (2N aqueous) and brine, dried (MgSO$_4$) and evaporated to leave a residue which was purified by preparative thin layer chromatography eluting with diethyl ether:dichloromethane:iso-hexane 1:1:3 to afford the desired product (63 mg).

$^1$H NMR (CDCl$_3$) δ 7.40–7.36 (4H, m), 7.29–7.26 (2H, dd, J=8.7, 2.0 Hz), 7.22–7.20 (3H, m), 7.04–7.02 (2H, m), 6.79–6.86 (1H, m), 6.43 (1H, s), 3.22 (2H, d, J=6.6 Hz), 2.46–2.42 (2H, m), 2.35–2.33 (3H, m), 1.96–1.92 (2H, m) and 1.64–1.59 (2H, m). MS (ES+) 562 ([MNa]$^+$).

Example 2

[4-(2,5-Difluoro-phenyl)-4-(4-trifluoromethyl-benzenesulfonyl)-cyclohexyl]-methanesulfonamide

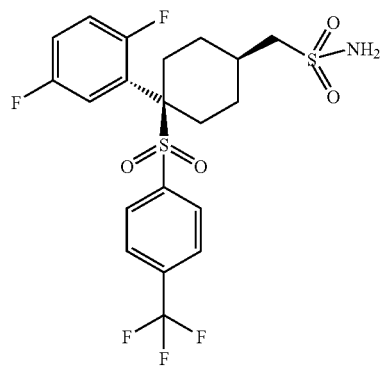

Intermediate M (650 mg, 1.3 mmol) was converted to the corresponding thiol and then to the corresponding sulfonyl chloride by the methods of Intermediate I and Intermediate Q. (Yield 365 mg white solid). This was dissolved in dichloromethane (30 mL) and ammonia gas bubbled into the solution until saturation. The reaction was stirred for a further 30 min before filtering through Celite®. After concentration, the residue was purified by flash chromatography on silica, eluting with iso-hexane/ethyl acetate (1:1), to give the sulfonamide as a white solid (150 mg). $^1$H NMR (CDCl$_3$) δ 1.58–1.68 (2H, m), 2.00–2.04 (2H, m), 2.35–2.43 (2H, m), 2.47–2.49 (3H, m), 3.32 (2H, d, J=6.7 Hz), 4.64 (2H, s), 6.77–6.85 (1H, m), 7.03–7.09 (2H, m), 7.51–7.53 (2H, d, J=7.0 Hz), 7.64–7.67 (2H, d, J=7.0 Hz). MS (ES+) 498 ([MH]$^+$).

Example 3

[4-(4-Chloro-benzenesulfonyl)-4-(2,5-difluoro-phenyl)-cyclohexyl]-methanesulfonamide

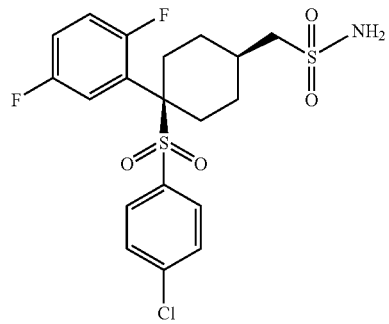

Into a solution of Intermediate Q (41 mg, 0.09 mmol.) in dichloromethane (10 mL) was bubbled ammonia gas for 10 minutes after which time a precipitate had formed. The reaction was diluted with ethyl acetate (20 mL), washed with 2N HCl (2×20 mL) and brine (10 mL), dried (MgSO$_4$) and evaporated to leave a residue which was purified by column chromatography on silica, eluting with ethyl acetate:iso-hexane (1:1), to afford the title compound (24 mg). $^1$H NMR (CDCl$_3$) δ 7.38–7.29 (4H, m), 7.08–7.03 (2H, m), 6.87–6.80

(1H, m), 4.82 (2H, br s), 3.32 (2H, d, J=6.5 Hz), 2.52–2.36 (5H, m), 2.04–1.98 (2H, m) and 1.66–1.56 (2H, m). MS (ES+) 486 ([Mna]+).

The sulfonamides in examples 4–24 were prepared in a similar fashion to 4-(4-chloro-benzenesulfonyl)-4-(2,5-difluoro-phenyl)-cyclohexyl]-methanesulfonamide (Example 3). In cases where a salt of the required amine is used, a base, for example pyridine or potassium carbonate, may be added.

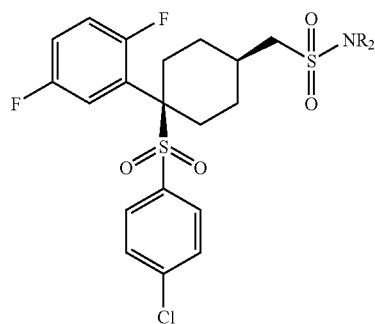

| Example | —NR₂ | MS (ES⁺) |
|---|---|---|
| 4 | cyclobutylamino | 540 ([MNa]⁺) |
| 5 | piperidin-1-yl | 532 ([MH]⁺) |
| 6 | 2-trifluoromethylpyrrolidin-1-yl | 603 ([MNH₄]⁺) |
| 7 | 3,3-difluoropyrrolidin-1-yl | 554 ([MH]⁺) |
| 8 | (R)-3-fluoropyrrolidin-1-yl | 536 ([MH]⁺) |
| 9 | (S)-3-fluoropyrrolidin-1-yl | 536 ([MH]⁺) |
| 10 | 5-aza-2-oxabicyclo[2.2.1]hept-5-yl | 546 ([MH]⁺) |
| 11 | 4,4-difluoropiperidin-1-yl | 585 ([MNH₄]⁺) |
| 12 | N-methoxy-N-methylamino | 530 ([MNa]⁺) |
| 13 | morpholin-4-yl | 534 ([MH]⁺) |
| 14 | pyrrolidin-1-yl | 518 ([MH]⁺) |
| 15 | azetidin-1-yl | 504 ([MH]⁺) |
| 16 | t-butylamino | 537 ([MNH₄]⁺) |
| 17 | 2,2,2-trifluoroethylamino | 568 ([MNa]⁺) |
| 18 | (R)-2-(methoxycarbonyl)pyrrolidin-1-yl | 576 ([MH]⁺) |
| 19 | (S)-2-(methoxycarbonyl)pyrrolidin-1-yl | 576 ([MH]⁺) |
| 20 | t-butoxycarbonylmethylamino | 600 ([MNa]⁺) |
| 21 | hydrazinyl | 479 ([MH]⁺) |
| 22 | dimethylamino | 492 ([MH]⁺) |
| 23 | isopropylamino | 528 ([MNa]⁺) |
| 24 | 3,3-difluoroazetidin-1-yl | 540 ([MH]⁺) |

Example 25

(R)-1-[4-(4-Chloro-benzenesulfonyl)-4-(2,5-difluoro-phenyl)-cyclohexylmethanesulfonyl]-pyrrolidine-2-carboxylic acid

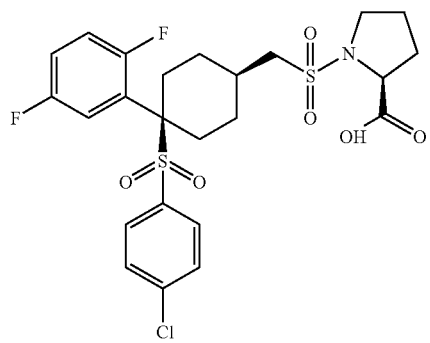

To a stirred solution of (R)-1-[4-(4-chloro-benzenesulfonyl)-4-(2,5-difluoro-phenyl)-cyclohexylmethanesulfonyl]-pyrrolidine-2-carboxylic acid methyl ester (Example 18) (108 mg, 0.19 mmol.) in tetrahydrofuran (10 mL) was added lithium hydroxide (18 mg) in water (4 mL) and the mixture vigorously stirred for 1.5 hours. After removal of the solvent in vacuo, the aqueous residue was acidified to pH 1 with 2N aqueous hydrochloric acid and extracted with ethyl acetate (2×10 mL). The combined organic layers were washed with brine (10 mL), dried (MgSO₄) and evaporated to leave a residue which was purified by column chromatography on silica, eluting with ethyl acetate:dichloromethane:acetic acid (30:60:1), to afford the desired MS (ES+) 562 ([MH]⁺).

Example 26

(S)-1-[4-(4-Chloro-benzenesulfonyl)-4-(2,5-difluoro-phenyl)-cyclohexylmethanesulfonyl]-pyrrolidine-2-carboxylic acid

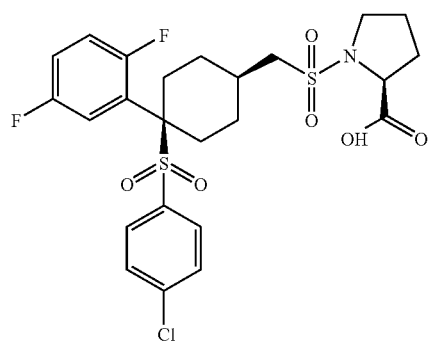

Prepared from (S)-1-[4-(4-chloro-benzenesulfonyl)-4-(2,5-difluoro-phenyl)-cyclohexylmethanesulfonyl]-pyrrolidine-2-carboxylic acid methyl ester (Example 19) by the procedure of Example 25.

MS (ES+) 562 ([MH]⁺).

Example 27

[4-(4-Chloro-benzenesulfonyl)-4-(2,5-difluoro-phenyl)-cyclohexylmethanesulfonylamino]-acetic acid

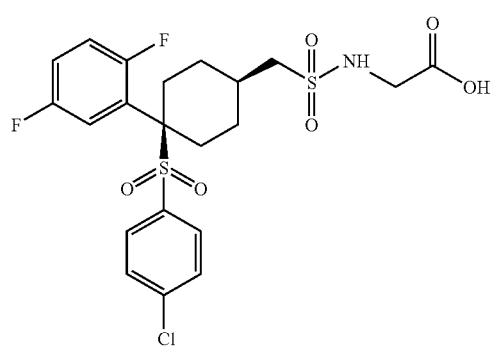

To a stirred solution of [4-(4-chloro-benzenesulfonyl)-4-(2,5-difluoro-phenyl)-cyclohexylmethanesulfonylamino]-acetic acid tert-butyl ester (Example 20) (80 mg) in dichloromethane (10 mL) was added trifluoroacetic acid (2 mL)

and the reaction stirred for 3 hours then evaporated. Purification by column chromatography on silica, eluting with ethyl acetate:dichloromethane:acetic acid (75:25:1), afforded the desired product. MS (ES+) 522 ([MH]+).

Example 28

N-Acetyl-C-[4-(4-chloro-benzenesulfonyl)-4-(2,5-difluoro-phenyl)-cyclohexyl]-methanesulfonamide

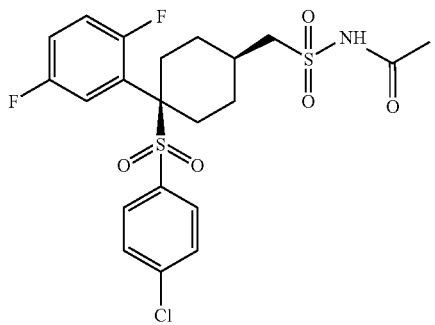

To a stirred solution of [4-(4-chloro-benzenesulfonyl)-4-(2,5-difluoro-phenyl)-cyclohexyl]-methanesulfonamide (Example 3) (64 mg, 0.14 mmol.), acetic acid (0.011 mL, 0.17 mmol.) and dimethylaminopyridine (20 mg, 0.17 mmol.) in dichloromethane was added 1-(3-dimethylaminopropyl)-3-ethylcarbodiimide hydrochloride (32 mg, 0.17 mmol.) and the mixture stirred at ambient temperature for 18 hours. After dilution with ethyl acetate (25 mL), and washing with 2N aqueous hydrochloric acid (20 mL) and brine (20 mL), drying (MgSO$_4$) and evaporation left a residue which was purified by column chromatography on silica, eluting with ethyl acetate:dichloromethane:iso-hexane (2:1:1), to afford the desired product.

MS (ES+) 528 ([MNa]+).

Example 29

Acetic acid 1-[4-(4-chloro-benzenesulfonyl)-4-(2,5-difluoro-phenyl)-cyclohexylmethanesulfonyl]-azetidin-3-yl ester

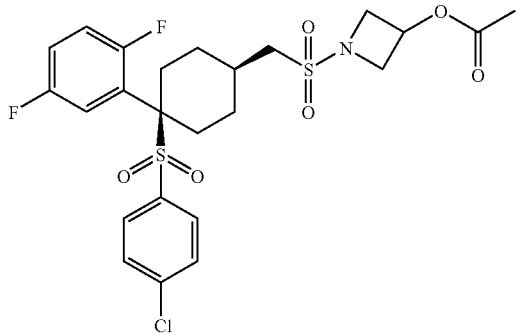

To a stirred solution of N-benzhydryl-azetidin-3-ol (3.56 g, 14.9 mmol.) in dichloromethane (60 mL) was added acetic anhydride (2.1 mL, 22.4 mmol.), triethylamine (3.1 mL, 22.4 mmol.) and dimethylaminopyridine (ca. 10 mg). The mixture was stirred for 3 hours then diluted with ethyl acetate (200 mL) and washed with saturated aqueous ammonium chloride solution (100 mL), 1N aqueous sodium hydroxide (100 mL) and brine (100 mL), dried (MgSO$_4$) and evaporated to leave N-benzhydryl-3-acetoxy-azetidine (4.2 g) which was used without further purification.

The acetate from the foregoing step (4.2 g) was dissolved in a mixture of methanol (100 mL) and 2N aqueous hydrochloric acid (10 mL). Palladium hydroxide (20%, moist on charcoal, 1.0 g) was added and the mixture hydrogenated on a Parr hydrogenator at a hydrogen pressure of 50 psi for 18 hours. The mixture was filtered through a bed of Celite®, washing the bed well with further methanol then the filtrate was evaporated to a pale purple oil. Ether (100 mL) was added and the mixture stirred for 5 minutes. The ether was decanted and the ether wash repeated. The oil was azeotroped with toluene (2×25 mL) to leave 3-acetoxy azetidine hydrochloride (2.2 g) as a viscous oil which crystallized on standing.

The 3-acetoxy azetidine hydrochloride (900 mg) was partitioned between dichloromethane (20 ml) and 2N aqueous sodium hydroxide (5 mL), and the dichloromethane layer added to a solution of Intermediate Q (276 mg, 0.57 mmol.) in dichloromethane (5 mL). The mixture was stirred for 7 hours then diluted with further dichloromethane (50 mL) and washed with 2N aqueous hydrochloric acid (20 mL) and brine (20 mL), dried (MgSO$_4$) and evaporated to leave a residue which was purified by column chromatography on silica, eluting with ethyl acetate:dichloromethane:iso-hexane (1:1:3), to afford the desired product (204 mg).

$^1$H NMR (CDCl$_3$) δ 7.38–7.29 (4H, m), 7.07–7.02 (2H, m), 6.86–6.82 (1H, m), 5.16 (1H, m), 4.18 (2H, dd, J=9.0, 7.0 Hz), 4.01 (2H, dd, J=9.0, 5.0 Hz), 3.09 (2H, d, J=6.5 Hz), 2.50–2.32 (5H, m), 2.11 (3H, s), 1.99–1.93 (2H, m) and 1.64–1.57 (2H, m). MS (ES+) 562 ([MH]+).

Example 30

1-[4-(4-Chloro-benzenesulfonyl)-4-(2,5-difluoro-phenyl)-cyclohexylmethanesulfonyl]-azetidin-3-ol

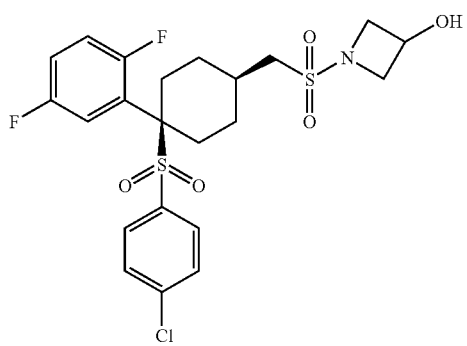

To a stirred solution of acetic acid 1-[4-(4-chloro-benzenesulfonyl)-4-(2,5-difluoro-phenyl)-cyclohexylmethanesulfonyl]-azetidin-3-yl ester (Example 29) (185 mg, 0.33 mmol.) in tetrahydrofuran (10 mL) was added a solution of lithium hydroxide (16 mg, 0.67 mmol.) in water (5 mL) and the mixture stirred for 45 minutes. The solvent was removed in vacuo and the residue diluted with 1N aqueous sodium hydroxide (10 mL) and extracted into ethyl acetate (2×20 mL). The combined organic layers were washed with brine (20 mL), dried (MgSO$_4$) and evaporated to leave the desired compound (171 mg).

MS (ES+) 520 ([MH]$^+$).

Example 31

1-[4-(4-Chloro-benzenesulfonyl)-4-(2,5-difluoro-phenyl)-cyclohexylmethanesulfonyl]-azetidin-3-one

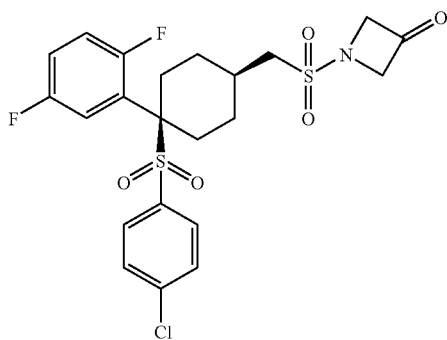

To a stirred solution of 1-[4-(4-chloro-benzenesulfonyl)-4-(2,5-difluoro-phenyl)-cyclohexylmethanesulfonyl]-azetidin-3-ol (Example 30) (143 mg, 0.28 mmol.) in dichloromethane (10 mL) was added Dess-Martin periodinane (230 mg, 0.56 mmol.) and the mixture stirred at ambient temperature for 18 hours. Ethyl acetate (20 mL) was added and the solution washed with 10% sodium thiosulfate solution (20 mL), water (20 mL) and brine (20 mL), dried (MgSO$_4$) and evaporated to leave a residue which was purified by column chromatography on silica, eluting with ethyl acetate:dichloromethane:iso-hexane (1:1:2), to afford the desired product (98 mg).

MS (ES+) 535 ([MNH$_4$]+).

Example 32

1-[4-(4-Chloro-benzenesulfonyl)-4-(2,5-difluoro-phenyl)-cyclohexylmethanesulfonyl]-3-methyl-azetidin-3-ol

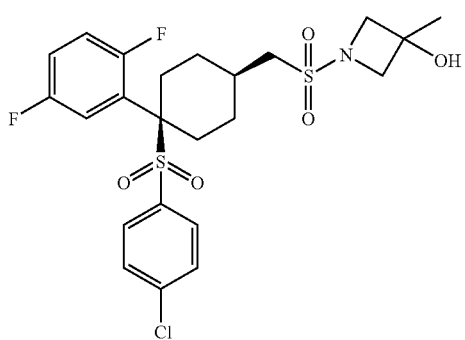

To a stirred solution of 1-[4-(4-chloro-benzenesulfonyl)-4-(2,5-difluoro-phenyl)-cyclohexylmethanesulfonyl]-azetidin-3-one (Example 31) (58 mg, 0.11 mmol.) in tetrahydrofuran (5 mL) was added a solution of methyl magnesium bromide (3M in diethyl ether, 0.075 mL, 0.22 mmol.) and the mixture stirred at ambient temperature for 45 minutes. The reaction was quenched by the addition of saturated aqueous ammonium chloride (10 mL) and the mixture extracted with ethyl acetate (2×20 mL). The combined organic layers were washed with water (20 mL) and brine (20 mL), dried (MgSO$_4$) and evaporated to leave a residue which was purified by column chromatography on silica, eluting with ethyl acetate:dichloromethane:iso-hexane (1:1:1), to afford the desired product (51 mg).

MS (ES+) 534 ([MH]$^+$).

Example 33

Methanesulfonic acid 1-[4-(4-chloro-benzenesulfonyl)-4-(2,5-difluoro-phenyl)-cyclohexylmethanesulfonyl]-azetidin-3-yl ester

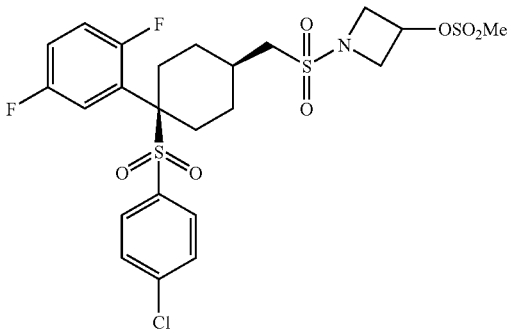

To a stirred solution of 1-[4-(4-chloro-benzenesulfonyl)-4-(2,5-difluoro-phenyl)-cyclohexylmethanesulfonyl]-azetidin-3-ol (Example 30) (180 mg, 0.35 mmol) in dichloromethane (10 mL) at 0° C. was added triethylamine (0.08 mL, 0.58 mmol) and methanesulfonyl chloride (0.035 mL, 0.45 mmol) and the mixture stirred 2 hours at 0° C. Ethyl acetate (20 mL) was added and the mixture washed with 2N aqueous hydrochloric acid (20 μL) and brine (20 mL), dried (MgSO$_4$) and evaporated to leave a residue which was purified by column chromatography on silica, eluting with ethyl acetate:iso-hexane (1:1), to afford the desired product (162 mg).

MS (ES+) 598 ([MH]$^+$).

Example 34

2-[4-(4-Chloro-benzenesulfonyl)-4-(2,5-difluoro-phenyl)-cyclohexylmethylsulfanyl]-pyridine

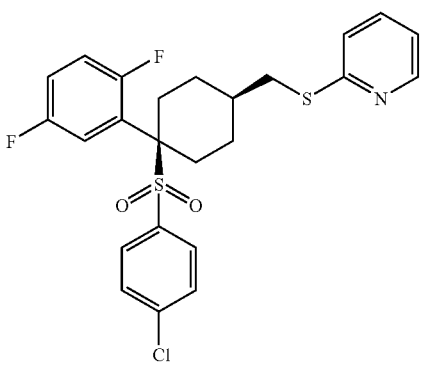

To a stirred solution of Intermediate E (150 mg, 0.29 mmol) in ethanol (10 mL) under nitrogen was added potassium hydroxide (18 mg, 0.32 mmol) and 2-mercaptopyridine (36 mg, 0.32 mmol). The mixture was stirred and heated to reflux for 16 hours. After cooling, the reaction was diluted with water and extracted with ethyl acetate. The combined organic layers were washed with water and brine, dried (MgSO$_4$) and evaporated to leave a residue (154 mg) which was purified by preparative thin layer chromatography eluting with ethyl acetate:iso-hexane 1:6 to afford the desired product (118 mg).

$^1$H NMR (CDCl$_3$) δ 8.42–7.8.41 (1H, m), 7.48–7.44 (1H, m), 7.38–7.33 (4H, m), 7.18–7.16 (1H, d, J=8.1 Hz), 7.10–6.95 (2H, m), 6.86–6.79 (1H, m), 3.36–3.34 (2H, d, J=7.4 Hz), 2.47–2.46 (4H, m), 1.95–1.90 (3H, m), 1.58–1.50 (3H, m). MS (ES+) 494 ([MH]$^+$), 318 ([M-ArSO$_2$—]+).

Example 35

2-[4-(4-Chloro-benzenesulfonyl)-4-(2,5-difluoro-phenyl)-cyclohexylmethanesulfonyl]-pyridine

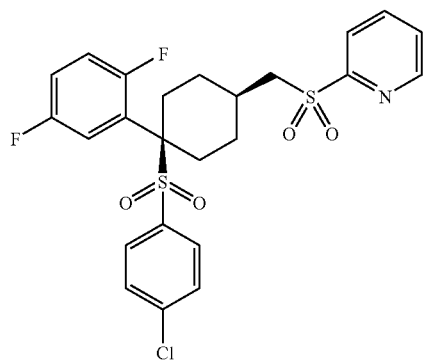

To a stirred solution of the product from Example 34 (40 mg, 0.081 mmol) in dichloromethane (10 mL) under nitrogen was added 3-chloroperoxybenzoic acid (62 mg, 50–55% w/w in water, 0.18 mmol). The mixture was stirred at ambient temperature for 18 h. The reaction was diluted with dichloromethane, washed with sodium sulfite solution and brine, dried (MgSO$_4$) and evaporated to afford the desired product (56 mg).

$^1$H NMR (CDCl$_3$) δ 8.71–8.70 (1H, d, J=4.0 Hz), 8.04–8.02 (1H, d, J=7.7 Hz), 7.94–7.89 (1H, t, J=7.6 Hz), 7.52–7.49 (1H, m), 7.30–7.20 (4H, m), 6.99–6.94 (2H, m), 6.79–6.73 (1H, m), 3.49–3.47 (2H, d, J=6.4 Hz), 2.39–2.27 (5H, m), 1.90–1.87 (2H, d, J=12.7 Hz), and 1.55–1.43 (2H, m). MS (ES+) 526 ([MH]$^+$), 350 ([M-ArSO$_2$—]$^+$), 548 ([MNa]$^+$).

Example 36

2-[4-(4-Chloro-benzenesulfonyl)-4-(2,5-difluoro-phenyl)-cyclohexylmethanesulfinyl]-pyridine

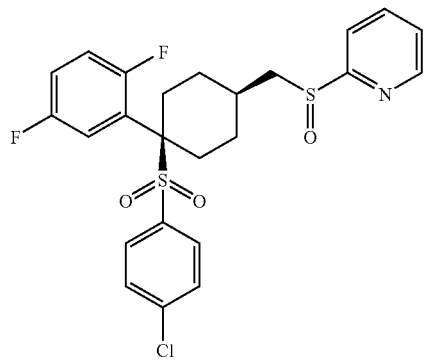

To a stirred solution of the product from Example 34 (31 mg, 0.07 mmol) in dichloromethane (10 mL) under nitrogen was added 3-chloroperoxybenzoic acid (11 mg, 50–55% w/w in water, 0.07 mmol). The mixture was stirred at ambient temperature for 3.5 h, then diluted with dichloromethane, washed with sodium sulfite solution and brine, dried (MgSO$_4$) and evaporated to leave a residue (20 mg) which was purified by preparative thin layer chromatography eluting with ethyl acetate:iso-hexane 1:1 to afford the desired product (12 mg).

$^1$H NMR (CDCl$_3$) δ 8.02–8.66 (1H, d, J=4.5 Hz), 8.02–7.93 (2H, m), 7.43–7.39 (3H, m), 7.38–7.27 (2H, m), 7.08–7.02 (2H, m), 6.87–6.80 (1H, m), 3.36–3.30 (1H, m), 2.91–2.85 (1H, dd, J=13.4, 4.9 Hz), 2.51–2.32 (5H, m), 2.11–2.04 (1H, m), 1.75–1.55 (1H, m), and 1.55–1.43 (2H, m).

MS (ES+) 510 ([MH]$^+$), 334 ([M-ArSO$_2$—]$^+$), 532 ([MNa]$^+$).

Example 37

1-(4-Chlorophenylsulfonyl)-1-(2,5-difluoro-phenyl)-4-[(2-methyl-2-propyl)sulfonylmethyl]-cyclohexane

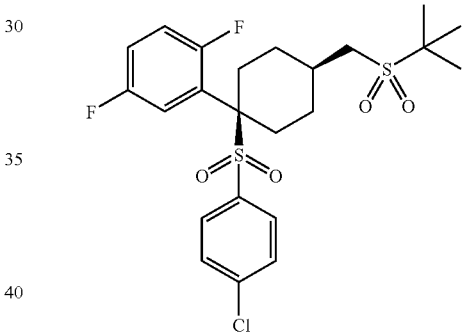

To a stirred solution of Intermediate E (100 mg, 0.20 mmol) in ethanol (10 mL) under nitrogen was added sodium-2-methyl-2-propanethiolate (29 mg of 90% purity, 0.24 mmol). The mixture was stirred and heated to reflux for 90 minutes, then cooled, diluted with water and extracted with ethyl acetate. The combined organic layers were washed with water, 2N aqueous sodium hydroxide and brine, dried (MgSO$_4$) and evaporated to give the sulfide intermediate (100 mg) which was dissolved in dichloromethane (10 mL) and treated with 3-chloroperoxybenzoic acid (196 mg of 50–55% in water, 1.19 mmol). After stirring at ambient temperature for 16 h. the mixture was diluted with ethyl acetate, washed with sodium sulfite and 2N aqueous sodium hydroxide, dried (MgSO$_4$) and evaporated to leave a residue (60 mg) which was purified by preparative thin layer chromatography eluting with ethyl acetate:iso-hexane 1:3 to give the desired product (38 mg).

$^1$H NMR (CDCl$_3$) δ 7.37–7.29 (4H, m), 7.07–7.02 (2H, m), 6.87–6.80 (1H, m), 3.02–3.00 (2H, d, J=6.5 Hz), 2.56–2.52 (2H, m), 2.46–2.43 (3H, m), 2.04–1.99 (2H, m), 1.72–1.64 (2H, m) and 1.44 (9H, s). MS (ES+) 527 ([MNa]$^+$), 522 ([MNH4]+).

Example 38

2-[4-(4-Chloro-benzenesulfonyl)-4-(2,5-difluoro-phenyl)-cyclohexylmethanesulfonyl]-pyridine-N-oxide

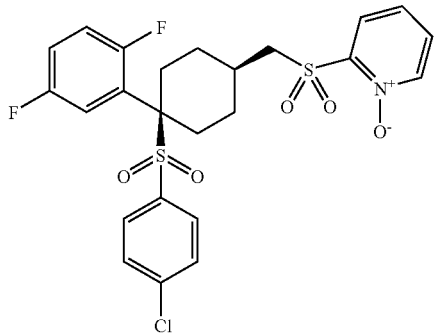

To a stirred solution of the product from Example 35 (35 mg, 0.07 mmol) in dichloromethane (10 mL) under nitrogen was added urea hydrogen peroxide (12.5 mg, 0.13 mmol). The reaction mixture was cooled to 0° C. and trifluoroacetic anhydride (19 μL, 0.13 mmol) added dropwise. The reaction mixture was stirred and left to warm to ambient temperature over 16 h., quenched with sodium sulfite solution, diluted with water, extracted with dichloromethane, washed with brine, dried (MgSO$_4$) and evaporated to leave a residue (16 mg) which was purified by preparative thin layer chromatography eluting with ethyl acetate to afford the desired product (8 mg).

$^1$H NMR (CDCl$_3$) 8.29–8.28 (1H, d, J=6.0 Hz), 8.10–8.08 (1H, dd, J=8.0, 2.0 Hz), 7.55–7.51 (1H, m), 7.46–7.42 (1H, m), 7.38–7.30 (4H, m), 7.06–7.00 (2H, m), 6.86–6.79 (1H, m), 3.88–3.87 (2H, d, J=6.6 Hz), 2.51–2.36 (5H, m), 2.04–1.97 (2H, m) and 1.66–1.62 (2H, m). MS (ES+) 542 ([MH]$^+$), 366 ([M-ArSO$_2$—]$^+$).

Example 39

1-(4-Chlorophenylsulfonyl)-1-(2,5-difluoro-phenyl)-4-[(2-propyl)sulfonylmethyl]-cyclohexane

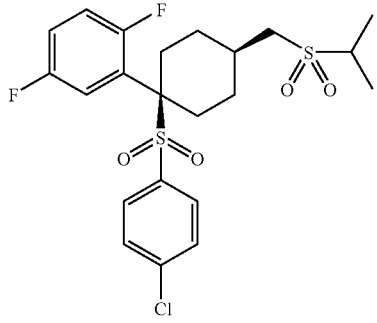

To a stirred solution of Intermediate E (150 mg, 0.29 mmol) in ethanol (10 mL) under nitrogen was added potassium hydroxide (18 mg, 0.32 mmol) and 2-propanethiol (30 μL, 0.32 mmol). The mixture was stirred and heated to reflux for 4 hours, cooled, diluted with water and extracted with ethyl acetate. The combined organic layers were washed with water and brine, dried (MgSO$_4$) and evaporated to leave a residue which was diluted in ethyl acetate (1 mL), added to a stirring solution of sodium periodate (139 mg, 0.65 mmol) in a 1:2 solution of ethyl acetate:water (3 mL) and a catalytic amount of ruthenium(IV) oxide. The reaction mixture turned black on the addition of the sulfide solution and was stirred at ambient temperature over 30 min., diluted with water, extracted with ethyl acetate, washed with brine, dried (MgSO$_4$) and evaporated to give a residue (135 mg) which was purified by preparative thin layer chromatography eluting with ethyl acetate:iso-hexane 1:3 to afford the desired product (39 mg).

$^1$H NMR (CDCl$_3$) δ 7.34–7.29 (4H, m), 7.07–7.02 (2H, m), 6.87–6.81 (1H, m), 3.14–3.04 (1H, m), 3.04–3.02 (2H, d, J=6.7 Hz), 2.52–2.38 (5H, m), 2.03–1.98 (2H, m), 1.71–1.61 (2H, m) and 1.44–1.42 (6H, d, J=6.9 Hz). MS (ES+) 513 ([MNa]$^+$), 508 ([MNH$_4$]$^+$).

Examples 40 to 57 were prepared from Intermediate E and appropriate thiols by the method of Example 39, and Examples 58 to 61 were prepared from Intermediate E and appropriate thiols by the methods of Examples 34 and 35.

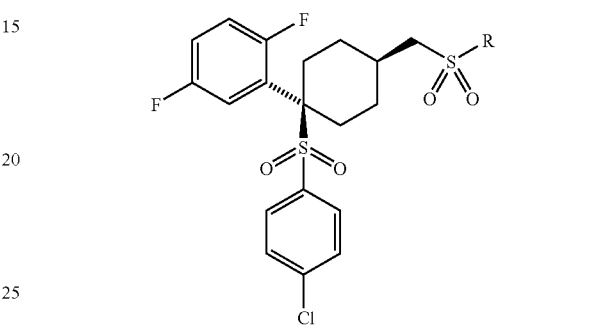

| Example | R | MS (ES+) |
|---|---|---|
| 40 | 2,2,2-trifluoroethyl | 548 ([MNH$_4$]$^+$), 553 ([MNa]$^+$) |
| 41 | n-propyl | 508 ([MNH$_4$]$^+$) |
| 42 | 2-methylpropyl | 522 ([MNH$_4$]$^+$), 527 ([MNa]$^+$) |
| 43 | 4-pyridyl | 350 ([M-ArSO$_2^-$]$^+$), 526 ([MH]$^+$), 548 ([MNa]$^+$) |
| 44 | 2-pyrimidinyl | 351 ([M-ArSO$_2^-$]$^+$), 527 ([MH]$^+$) |
| 45 | 4-methyl-2-thiazolyl | 370 ([M-ArSO$_2^-$]$^+$), 546 ([MH]$^+$), 568 ([MNa]$^+$) |
| 46 | 5-methyl-[1,3,4]thiadiazol-2-yl | 371 ([M-ArSO$_2^-$]$^+$), 547 ([MH]$^+$), 569 ([MNa]$^+$) |
| 47 | 2-methyl-3-furyl | 546 ([MNH$_4$]$^+$), 551 ([MNa]$^+$) |
| 48 | —CH$_2$COCH$_3$ | 527 ([MNa]$^+$) |
| 49 | 2-furylmethyl | 546 ([MNH$_4$]$^+$), 551 ([MNa]$^+$) |
| 50 | 1-(2-thienyl)ethyl | 576 ([MNH$_4$]$^+$), 581 ([MNa]$^+$) |
| 51 | benzyl | 556 ([MNH$_4$]$^+$), 561 ([MNa]$^+$) |
| 52 | cyclopentyl | 517 ([MH]$^+$), 534 ([MNH$_4$]$^+$), 539 ([MNa]$^+$) |
| 53 | 2-thiazolyl | 356 ([M-ArSO$_2^-$]$^+$), 554 ([MNa]$^+$) |
| 54 | cyclohexyl | 531 ([MH]$^+$), 548 ([MNH$_4$]$^+$), 553 ([MNa]$^+$) |
| 55 | 2-thienyl | 548 ([MNH$_4$]$^+$), 553 ([MNa]$^+$) |
| 56 | 1-methyl-1H-imidazol-2-yl | 353 ([M-ArSO$_2^-$]$^+$), 529 ([MH]$^+$) |
| 57 | 4-methyl-4H-[1,2,4]triazol-3-yl | 354 ([M-ArSO$_2^-$]$^+$), 530 ([MH]$^+$), 552 ([MNa]$^+$) |
| 58 | 2-hydroxyethyl | 493 ([MH]$^+$), 515 ([MNa]$^+$) |
| 59 | 1H-imidazol-2-yl | 339 ([M-ArSO$_2^-$]$^+$), 515 ([MH]$^+$) |
| 60 | 1-methyl-1H-tetrazole-5-yl | 335 ([M-ArSO$_2^-$]$^+$), 531 ([MH]$^+$), 553 ([MNa]$^+$) |

-continued

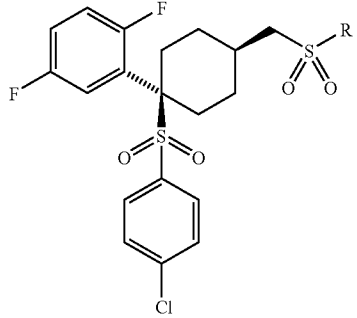

| Example | R | MS (ES+) |
|---|---|---|
| 61 | 1H-[1,2,4]triazol-3-yl | 340 ([M-ArSO$_2^-$]$^+$), 516 ([MH]$^+$), 538 ([MNa]$^+$) |

Example 62

5-[4-(4-Chloro-benzenesulfonyl)-4-(2,5-difluoro-phenyl)-cyclohexylmethanesulfonyl]-1-methyl-1H-tetrazole

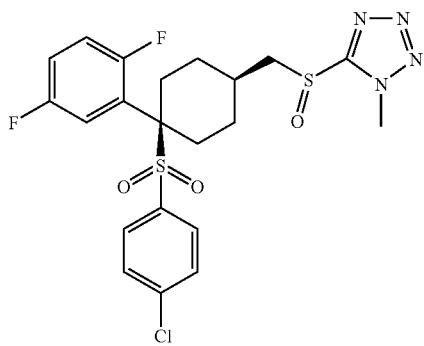

Prepared from Intermediate E by the procedures of Examples 34 and 36.

MS (ES+) 339 ([M-ArSO$_2^-$]$^+$), 515 ([MH]$^+$), 537 ([MNa]$^+$).

Example 63

1-[4-(4-Chloro-benzenesulfonyl)-4-(2,5-difluoro-phenyl)-cyclohexylmethanesulfonyl]-2-methyl-propan-2-ol

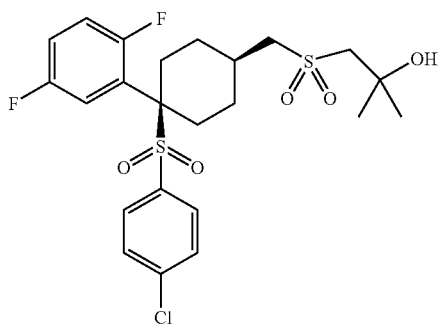

To a stirred solution of Intermediate E (300 mg, 0.59 mmol) in ethanol (10 mL) under nitrogen was added potassium hydroxide (40 mg, 0.71 mmol) and 2-mercaptoethyl acetate (77 µL, 0.71 mmol). The mixture was stirred and heated to reflux for 16 hours, then cooled, diluted with water and extracted with ethyl acetate. The combined organic layers were washed with water and brine, dried (MgSO$_4$) and evaporated to leave a residue (320 mg) which was purified by preparative thin layer chromatography eluting with ethyl acetate:iso-hexane 1:6 to afford the sulfide intermediate (186 mg).

$^1$H NMR (CDCl$_3$) δ 7.38–7.31 (4H, m), 7.09–7.01 (2H, m), 6.87–6.80 (1H, m), 4.23–4.17 (2H, q, J=7 Hz), 3.20 (2H, s), 2.80–2.78 (2H, d, J=7.6 Hz), 2.46–2.33 (4H, m), 1.91–1.87 (3H, m), 1.57–1.49 (2H, m), 1.32–1.28 (3H, t, J=7 Hz).

To a stirred solution of the sulfide from the foregoing step (91.5 mg, 0.18 mmol) in tetrahydrofuran under nitrogen was added dropwise methylmagnesium bromide (0.24 mL of 3M ethereal solution, 0.73 mmol) at ambient temperature. The reaction mixture was stirred at ambient temperature for 3 h., quenched with water, extracted with ethyl acetate, washed with brine, dried (MgSO$_4$) and evaporated to afford the gem-dimethyl alcohol (90 mg). This was treated with a solution of 3-chloroperoxybenzoic acid (157 mg of 50–55% in water, 0.92 mmol) in dichloromethane (10 mL), stirred at ambient temperature for 16 h, diluted with sodium sulfite and extracted with dichloromethane. The extracts were washed with brine, dried (MgSO$_4$) and evaporated to yield a residue which was purified by preparative thin layer chromatography eluting with 1:1 ethyl acetate:isohexane to afford the desired product (17.5 mg).

$^1$H NMR (CDCl$_3$) δ 7.38–7.29 (4H, m), 7.07–7.02 (2H, m), 6.86–6.83 (1H, m), 3.24–3.17 (4H, m), 2.48–2.36 (5H, m), 2.01–1.97 (2H, m), 1.67–1.62 (2H, m) and 1.48 (6H, s). MS (ES+) 538 ([MNH$_4$]$^+$), 543 ([MNa]$^+$).

Example 64

1-(4-Chlorophenylsulfonyl)-1-(2,5-difluoro-phenyl)-4-[(2-methoxyethyl)sulfonylmethyl]-cyclohexane

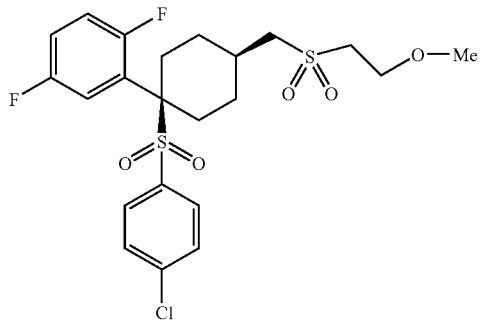

To a stirred solution of Intermediate E (200 mg, 0.39 mmol) in ethanol (10 mL) under nitrogen was added potassium hydroxide (33 mg, 0.59 mmol) and 2-mercaptoethanol (42 µL, 0.59 mmol). The mixture was stirred and heated to reflux for 16 hours., then cooled, diluted with water and extracted with ethyl acetate. The combined organic layers were washed with water and brine, dried (MgSO$_4$) and evaporated to leave a residue (199 mg) which was dissolved in N,N-dimethylformamide (20 mL) under nitrogen and treated with sodium hydride (31 mg of a 60% dispersion in mineral oil, 0.78 mmol) and iodomethane (49 µL, 0.78 mmol). The resulting mixture was stirred at ambient temperature for 5 h then diluted with ethyl acetate, washed with 2N aqueous sodium hydroxide, dried and evaporated to yield the sulfide intermediate (150 mg).

$^1$H NMR (CDCl$_3$) δ 7.38–7.29 (4H, m), 7.09–7.01 (2H, m), 6.87–6.80 (1H, m), 3.58–3.54 (2H, t, J=6.6 Hz), 3.37

(3H, s), 2.73–2.68 (4H, m), 2.46–2.33 (4H, m), 1.92–1.87 (2H, m), 1.80–1.76 (3H, m), 1.57–1.48 (2H, m).

To a stirred solution of the sulfide from the foregoing step (150 mg, 0.32 mmol) in dichloromethane (10 mL) was added 3-chloroperoxybenzoic acid (273 mg of 50–55% in water, 0.79 mmol). The reaction mixture was stirred at ambient temperature for 16 h, then diluted with sodium sulfite, extracted with ethyl acetate, washed with brine, dried (MgSO$_4$) and evaporated to give a residue which was purified by preparative thin layer chromatography eluting with ethyl acetate:isohexane 1:3 to afford the desired product (100 mg).

$^1$H NMR (CDCl$_3$) δ 7.41–7.28 (4H, m), 7.08–7.03 (2H, m), 6.88–6.82 (1H, m), 3.85–3.81 (2H, t, J=5.4 Hz), 3.41 (3H, s), 3.29–3.19 (4H, m), 2.48–2.35 (5H, m), 2.00–1.96 (2H, m) and 1.66–1.58 (2H, m). MS (ES+) 507 ([MH]$^+$), 524 ([MNH$_4$]$^+$), 529 ([MNa]$^+$).

Example 65

1-(4-Chlorophenylsulfonyl)-1-(2,5-difluoro-phenyl)-4-(cyclopropylsulfonylmethyl)-cyclohexane

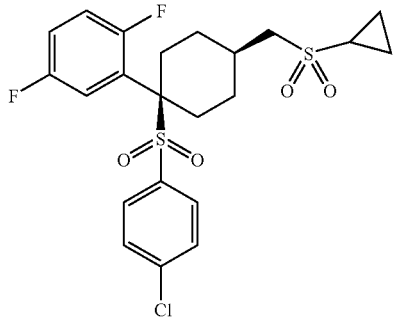

To a suspension of magnesium turnings (183 mg, 7.51 mmol) in tetrahydrofuran (2 mL) under nitrogen at 0° C. was slowly added cyclopropyl bromide (1 g, 8.3 mmol). The reaction mixture was warmed to 50° C. for 3 h, cooled to 0° C., and sulfur flowers (198 mg, 6.2 mmol) added in small portions. The reaction mixture was heated to 50° C. for 3 h, then cooled to 0° C. and treated dropwise with lithium aluminium hydride (4.3 mL of 1.0M solution in tetrahydrofuran, 4.30 mmol). The resulting mixture was heated to reflux and stirred for 30 min., cooled to 0° C., and treated slowly with water (1 mL), aqueous sulfuric acid (6 mL) and diethyl ether (10 mL). The layers were separated and the aqueous layer was extracted with further diethyl ether. The combined organic extracts were washed with 5% aqueous sufuric acid (10 mL), 5% aqueous sodium carbonate (100 mL), saturated aqueous ammonium chloride (10 mL) and brine and dried (MgSO$_4$) to give a diethyl ether/tetrahydrofuran solution of cyclopropane thiol in 30–40% conversion from cyclopropyl bromide.

To a stirred solution of Intermediate E (100 mg, 0.20 mmol) in ethanol (10 mL) under nitrogen was added potassium hydroxide (55 mg, 0.98 mmol) and cyclopropane thiol (5.8 mL of 0.17M in diethyl ether/tetrahydrofuran solution, 0.98 mmol). The mixture was stirred and heated to reflux for 16 hours, then cooled, diluted with water and extracted with ethyl acetate. The combined organic layers were washed with water and brine, dried (MgSO$_4$) and evaporated to leave the sulfide residue which was dissolved in dichloromethane (10 mL) and treated with 3-chloroperoxybenzoic acid (169 mg of 50–55% in water, 0.49 mmol). The reaction mixture was stirred at ambient temperature for 16 h, diluted with sodium sulfite, extracted with ethyl acetate, washed with brine, dried (MgSO$_4$) and evaporated to give a residue which was purified by preparative thin layer chromatography eluting with ethyl acetate:isohexane 1:3 to afford the desired product (24 mg).

$^1$H NMR (CDCl$_3$) δ 7.44–7.29 (4H, m), 7.07–7.03 (2H, m), 6.87–6.80 (1H, m), 3.20–3.19 (2H, d, J=6.6 Hz), 2.52–2.38 (6H, m), 2.03–1.98 (2H, m), 1.69–1.59 (2H, m), 1.30–1.26 (2H, m) and 1.10–1.05 (2H, m). MS (ES+) 511 ([MNa]$^+$).

Example 66

3-[4-(4-Chloro-benzenesulfonyl)-4-(2,5-difluoro-phenyl)-cyclohexylmethanesulfonyl]-1-methyl-1H-[1,2,4]triazole

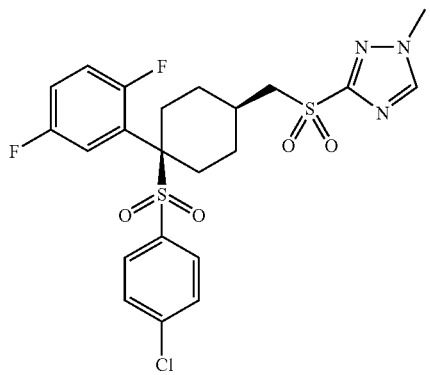

A stirred solution of the product from Example 61 (20 mg, 0.04 mmol) in N,N-dimethylformamide (0.5 mL) was treated under nitrogen with potassium carbonate (35 mg, 0.25 mmol) and iodomethane (20 μL, 0.25 mmol). The mixture was stirred at ambient temperature for 16 h then diluted with water and extracted with ethyl acetate. The combined organic layers were washed several times with water, dried (MgSO$_4$) and evaporated to give a mixture of two isomers which was purified by preparative thin layer chromatography on silica, eluting with ethyl acetate:isohexane 1:1, the title compound being the more polar component.

$^1$H NMR (CDCl$_3$) δ 7.94 (1H, s), 7.38–7.30 (4H, m), 7.07–7.02 (2H, m), 6.87–6.82 (1H, m), 4.21 (3H, s), 3.71–3.69 (2H, d, J=6.5 Hz), 2.49–2.43 (5H, m), 2.04–1.98 (2H, m) and 1.69–1.61 (2H, m). MS (ES+) 354 ([M-ArSO$_2$$^-$]$^+$), 530 ([MH]$^+$), 552 ([MNa]$^+$).

Example 67

5-[4-(4-Chloro-benzenesulfonyl)-4-(2,5-difluoro-phenyl)-cyclohexylmethanesulfonyl]-1-methyl-1H-[1,2,4]triazole

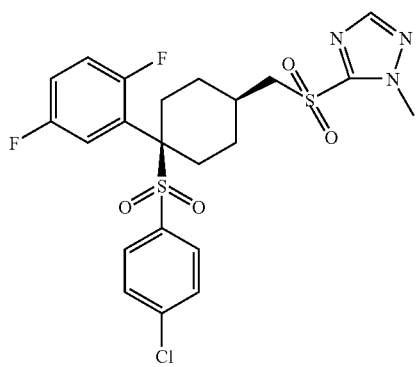

Isolated by preparative TLC of the product mixture of Example 66 as the less polar component.

$^1$H NMR (CDCl$_3$) δ 8.20 (1H, s), 7.38–7.29 (4H, m), 7.06–7.01 (2H, m), 6.87–6.80 (1H, m), 4.06 (3H, s), 3.51–3.49 (2H, d, J=6.5 Hz), 2.51–2.33 (5H, m), 1.99–1.95 (2H, m) and 1.66–1.61 (2H, m). MS (ES+) 354 ([M-ArSO$_2^-$]$^+$), 530 ([MH]$^+$), 552 ([MNa]$^+$).

Example 68

1-(4-Chlorophenylsulfonyl)-1-(2,5-difluoro-phenyl)-4-(cyclobutylsulfonylmethyl)-cyclohexane

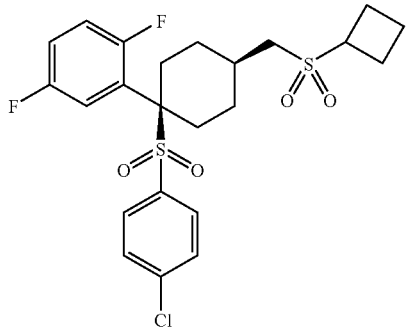

Prepared by the method of Example 65, using cyclobutyl bromide.

$^1$H NMR (CDCl$_3$) δ 7.38–7.29 (4H, m), 7.07–7.02 (2H, m), 6.87–6.80 (1H, m), 3.81–3.72 (1H, m), 2.95–2.93 (2H, d, J=6.6 Hz), 2.65–2.27 (9H, m), 2.11–1.96 (4H, m) and 1.68–1.59 (2H, m). MS (ES+) 327 ([M-ArSO$_2^-$]$^+$), 525 ([MNa]$^+$).

Example 69

[4-(4-Chloro-benzenesulfonyl)-4-(2,5-difluoro-phenyl)-cyclohexylmethylsulfanyl]-acetic acid ethyl ester

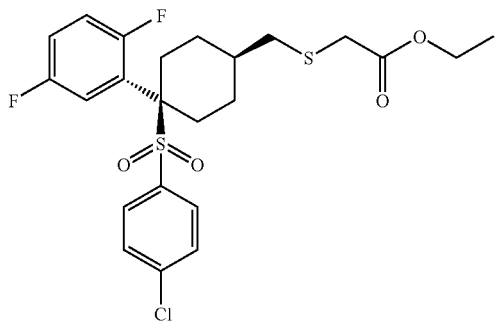

To Intermediate E (100 mg, 0.18 mmol) in ethanol (5 mL) were added ethyl 2-mercaptoacetate (25 µL, 0.2 mmol) and ground potassium hydroxide (12 mg, 0.2 mmol). The reaction was refluxed for 16 h., cooled, diluted with water, acidified with 2 M aqueous hydrochloric acid and extracted with ethyl acetate (x3). The organic extracts were washed with water and brine, dried (MgSO$_4$) and evaporated. The residue was purified by flash chromatography on silica eluting with iso-hexane/ethyl acetate (4:1) to give the title compound (65 mg).

$^1$H NMR (CDCl$_3$) δ 1.2 (3H, t, J=7.0 Hz), 1.53–1.58 (2H, m), 1.79–1.91 (3H, m), 2.36–2.42 (4H, m), 2.79 (2H, d, J=7.4 Hz), 3.20 (2H, s), 4.17–4.25 (2H, q, J=7.0 Hz), 6.80–6.87 (1H, m), 7.01–7.09 (2H, m), 7.30–7.38 (4H, m). MS (ES+) 503 ([MH]$^+$).

Example 70

[4-(4-Chloro-benzenesulfonyl)-4-(2,5-difluoro-phenyl)-cyclohexylmethanesulfonyl]-acetic acid ethyl ester

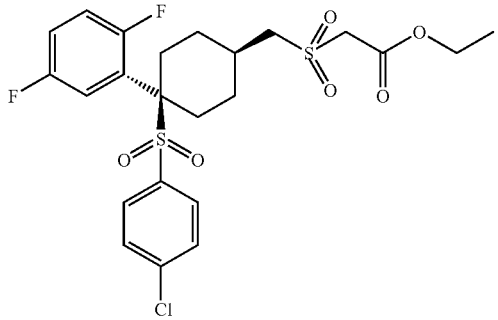

The product from Example 69 (40 mg, 0.7 mmol) was dissolved in dichloromethane (3 mL) and 3-chloroperoxybenzoic acid (60 mg, 2.1 mmol) added. The reaction was stirred for 3 h and then sodium thiosulfate (1M aqueous solution, 3 mL) added. After stirring for 5 min the dichloromethane was removed in vacuo and the residue diluted with water and extracted with ethyl acetate (x3). The organic extracts were washed with water and brine, dried (MgSO$_4$) and evaporated. The residue was purified by flash chromatography on silica eluting with iso-hexane/ethyl acetate (3:2) to give a white solid (35 mg).

$^1$H NMR (CDCl$_3$) δ 1H NMR (CDCl$_3$):1.35 (3H, t, J=7.2 Hz), 1.56–1.68 (2H, m), 1.98–2.04 (2H, m), 2.41 (2H, app t, J=12.7 Hz), 2.49 (3H, m), 3.44 (2H, d, J=6.7 Hz), 3.97 (2H, s), 4.32 (2H, q, J=7.2 Hz), 6.80–6.87 (1H, m), 7.02–7.07 (2H, m), 7.30–7.33 (2H, d, J=14 Hz), 7.34 (2H, d, J=14.1 Hz).

Example 71

[4-(4-Chloro-benzenesulfonyl)-4-(2,5-difluoro-phenyl)-cyclohexylmethylsulfanyl]-acetic acid

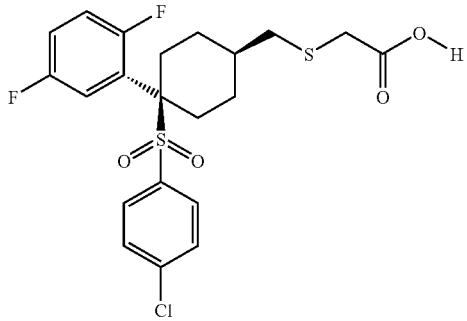

The product from Example 69 (15 mg, 0.003 mmol) was dissolved in methanol (1 mL) and lithium hydroxide (1 mg, 0.015 mmol) added. The reaction was stirred at room temperature overnight, diluted with water, acidified with 2 M aqueous hydrochloric acid and extracted with ethyl acetate (x3). The organic extracts were washed with water and brine, dried (MgSO$_4$) and evaporated. The residue was purified by flash chromatography on silica eluting with iso-hexane/ethyl acetate (1:1) to give a white solid (11 mg).

$^1$H NMR (CDCl$_3$) δ 1.50–1.58 (2H, m), 1.79–1.91 (3H, m), 2.05 (1H, s), 2.41 (3H, s), 2.82 (2H, d, J=7.4 Hz), 3.25 (2H, s), 6.80–6.87 (1H, m), 7.01–7.09 (2H, m), 7.30–7.38 (4H, m).

Example 72

2-[4-(4-Chloro-benzenesulfonyl)-4-(2,5-difluoro-phenyl)-cyclohexylmethylsulfanyl]-propionic acid ethyl ester

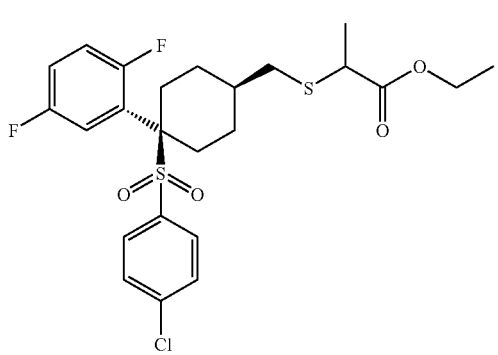

Prepared from Intermediate E (200 mg, 0.36 mmol) and ethyl 2-mercaptopropionate (50 μL, 0.4 mmol) by the method of Example 34. The product was purified by flash chromatography on silica eluting with iso-hexane/ethyl acetate (4:1) to give the title compound (100 mg).

$^1$H NMR (CDCl$_3$) δ 1.30 (3H, t, J=7.2 Hz), 1.44 (3H, d, J=7.2 Hz), 1.47 (2H, m) 1.74–1.91 (3H, m), 2.41 (4H, m), 2.79 (2H, dd, J=1.9, 7.5 Hz), 3.39 (1H, q, J=7.1 Hz), 4.11–4.27 (2H, m), 6.79–6.87 (1H, m), 7.00–7.09 (2H, m), 7.33–7.35 (4H, m).

Example 73

2-[4-(4-Chloro-benzenesulfonyl)-4-(2,5-difluoro-phenyl)-cyclohexylmethanesulfonyl]-propionic acid ethyl ester

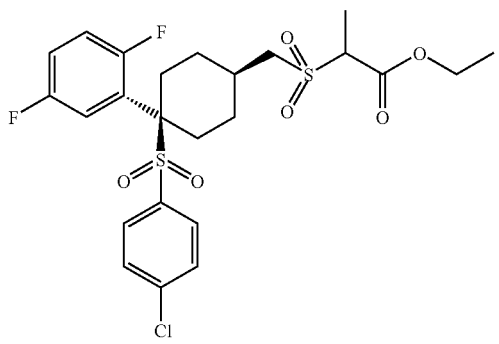

Prepared from the product from Example 72 (60 mg, 1.1 mmol) by the procedure of Example 70. The product was purified by flash chromatography on silica eluting with iso-hexane/ethyl acetate (2:1) to give a white solid (53 mg).

$^1$H NMR (CDCl$_3$) δ 1.36 (3H, t, J=7.2 Hz), 1.67 (3H, d, J=7.0 Hz), 1.95–2.04 (3H, m), 2.37–2.54 (6H, m), 3.36 (2H, dd, J=5.3, 6.3 Hz), 3.91 (1H, q, J=7.4 Hz), 4.27–4.36 (2H, m), 6.80–6.87 (1H, m), 7.02–7.08 (2H, m), 7.26–7.38 (4H, m).

Example 74

2-[4-(4-Chloro-benzenesulfonyl)-4-(2,5-difluoro-phenyl)-cyclohexylmethanesulfonyl]-propionic acid

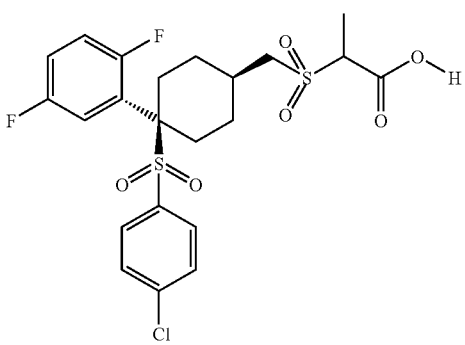

The product from Example 73 (55 mg, 0.1 mmol) was dissolved in methanol (2 mL) and lithium hydroxide (12 mg, 0.5 mmol) added. The reaction was stirred at room temperature overnight, diluted with water, acidified with 2M aqueous hydrochloric acid solution and extracted with ethyl acetate (x3). The organic extracts were washed with water and brine, dried (MgSO$_4$) and evaporated. The residue was purified by flash chromatography on silica eluting with ethyl acetate to give a white solid (48 mg).

$^1$H NMR (CDCl$_3$) δ 1.59–1.66 (2H, m), 1.71 (3H, d, J=7.0 Hz), 1.9–2.0 (3H, m), 2.40–2.53 (4H, m), 3.36–3.40 (1H, m), 3.45–3.50 (1H, m), 3.98 (1H, q, J=7.2 Hz), 6.84 (1H, m), 7.02–7.07 (2H, m), 7.30–7.38 (4H, m), 7.82–7.99 (1H, br s).

Example 75

[4-(4-Chloro-benzenesulfonyl)-4-(2,5-difluoro-phenyl)-cyclohexylmethanesulfonyl]-acetic acid

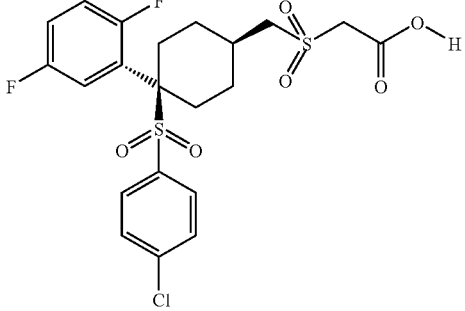

Prepared from the product from Example 70 (240 mg, 0.45 mmol) by the method of Example 74. The product was purified by flash chromatography on silica eluting with ethyl acetate to give a white solid (200 mg).

$^1$H NMR (CDCl$_3$) δ 1.59–1.70 (2H, m), 1.99–2.02 (2H, m), 2.35–2.53 (6H, m), 3.47 (2H, d, J=6.7 Hz), 4.05 (2H, s), 6.80–6.87 (1H, m), 7.03–7.08 (2H, m), 7.29–7.38 (4H, m).

Example 76

1-(4-Trifluoromethylphenylsulfonyl)-1-(2,5-difluoro-phenyl)-4-methanesulfonylmethyl-cyclohexane

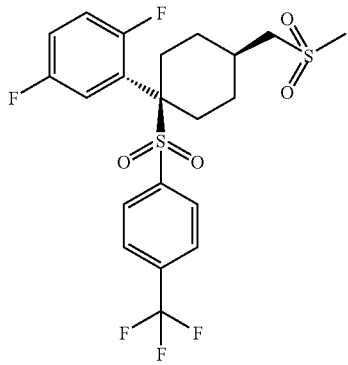

To Intermediate M (240 mg, 0.42 mmol) in ethanol (8 mL) was added sodium methanesulfinate (136 mg, 1.33 mmol). The reaction was refluxed for 18 h and after cooling was diluted with water, and extracted with ethyl acetate (x3). The organic extracts were washed with water and brine, dried (MgSO$_4$) and evaporated. The residue was purified by flash chromatography on silica eluting with ethyl acetate to give the title compound (80 mg).

$^1$H NMR (CDCl$_3$) δ 1.61–1.71 (2H, m), 1.99–2.04 (2H, m), 2.41–2.49 (5H, m), 2.97 (3H, s), 3.18 (2H, d, J=6.7 Hz), 6.77–6.85 (1H, m), 7.03–7.08 (2H, m), 7.50 (1H, s), 7.53 (1H, s), 7.64 (1H, s), 7.67 (1H, s). MS (ES+) 519 ([MNa]+).

Example 77

2-[4-(4-Chloro-benzenesulfonyl)-4-(2,5-difluoro-phenyl)-cyclohexylmethanesulfonyl]-acetamide

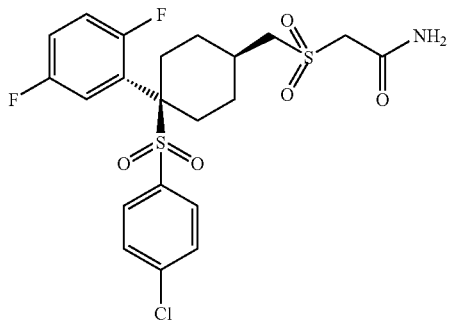

To the product of Example 75 (100 mg, 0.2 mmol) in ethyl acetate (8 mL) was added pentafluorophenol (55 mg, 0.3 mmol). The solution was cooled to 0° C. and dicyclohexylcarbodiimide was added (62 mg, 0.3 mmol). After 2 h the reaction was filtered through Celite® and the filtrate concentrated to give a white solid (130 mg). This was dissolved in a 2 M solution of ammonia in methanol (10 ml) and heated to 50° C. in a sealed tube for 16 h. The mixture was concentrated and the residue purified by flash chromatography on silica eluting with dichloromethane/methanol (9:1) to give a white solid (45 mg).

$^1$H NMR (CDCl$_3$) δ 1.61–1.70 (2H, m), 1.98–2.04 (2H, m), 2.41–2.47 (4H, m), 3.33 (2H, d, J=6.7 Hz), 3.90 (2H, s), 5.62–5.70 (1H, m), 6.44 (1H, m), 6.79–6.87 (1H, m), 7.03–7.08 (2H, m), 7.29 (1H, s), 7.34 (3H, d, J=13.7 Hz), 7.38 (1H, s). MS (ES+) 506 ([MH]+).

Example 78

2-[4-(2,5-Difluoro-phenyl)-4-(4-trifluoromethyl-benzenesulfonyl)-cyclohexylmethylsulfanyl]-pyridine

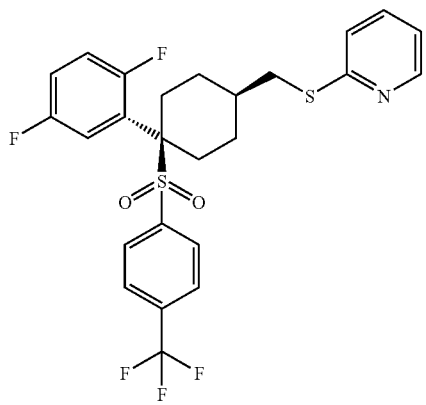

Prepared from Intermediate M (340 mg, 0.625 mmol) and 2-mercaptopyridine (90 mg, 0.813 mmol) by the method of Example 34. The product was purified by flash chromatography on silica eluting with iso-hexane/ethyl acetate (3:1) to give the title compound (315 mg).

$^1$H NMR (CDCl$_3$) δ 1.51–1.58 (2H, m), 1.95 (3H, dd, J=13.3, 2.8 Hz), 2.48–2.55 (4H, m), 3.36 (2H, d, J=7.4 Hz), 6.77–6.84 (1H, m), 6.95–7.11 (3H, m), 7.17 (1H, d, J=8.1 Hz), 7.44–7.49 (1H, m), 7.54 (2H, d, J=10 Hz), 7.64 (2H, d, J=10 Hz), 8.41–8.43 (1H, m). MS (ES+) (MH+-F) 509

Example 79

2-[4-(2,5-Difluoro-phenyl)-4-(4-trifluoromethyl-benzenesulfonyl)-cyclohexylmethylsulfanyl]-pyrimidine

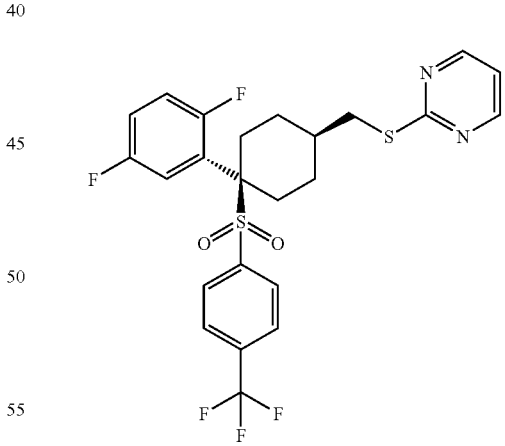

Prepared from Intermediate M (330 mg, 0.61 mmol) and 2-mercaptopyrimidine (88 mg, 0.79 mmol) by the method of Example 34. The product was purified by flash chromatography on silica eluting with iso-hexane/ethyl acetate (3:1) to give the title compound (315 mg).

$^1$H NMR (CDCl$_3$) δ 1.56–1.61 (2H, m), 1.95–1.98 (3H, m), 2.49–2.53 (4H, m), 3.34 (2H, d, J=7.0 Hz), 6.77–6.84 (1H, m), 6.95–7.11 (3H, m), 7.54 (1H, s), 7.56 (1H, s), 7.65 (1H, s), 7.67 (1H, s), 8.51 (2H, d, J=4.7 Hz). MS (ES+) 529 ([MH]+), 510 ([MH-F]+).

Example 80

2-[4-(2,5-Difluoro-phenyl)-4-(4-trifluoromethyl-benzenesulfonyl)-cyclohexylmethanesulfonyl]-pyridine

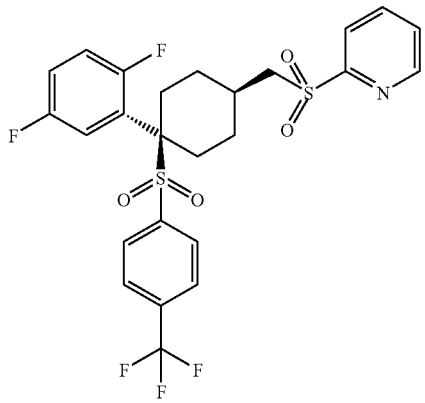

To a solution of sodium periodate (223 mg, 1 mmol) in ethyl acetate (2 mL) and water (4 mL) was added ruthenium dioxide (5 mg), followed by the product from Example 78 (250 mg, 0.47 mmol) in ethyl acetate (2 mL). After 30 mins the reaction was diluted with ethyl acetate, filtered through Celite® and the water layer from the filtrate removed. The organic layer was dried (MgSO$_4$), evaporated, and the residue purified by flash chromatography on silica eluting with iso-hexane/ethyl acetate (1:1) to give a white solid (220 mg).

$^1$H NMR (CDCl$_3$) δ 1.55–1.65 (2H, m), 1.95–2.00 (2H, m), 2.38–2.48 (5H, m), 3.56 (2H, d, J=6.3 Hz), 6.76–6.84 (1H, m), 7.02–7.07 (2H, m), 7.50 (1H, s), 7.53 (1H, s), 7.56–7.60 (1H, m), 7.64 (1H, s), 7.66 (1H, s), 7.97–8.01 (1H, m), 8.10 (1H, s), 8.77–8.79 (1H, m). MS (ES+) 560 ([MH]$^+$)

Example 81

2-[4-(2,5-Difluoro-phenyl)-4-(4-trifluoromethyl-benzenesulfonyl)-cyclohexylmethanesulfonyl]-pyrimidine

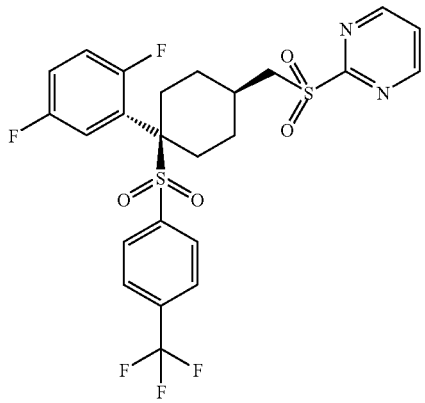

Prepared from Example 79 by the method of Example 80.

$^1$H NMR (CDCl$_3$) δ 1.61–1.70 (2H, m), 2.01–2.06 (2H, m), 2.41–2.60 (5H, m), 3.70 (2H, d, J=6.7 Hz), 6.81 (1H, dd, J=2.5, 4.9 Hz), 7.03–7.08 (2H, m), 7.51 (1H, s), 7.53 (1H, s), 7.60 (1H, t, J=4.9 Hz), 7.64 (1H, s), 7.67 (1H, s), 8.99 (2H, d, J=4.9 Hz). MS (ES+) 561 ([MH]$^+$)

Example 82

1-(4-Chlorophenylsulfonyl)-1-(2,5-difluoro-phenyl)-4-ethanesulfonylmethyl-cyclohexane

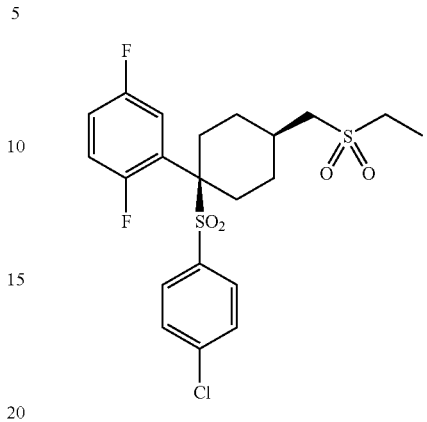

Intermediate E (106 mg, 0.21 mmol) was refluxed with sodium ethanethiolate (19 mg, 0.23 mmol) in ethanol (5 mL) for 6.5 hrs. The cooled mixture was diluted with ethyl acetate, washed with 2N aqueous sodium hydroxide, dried (MgSO$_4$) and evaporated to a white foam. The product was purified by flash chromatography on silica (25% diethyl ether/hexane) yielding 50 mg of the desired thioether intermediate.

This intermediate in dichloromethane (5 mL) was treated with 3-chloroperoxybenzoic acid (50% in water, 98 mg, 0.57 mmol) at 0° C. and stirred for 19 hours at ambient temperature. The reaction mixture was quenched with saturated sodium sulfite solution, and the organic layer washed with 2N aqueous sodium hydroxide, dried (MgSO$_4$) and evaporated to yield a white solid. Purification by flash chromatography on silica eluting with diethyl ether yielded the title compound as a white solid (11 mg).

$^1$H NMR (360 MHz, CDCl$_3$) δ 7.39–7.25 (4H, m), 7.09–7.01 (2H, m), 6.87–6.79 (1H, m), 3.09–3.07 (2H, m), 3.03 (2H, q, J=7.5 Hz), 2.48–2.38 (5H, m), 2.03–1.98 (2H, m), 1.69–1.62 (2H, m), 1.44 (3H, t, J=7.5 Hz). MS (ES+) 477 ([MH]$^+$).

Example 83

2-(trifluoromethyl)-[4-(4-chloro-benzenesulfonyl)-4-(2,5-difluoro-phenyl)-cyclohexylmethanesulfonyl]-benzene

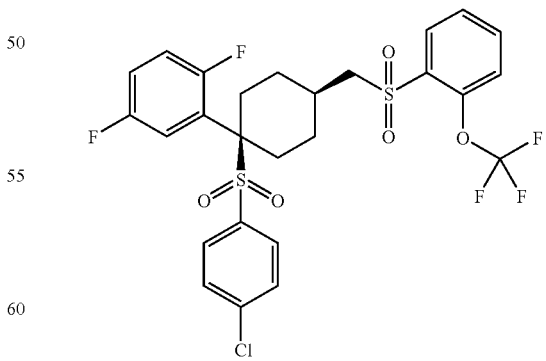

To a stirred solution of Intermediate E (62 mg, 0.12 mmol) and 2-trifluoromethoxy thiophenol (26 mg, 0.13 mmol) in ethanol (5 mL) was added crushed potassium hydroxide (ca. 10 mg, ca. 0.16 mmol) and the mixture heated to 80° C. for 1 hour, then cooled. Ethyl acetate (20 mL) was added and the solution washed with 1N aqueous sodium hydroxide (20 mL) and brine (20 mL), dried (MgSO₄) and evaporated to leave a residue of the crude thioether which was dissolved in ethyl acetate (4 mL) and added to a vigorously stirred solution of ruthenium(IV) oxide hydrate (ca. 3 mg) and sodium periodate (50 mg) in water (2 mL). The biphasic mixture was vigorously stirred for 20 minutes then diluted with further ethyl acetate (20 mL) and water (10 mL) and the layers separated. The organic phase was washed with further water (10 mL) and brine (20 mL), dried (MgSO₄) and evaporated to leave a residue which was purified by flash column chromatography on silica, eluting with diethyl ether:iso-hexane 1:1, to afford the desired product (44 mg).

MS (ES⁺) 626 ([MNH₄]⁺).

Examples 84 to 90 were made by the method Example 83 using the appropriate thiophenol.

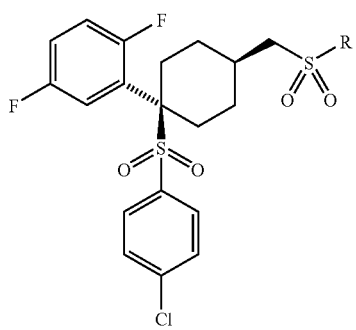

| Example | R | MS (ES+)/(ES−) |
|---|---|---|
| 84 | 2-methoxyphenyl | 555 ([MH]⁺) |
| 85 | 2-fluorophenyl | 565 ([MNa]⁺) |
| 86 | 4-fluorophenyl | 565 ([MNa]⁺) |
| 87 | 2,4-difluorophenyl | 583 ([MNa]⁺) |
| 88 | 2-hydroxyphenyl | 539 ([M − H]⁻) |
| 89 | 3-hydroxyphenyl | 539 ([M − H]⁻) |
| 90 | 4-hydroxyphenyl | 539 ([M − H]⁻) |

Example 91

[4-(4-Chloro-benzenesulfonyl)-4-(2,5-difluoro-phenyl)-cyclohexyl]-methylisothiocyanate

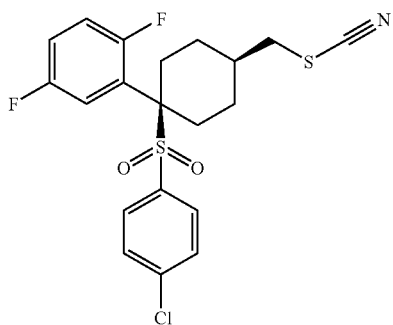

To a stirred solution of Intermediate E (118 mg, 0.23 mmol) in N,N-dimethylformamide (10 mL) was added potassium isothiocyanate (112 mg, 1.05 mmol) and the mixture warmed to 80° C. for 18 hours. Upon cooling, ethyl acetate (20 mL) was added and the solution washed with water (3×20 mL) and brine (20 mL), dried (MgSO₄) and evaporated to leave a residue which was purified by flash column chromatography on silica, eluting with diethyl ether: iso-hexane 1:3, to afford the desired product (89 mg, 0.18 mmol.).

MS (ES⁺) 459 ([MNH₄]⁺).

Example 92

{[4-(4-chloro-benzenesulfonyl)-4-(2,5-difluoro-phenyl)-cyclohexyl]-methyl}-trifluoromethyl Sulfone

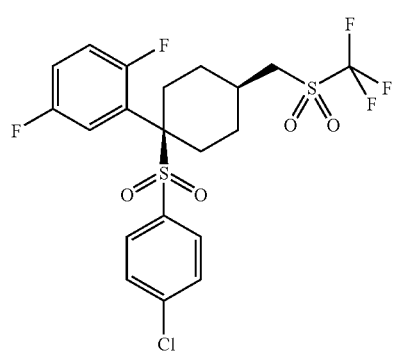

The product from Example 91 (80 mg, 0.18 mmol) in tetrahydrofuran (5 mL) at 0° C. was treated with trimethyl (trifluoromethyl)silane (0.055 mL, 0.36 mmol) tetrabutylammonium fluoride (0.04 mL of a 1M solution in tetrahydrofuran, 0.04 mmol) and the mixture stirred for 5 minutes at 0° C. then 3 hours at room temperature. Diethyl ether (20 mL) was added and the solution washed with water (2×20 mL) and brine (20 mL), dried (MgSO₄) and evaporated to leave a residue which was purified by flash column chromatography on silica eluting with diethyl ether:iso-hexane 1:3, to afford {[4-(4-chloro-benzenesulfonyl)-4-(2,5-difluoro-phenyl)-cyclohexyl]-methyl}-trifluoromethyl sulfide (49 mg,).

Of this, 47 mg (0.1 mmol) was oxidised to the sulfone by the method described in Example 83. Final purification was by flash column chromatography on silica eluting with diethyl ether:iso-hexane 1:2, to afford the desired product (38 mg).

¹H NMR (360 MHz, CDCl₃) δ 7.36 (2H, d, J=10.8 Hz), 7.29 (2H, d, J=10.8 Hz) 7.08–7.03 (2H, m) 6.87–6.80 (1H, m), 3.34 (2H, d, J=6.8 Hz), 2.59–2.48 (5H, m), 2.06–1.99 (2H, m), 1.78–1.70 (2H, m). MS (ES+) 534 ([MNH₄]⁺).

Example 93

2-[4-(4-Chloro-benzenesulfonyl)-4-(2,5-difluoro-phenyl)-cyclohexylmethanesulfonyl]-furan

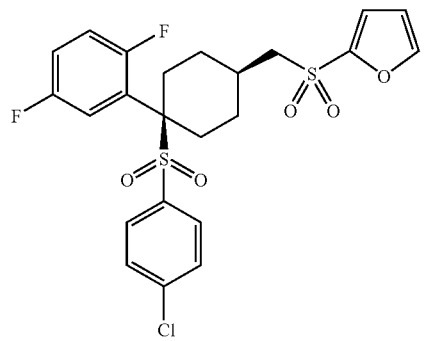

To a solution of furan (0.043 mL, 0.67 mmol) in tetrahydrofuran (5 mL) at −40° C. under nitrogen was added n-butyl lithium (0.41 mL of a 1.6M solution in hexanes, 0.66 mmol) and the reaction allowed to attain room temperature over 1 hour. Upon recooling to 0° C., sulfur (6 mg, 0.19 mmol) was added and the reaction stirred for 30 minutes at 0° C. before a solution of Intermediate E (100 mg, 0.20 mmol) in ethanol (5 mL) was added. The mixture was then warmed to 60° C. for 75 minutes, cooled, quenched by the addition of a saturated aqueous solution of ammonium chloride (20 mL), then extracted into ethyl acetate (2×30 mL). The combined organics were washed with water (2×10 mL) and brine (20 mL), dried (MgSO$_4$) and evaporated to leave a residue of the crude furan thioether (102 mg).

This was oxidised to the sulfone by the method described in Example 83. Final purification was by flash column chromatography on silica, eluting with diethyl ether:iso-hexane 1:1, to afford the desired product (26 mg).

$^1$H NMR (360 MHz, CDCl$_3$) δ 7.66 (1H, d, J=1.7 Hz), 7.36 (2H, d, J=8.8 Hz), 7.29 (2H, d, J=8.8 Hz) 7.18 (1H, d, J=3.4 Hz), 7.06–7.01 (2H, m) 6.86–6.79 (1H, m), 6.57 (1H, dd, J=3.4, 1.7 Hz), 3.35 (2H, d, J=6.5 Hz), 2.51–2.30 (5H, m), 1.95–1.84 (2H, m), 1.64–1.52 (2H, m).MS (ES$^+$) 532 ([MNH$_4$]$^+$).

Example 94

1-(4-Chlorophenylsulfonyl)-1-(2,5-difluoro-phenyl)-4-methanesulfonylmethylene-cyclohexane

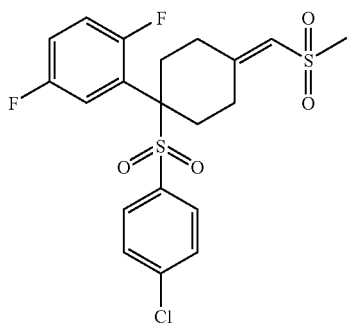

To a stirred solution of diisopropylamine (0.72 mL, 5.2 mmol) in tetrahydrofuran (40 mL) at −78° C. was added dropwise a solution of n-butyl lithium (1.6M in hexanes, 3.2 mL, 5.1 mmol). The mixture was allowed to warm briefly to room temperature then recooled to −78° C. and dimethyl sulfone (470 mg, 5.1 mmol) in tetrahydrofuran (10 mL) added dropwise. After stirring for 20 minutes at −78° C., Intermediate A (640 mg, 1.67 mmol) in tetrahydrofuran (10 mL) was added and stirring continued for a further 1 hour. The reaction was quenched by the addition of saturated aqueous ammonium chloride (50 mL), allowed to warm to room temperature then extracted into ethyl acetate (2×50 mL). The combined organics were washed with 2N aqueous hydrochloric acid (2×50 mL) and brine (50 mL), dried (MgSO$_4$) and evaporated to leave a residue which was purified by flash column chromatography on silica, eluting with ethyl acetate:iso-hexane 1:1, to afford 4-(4-chlorobenzenesulfonyl)-4-(2,5-difluoro-phenyl)-1-methanesulfonylmethyl-cyclohexanol (630 mg).

MS (ES$^+$) 496 ([MNH$_4$]$^+$).

The alcohol from the foregoing step (420 mg, 0.88 mmol) in dichloromethane (20 mL) was cooled to 0° C. under nitrogen and triethylamine (0.25 mL, 1.7 mmol) and methane sulfonyl chloride (0.1 mL, 1.3 mmol) were added. The reaction was stirred for 1 hour at 0° C. then further triethylamine (0.5 mL, 3.4 mmol) and methane sulfonyl chloride (0.21 mL, 2.7 mmol) added. After a further 30 minutes, the solution was washed with 2N aqueous hydrochloric acid (2×10 mL) and brine (10 mL), dried (MgSO$_4$), evaporated and the residue taken up in tetrahydrofuran (20 mL). 1,8-diazabicyclo[5.4.0]undec-7-ene (0.26 mL, 1.7 mmol) was added and the mixture stirred for 5 minutes. Ethyl acetate (30 mL) was added, the solution washed with 1N aqueous sodium hydroxide (20 mL), and the aqueous layer extracted with further ethyl acetate (10 mL). The combined organic layers were washed with 2N aqueous hydrochloric acid (20 mL) and brine (20 mL), dried (MgSO$_4$) and evaporated to leave a residue which was purified by flash column chromatography on silica eluting with ethyl acetate:iso-hexane 1:1, to afford the desired product (196 mg).

MS (ES$^+$) 478 ([MNH$_4$]$^+$).

Example 95

1-(4-Chlorophenylsulfonyl)-1-(2,5-difluoro-phenyl)-4-methanesulfonylmethyl-cyclohexane

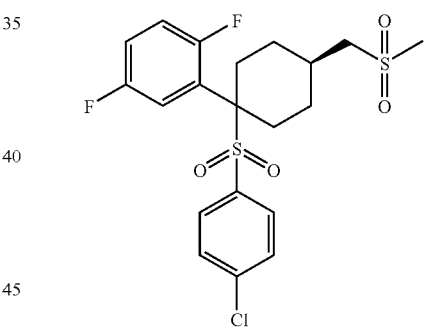

The product of Example 94 (150 mg, 0.32 mmol) in tetrahydrofuran (20 mL) at −40° C. was treated dropwise with L-Selectride™ (1M solution in tetrahydrofuran, 0.5 mL, 0.5 mmol). The reaction was stirred at −40° C. for 90 minutes, then quenched by the addition of ethanol (4 drops) then water (10 mL). The mixture was extracted into ethyl acetate (2×50 mL) and the combined organics washed with brine (50 mL), dried (MgSO$_4$) and evaporated to leave a residue which was purified by flash column chromatography on silica eluting with diethyl ether:dichloromethane:iso-hexane 1:2:1, to afford the desired product (107 mg).

$^1$H NMR (400 MHz, CDCl$_3$) δ 7.36 (2H, d, J=8.8 Hz), 7.29 (2H, d, J=8.8 Hz) 7.07–7.03 (2H, m) 6.87–6.82 (1H, m), 3.17 (2H, d, J=6.6 Hz), 2.96 (3H, s), 2.55–2.36 (5H, m), 2.02–1.98 (2H, m), 1.68–1.62 (2H, m). MS (ES+) 480 ([MNH$_4$]$^+$).

Example 96

4-({1-(2,5-difluorophenyl)-4-[(methylsulfonyl)methyl]cyclohexyl}sulfonyl) benzonitrile

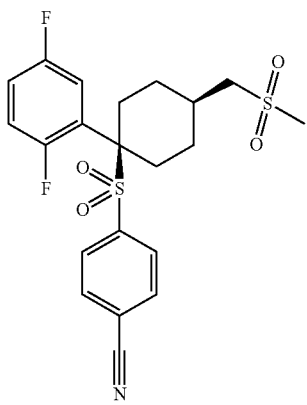

Nitrogen was bubbled through a solution of Intermediate B (1.0 g, 2.2 mmol), tri-t-butylphosphine (0.2M in dioxane, 0.657 mL, 0.13 mmol), cesium fluoride (0.733 g, 4.82 mmol) and tris(dibenzylideneacetone)dipalladium(0) (0.10 g, 0.11 mmol) in dioxane (6 mL) in a sealed tube for 5 minutes. Vinyltributyltin (0.729 g, 2.3 mmol) was added and the mixture was heated at 100° C. for 3 hours then diluted with diethyl ether (20 ml), passed through a silica gel pad and evaporated in vacuo. The crude mixture was purified by flash chromatography on silica eluting with 20–24% diethyl ether/isohexane and the product azeotroped with dichloromethane to give [4-(2,5-difluoro-phenyl)-4-(4-vinyl-benzenesulfonyl)-cyclohexyl]-acetic acid ethyl ester (0.89 g, 91%).

$^1$H NMR (CDCl$_3$, 400 MHz) δ 1.27 (3H, t, J=6.4 Hz), 1.50–1.57 (2H, m), 1.73 (2H, dd, J=3.1, 12.8 Hz), 2.12–2.20 (1H, m), 2.37–2.48 (6H, m), 4.14 (2H, q, J=6.4 Hz), 5.44 (1H, d, J=9.8 Hz), 5.88 (1H, d, J=15.8 Hz), 6.72 (1H, dd, J=9.8, 15.8 Hz), 6.79–6.85 (1H, m), 6.99–7.04 (2H, m). 7.34 (2H, d, J=8.6), 7.37 (2H, d, J=8.6).

Ozone was bubbled through two solutions both containing the above intermediate (3.883 g, 8.7 mmol) in dichloromethane/methanol (200 mL/40 mL) at −78° C. for 20 minutes until the solutions turned blue. Oxygen was bubbled through both solutions for 15 minutes until the blue colour disappeared. Both solutions were quenched with dimethyl sulfide (3.23 g, 52 mmol), allowed to warm to room temperature and stirred for 1.5 hours. The reaction mixtures were combined and evaporated in vacuo to give a crude oil (10.761 g), which was purified by flash chromatography on silica, eluting with 15–22% ethyl acetate/isohexane to give [4-(2,5-difluoro-phenyl)-4-(4-formyl-benzenesulfonyl)-cyclohexyl]-acetic acid ethyl ester (7.029 g, 90%).

$^1$H NMR (CDCl$_3$, 360 MHz) δ 1.27 (3H, t, J=7.2 Hz), 1.48–1.58 (2H, m), 1.73–1.78 (2H, m), 2.15–2.20 (1H, m), 2.48 (6H, m), 4.14 (2H, q, J=7.2 Hz), 67.5–6.82 (1H, m), 7.01–7.11 (2H, m), 7.57 (2H, d, J=8.3 Hz), 7.87 (2H, d, J=8.4 Hz), 10.09 (1H, s).

A solution of this intermediate (6.3 g, 13.8 mmol), hydroxylamine hydrochloride salt (2.87 g, 41 mmol) and sodium acetate (3.38 g, 41 mmol) in ethanol (400 mL) was heated at reflux for 2 hours then evaporated in vacuo to give the crude product (7.52 g) which was purified by flash chromatography on silica, eluting with 25–35% ethyl acetate/isohexane to give {4-(2,5-difluoro-phenyl)-4-(hydroxyimino-methyl)-benzenesulfonyl]-cyclohexyl}-acetic acid ethyl ester (4.043 g) and mixed fractions (3.4 g). The mixed fractions were purified by flash chromatography on silica, eluting with 28–31% ethyl acetate/isohexane to give further product (2.04 g).

$^1$H NMR (d$_6$-DMSO, 360 MHz) δ 1.18 (3H, t, J=7.1 Hz), 1.43–1.52 (2H, m), 1.62 (2H, m), 2.03 (1H, m), 2.18 (2H, bt, J=12.3 Hz), 2.39 (2H, d, J=7.6 Hz), 2.44 (2H, m), 4.05 (2H, q, J=7.1 Hz), 7.08–7.20 (2H, m), 7.30 (1H, m), 7.37 (2H, d, J=8.4 Hz), 7.70 (2H, d, J=8.4 Hz), 8.23 (1H, s), 11.73 (1H, s).

Triphenylphosphine (4.14 g, 15.8 mmol) was added to a solution of {the above intermediate in acetonitrile (25 mL), followed by carbon tetrachloride (0.75 mL, 7.9 mmol) and the mixture stirred at room temperature for 1 hour. Additional carbon tetrachloride (1.75 mL) was added, and after stirring at room temperature for 1.5 hours the mixture was diluted with water (20 mL) and extracted with ethyl acetate (2×20 mL). The combined organic layers were washed with brine (30 mL), dried (magnesium sulphate) and evaporated in vacuo. The crude product was purified by flash chromatography on silica, eluting with 25% ethyl acetate/isohexane to give [4-(4-cyano-benzenesulfonyl)$_4$-(2,5-difluoro-phenyl)-cyclohexyl]-acetic acid ethyl ester (1.065 g) plus mixed fractions (0.781 g).

$^1$H NMR (CDCl$_3$, 360 MHz) δ 1.25 (3H, t, J=7.0 Hz), 1.50–1.60 (2H, m), 1.72–178 (2H, m), 2.13–2.20 (1H, m), 2.42–2.48 (6H, m), 4.14 (2H, q, J=7.0 Hz), 6.76–6.83 (1H, m), 7.00–7.12 (2H, m), 7.52 (2H, d, J=8.5 Hz), 7.68 (2H, d, J=8.6 Hz).

A solution of the above intermediate ethyl ester (1.045 g, 2.3 mmol) and lithium hydroxide solution (1.0M, 7.0 mL) in dioxane (7 mL) was stirred at room temperature for 4 hours then acidified with citric acid and extracted with ethyl acetate (15 mL). The organic phase was washed with water (10 mL) and brine (10 mL), dried (magnesium sulphate) and evaporated in vacuo. The crude product was purified by flash chromatography on silica, eluting with ethyl acetate to give [4-(4-cyano-benzenesulfonyl)-4-(2,5-difluoro-phenyl)-cyclohexyl]-acetic acid (0.826 g, 84%).

$^1$H NMR (CDCl$_3$, 360 MHz) δ 1.57 (2H, m), 1.80 (2H, m), 2.19 (1H, m), 2.45 (4H, m), 2.54 (2H, d, J=7.5 Hz), 6.80 (1H, m), 7.08 (2H, m), 7.51 (2H, d, J=8.5 Hz), 7.67 (2H, d, J=8.6 Hz).

A portion of the above acid (0.272 g, 0.65 mmol) was converted to the corresponding iodide following the procedure of Intermediate E. The crude product was purified by flash chromatography on silica, eluting with 0–14% ethyl acetate/isohexane to give iodo-[4-(4-cyano-benzenesulfonyl)-4-(2,5-difluoro-phenyl)-cyclohexyl]-methane (0.169 g, 52%). $^1$H NMR (CDCl$_3$, 360 MHz) δ 1.55–1.65 (2H, m), 1.91–2.04 (3H, m), 2.36–2.49 (4H, m), 3.36 (2H, d, J=7.6 Hz), 6.76–6.84 (1H, m), 7.04–7.13 (2H, m), 7.51 (2H d, J=8.4 Hz), 7.68 (2H, d, J=8.5 Hz).

A solution of the above iodide (0.169 g, 0.34 mmol) and sodium methanesulphinate (0.172 g, 1.7 mmol) in dry N,N-dimethylformamide (2.5 mL) was warmed at 80° C. for 16 hours. The cooled mixture was diluted with ethyl acetate (10 mL), washed with water (3×10 mL) and brine (20 mL), dried (magnesium sulphate) and evaporated in vacuo. The crude product was purified by flash chromatography on silica, eluting with 8–50% ethyl acetate/isohexane to give the title compound (0.055 g, 36%).

$^1$H NMR (CDCl$_3$, 360 MHz) δ 1.60–1.71 (2H, m), 1.96–2.06 (2H, m), 2.40–2.51 (5H, m), 2.97 (3H, s), 3.18 (2H, d, J=6.6 Hz), 6.75–6.85 (1H, m), 7.03–7.06 (2H, m), 7.50 (2H, d, J=8.5 Hz), 7.68 (2H, d, J=8.5 Hz).

Example 97

1-(4-Chlorophenylsulfonyl)-1-(2,5-difluoro-phenyl)-4-phenylsulfonylmethyl-cyclohexane

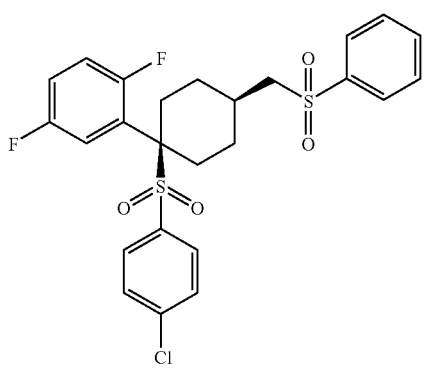

To a stirred solution of Intermediate E (47 mg, 0.09 mmol) in N,N-dimethylformamide (5 mL) was added sodium phenylsulfinate (52 mg, 0.32 mmol) and the mixture warmed to 60° C. for 6 hours. The cooled mixture was diluted with ethyl acetate (25 mL), washed with water (3×20 mL) and brine (20 mL), dried (MgSO$_4$) and evaporated to leave a residue which was purified by flash column chromatography on silica eluting with diethyl ether:dichloromethane:iso-hexane 1:1:3, to afford the desired product (15 mg). MS (ES+) 542 ([MNH$_4$]$^+$).

Example 98

1-(4-Chlorophenylsulfonyl)-1-(2,5-difluoro-phenyl)-4-[(cyanomethyl)sulfonylmethyl]-cyclohexane

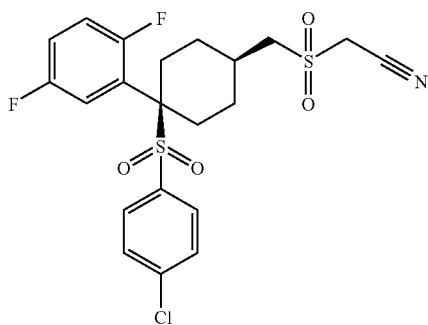

To a stirred solution of Intermediate I (120 mg, 0.29 mmol) in acetonitrile (5 mL) was added potassium carbonate (41 mg, 0.30 mmol) and a solution of chloroacetonitrile (0.04 mL, 0.64 mmol) in acetonitrile (10 mL) and the reaction warmed to 50° C. for 2 hours. Upon cooling, the mixture was filtered and the filtrate evaporated. The residue was taken up in ethyl acetate (3 mL) and oxidised to the sulphone by the method described in Example 83. Final purification was by flash column chromatography on silica eluting with diethyl ether:iso-hexane 1:1, to afford the desired product (51 mg).

MS (ES$^-$) 486 ([M-H]$^-$).

Example 99

1-(2,5-Difluoro-phenyl)-1-(4-trifluoromethylphenyl-sulfonyl)-4-propylsulfonylethyl-cyclohexane

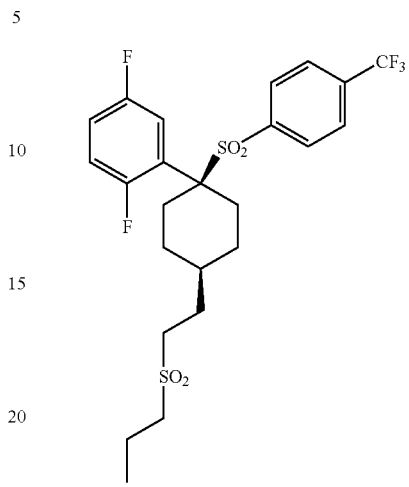

A stirred solution of Intermediate P (0.115 g, 0.22 mmol), 1-propanethiol (0.021 mL, 0.22 mmol) and powdered potassium hydroxide (0.015 mg, 0.26 mmol) in ethanol (5 mL) was heated at reflux for 45 minutes, then evaporated. The residue was dissolved in diethyl ether (25 mL), washed with brine (20 mL), dried over magnesium sulfate and evaporated to dryness. The resulting crude thioether in dichloromethane (10 mL) was treated with 3-chloroperoxybenzoic acid (0.22 g, 60% w/w) and stirred for 18 hours. The reaction was then washed with 10% aqueous sodium bisulfite solution (30 mL), saturated sodium bicarbonate solution (20 mL) and brine (20 mL). The organic phase was evaporated to dryness and the product purified by silica gel chromatography eluting with ethyl acetate/hexane mixtures to give pure product (0.065 g).

$^1$H NMR (360 MHz, CDCl$_3$) δ 7.64 (2H, d, J=8.2 Hz), 7.52 (2H, d, J=8.2 Hz), 7.09–7.01 (2H, m), 6.83–6.76 (1H, m), 2.99–2.88 (4H, m), 2.55–2.37 (4H, m), 2.04–1.85 (4H, m), 1.79–1.60 (3H, m), 1.60–1.54 (2H, m) and 1.12 (3H, t, J=7.4 Hz). MS (ES+) 539 ([MH]$^+$).

Examples 100 to 103 were prepared from Intermediate P by the method of Example 99 using the appropriate thiol.

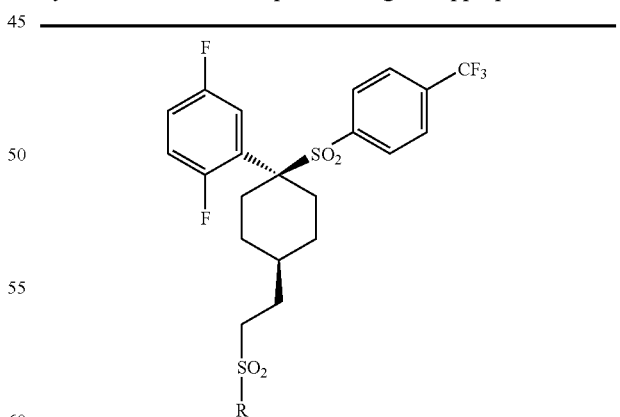

| Example | R | MS (ES+) |
|---|---|---|
| 100 | Isopropyl | 539 ([MH]$^+$) |
| 101 | 2-pyridyl | 574 ([MH]$^+$) |
| 102 | 2-pyrimidyl | 575 ([MH]$^+$) |
| 103 | 2-chlorophenyl | 629 ([MNa]$^+$) |

Example 104

1-(4-Chlorophenylsulfonyl)-1-(2,5-difluoro-phenyl)-4-[2-(methylsulfonyl)ethyl]-cyclohexane

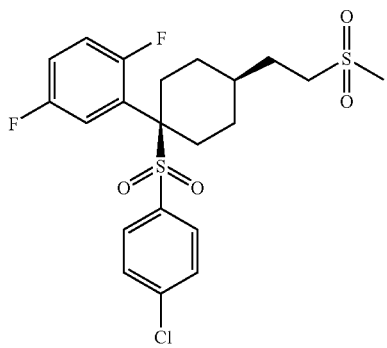

Intermediate F (100 mg, 0.19 mmol) and sodium methylsulfinate (97 mg, 0.95 mmol) in N,N-dimethylformamide (10 mL) were warmed to 80° C. for 5 hours, then cooled, diluted with diethyl ether (50 mL), washed with water (3×50 mL) and brine (50 mL), dried (MgSO$_4$) and evaporated to leave a residue which was purified by flash column chromatography eluting with diethyl ether:dichloromethane:iso-hexane 1:1:2, to afford the desired product (67 mg).

MS (ES+) 499 ([MNa]$^+$).

Example 105

2-[4-(4-Chloro-benzenesulfonyl)-4-(2,5-difluoro-phenyl)-cyclohexyl]-ethanesulfonic acid amide

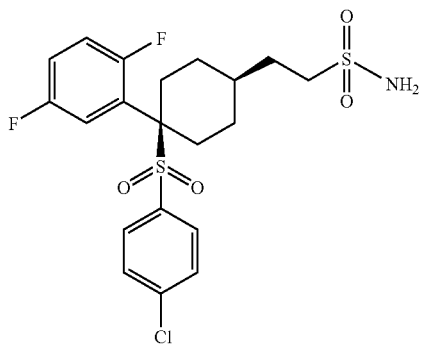

Intermediate D (5.09 g, 12.3 mmol) was converted to the mesylate following the procedure of Intermediate P. Trituration of the crude product with diethyl ether (with trace dichloromethane) afforded methanesulfonic acid 2-[4-(4-chloro-benzenesulfonyl)-4-(2,5-difluoro-phenyl)-cyclohexyl]-ethyl ester (4.7 g). The mother liquors were purified by flash column chromatography on silica eluting with diethyl ether:dichloromethane:iso-hexane 2:2:3, to afford further product (0.95 g).

The foregoing mesylate (1.18 g, 2.4 mmol) was converted to the thiol following the procedure of Intermediate I. The yield of crude [4-(4-chloro-benzenesulfonyl)-4-(2,5-difluoro-phenyl)-cyclohexyl]-ethanethiol was 1.22 g.

This product was converted to the sulfonyl chloride by the procedure of Intermediate Q, affording [4-(4-chloro-benzenesulfonyl)-4-(2,5-difluoro-phenyl)-cyclohexyl]-ethanesulfonyl chloride as a colourless solid (0.88 g).

The sulfonyl chloride from the foregoing step (55 mg, 0.11 mmol) was dissolved in dichloromethane (10 ml) and ammonia gas bubbled through for 5 minutes. The resulting cloudy solution was stirred at ambient temperature for 15 minutes then evaporated and taken up in ethyl acetate (20 mL), washed with water (20 ml) and brine (20 mL), dried (MgSO$_4$) and evaporated to leave a residue which was triturated with diethyl ether to afford the desired product (51 mg)

$^1$H NMR (360 MHz, CDCl$_3$) δ 7.37–7.30 (4H, m), 7.08–7.00 (2H, m), 6.86–6.79 (1H, m), 4.89 (2H, br s), 3.15 (2H, m), 2.51–2.44 (4H, m), 2.08–2.02 (2H, m), 1.78–1.72 (3H, m) and 1.57–1.50 (2H, m). MS (ES+) 500 ([MNa]$^+$).

Example 106

2-[4-(4-Chloro-benzenesulfonyl)-4-(2,5-difluoro-phenyl)-cyclohexyl]-ethanesulfonic acid acetyl-amide

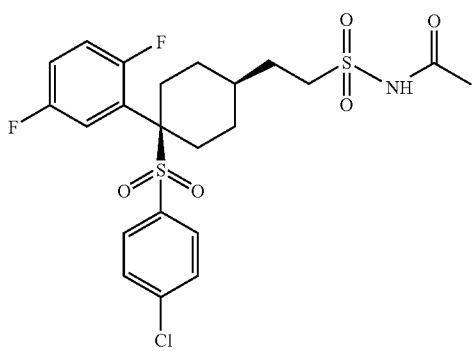

To a stirred solution of the product of Example 105 (141 mg, 0.28 mmol) in dichloromethane (10 mL) was added 1-(3-dimethylaminopropyl)-3-ethylcarbodiimide hydrochloride (104 mg, 0.54 mmol), dimethylaminopyridine (66 mg, 0.57 mmol) and acetic acid (0.035 mL, 0.58 mmol). The mixture was stirred for 18 hours, diluted with ethyl acetate (20 mL), washed with 2N aqueous hydrochloric acid (20 mL) and brine (100 mL), dried (MgSO$_4$) and evaporated to leave a residue which was purified by column chromatography on silica eluting with ethyl acetate: dichloromethane: iso-hexane 2:1:1, to afford the desired product (90 mg).

MS (ES+) 542 ([MNa]$^+$).

Example 107

2-[4-(4-Chloro-benzenesulfonyl)-4-(2,5-difluoro-phenyl)-cyclohexyl]-ethanesulfonic acid tert-butyla-mide

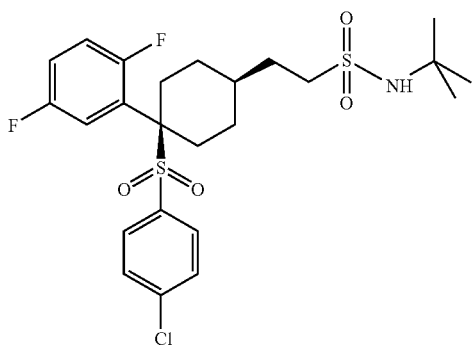

To a stirred solution of [4-(4-chloro-benzenesulfonyl)-4-(2,5-difluoro-phenyl)-cyclohexyl]-ethanesulfonyl chloride (60 mg, 0.12 mmol) (Example 105) in dichloromethane (5 mL) was added tert-butylamine (0.065 mL, 0.62 mmol), the mixture stirred at ambient temperature for 45 minutes, then evaporated. The residue was taken up in ethyl acetate (20 mL) and washed with 2N aqueous hydrochloric acid (20 mL) and brine (100 mL), dried (MgSO$_4$) and evaporated to

Example 108

4-[4-(4-Chloro-benzenesulfonyl)-4-(2,5-difluoro-phenyl)-cyclohexyl]-2-methanesulfonyl-butyric acid ethyl ester

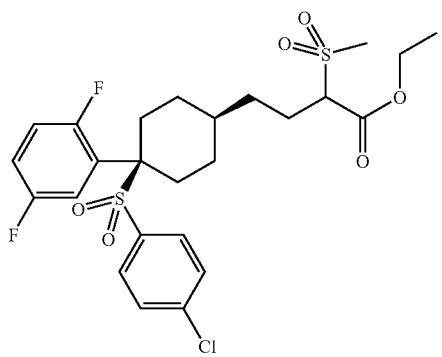

Ethyl methanesulfonylacetate (0.285 mL, 2.15 mmol) was added dropwise to a solution of sodium hydride (60% dispersion in mineral oil, 94 mg, 2.37 mmol) in N,N-dimethylformamide (7.0 mL) at 0° C. The reaction was stirred at 0° C. for one hour, before the addition of Intermediate F (1.13 g, 2.15 mmol) in N,N-dimethylformamide (2 mL). The reaction was stirred at 0° C. for a further 2 hours, then for a further 12 hours, warming gradually. The reaction was partitioned between diethyl ether (150 µL) and 1M aqueous hydrochloric acid (150 mL), the phases separated and the aqueous layer washed with diethyl ether. The combined organic layers were washed with 1N aqueous sodium hydrogencarbonate and brine, dried over MgSO$_4$ and concentrated. The residue was chromatographed using a Biotagem 40S column, eluting with 70/30 iso-hexane/acetone to give the title compound (769 mg).

$^1$H NMR (CDCl$_3$) δ 7.37 (4H, q, J=8.8, 10.9 Hz), 7.00–7.09 (2H, m), 6.79–6.86 (1H, m), 4.26–4.41 (2H, m), 3.76 (1H, dd, J=4.0, 10.7 Hz), 3.02 (3H, s), 2.40 (4H, s), 2.00–2.13 (2H, m), 1.72 (2H, d, J=13.7 Hz), 1.46–1.60 (5H, m), 1.38 (3H, t, J=7.2 Hz). MS (ES-) 561 ([M-H]$^-$).

Example 109

4-[4-(4-Chloro-benzenesulfonyl)-4-(2,5-difluoro-phenyl)-cyclohexyl]-2-methanesulfonyl-butyric acid

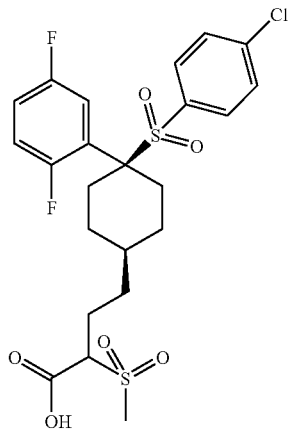

A solution of lithium hydroxide (21 mg, 0.88 mmol) in water (700 mL) was added to the product from Example 108 (100 mg, 0.18 mmol) in tetrahydrofuran (2 mL). The resulting mixture was stirred vigorously for 12 hours, then poured into 1M aqueous hydrochloric acid (20 mL) and extracted with ethyl acetate (2×40 mL). The combined organic layers were dried (NaSO$_4$), and concentrated. The residue was purified using column chromatography on silica, eluting with 95/5/0.5 dichloromethane/methanol/acetic acid to give the title compound (79 mg).

$^1$H NMR (CDCl$_3$) δ 7.30–7.37 (4H, m), 7.01–7.08 (2H, m), 6.79–6.86 (1H, m), 3.87 (1H, dd, J=3.9, 10.5 Hz), 3.10 (3H, s), 2.41 (4H, s), 2.05–2.14 (2H, m), 1.49–1.80 (7H, m). MS (ES-) 533 ([M-H]$^-$).

Example 110

3-[4-(4-Chloro-benzenesulfonyl)-4-(2,5-difluoro-phenyl)-cyclohexyl]-2-methanesulfonyl-propionic acid ethyl ester

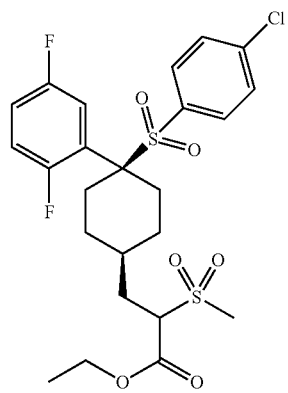

Prepared by the procedure of Example 108 using Intermediate E. MS (ES-) 547 ([M-H]$^-$).

Example 111

3-[4-(4-Chloro-benzenesulfonyl)-4-(2,5-difluoro-phenyl)-cyclohexyl]-2-methanesulfonyl-propionic acid

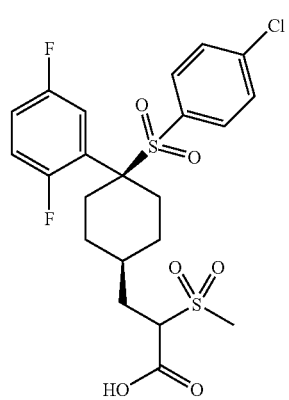

Obtained by hydrolysis of the product of Example 110 by the procedure of Example 109. MS (ES-) 519 ([M-H]$^-$).

Example 112

4-[4-(4-Chloro-benzenesulfonyl)-4-(2,5-difluoro-phenyl)-cyclohexyl]-2-ethyl-2-methanesulfonyl-butyric acid ethyl ester

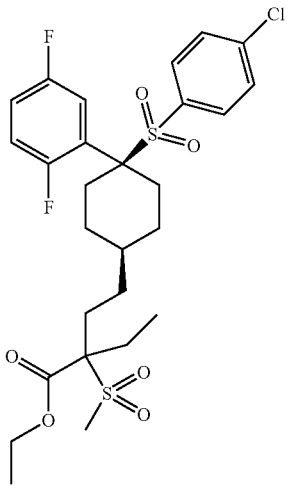

A solution of the product from Example 108 (620 mg, 1.10 mmol) in N,N-dimethylformamide (2.5 mL) was added dropwise to a solution of sodium hydride (60% dispersion in mineral oil, 48 mg, 1.21 mmol) in N,N-dimethylformamide (2.5 mL), and stirred for 45 minutes. Ethyl trifluoromethanesulfonate (0.140 mL, 1.10 mmol) was added dropwise and stirred for 14 hours at room temperature. The reaction was partitioned between diethyl ether (150 mL) and 1M aqueous hydrochloric acid (150 mL), the phases were separated and the aqueous layer extracted with diethyl ether. The combined organic layers were washed with 1N aqueous sodium hydrogencarbonate and brine, dried over $MgSO_4$ and concentrated. The residue was chromatographed using a Biotage™ 40S column, eluting with 70/30 iso-hexane/acetone to give the title compound (80 mg).

$^1$H NMR (CDCl$_3$) δ 7.32–7.38 (4H, m), 7.01–7.10 (2H, m), 6.80–6.87 (1H, m), 4.34 (2H, q, J=7.0 Hz), 3.04 (3H, s), 2.37–2.40 (4H, m), 2.20–2.28 (1H, m), 2.07–2.17 (3H, m), 1.75 (2H, dd, J=2.0, 11.3 Hz), 1.63–1.69 (1H, m), 1.46–1.53 (4H, m), 1.37 (3H, t, J=7.2 Hz), 1.09 (3H, t, J=7.4 Hz). MS (ES−) 589 ([M−H]$^−$).

Example 113

4-[4-(4-Chloro-benzenesulfonyl)-4-(2,5-difluoro-phenyl)-cyclohexyl]-2-ethyl-2-methanesulfonyl-butyric acid

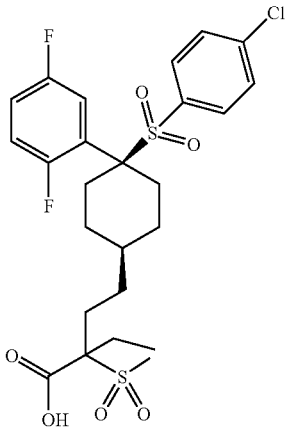

The product of Example 112 was hydrolyzed by the procedure of Example 109, except that heating to 50° C. was necessary.

$^1$H NMR (CD$_3$OD) δ 7.49 (2H, d, J=8.6 Hz), 7.40 (2H, d, J=8.6 Hz), 7.11–7.19 (2H, m), 6.94–7.00 (1H, m), 3.10 (3H, s), 2.46–2.50 (2H, m), 2.34 (2H, t, J=12.6 Hz), 2.10–2.19 (2H, m), 1.97–2.05 (2H, m), 1.65–1.78 (3H, m), 1.46–1.59 (4H, m), 1.07 (3H, t, J=7.5 Hz). MS (ES−) 561 ([M−H]$^−$).

Example 114

1-(4-Chlorophenylsulfonyl)-1-(2,5-difluoro-phenyl)-4-[(3-sulfonylmethyl)pentyl]-cyclohexane

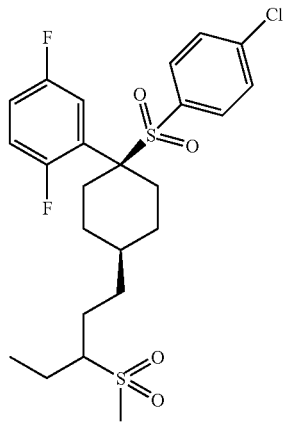

The product of Example 113 (22 mg, 0.037 mmol) and sodium chloride (5 mg, 0.082 mmol) were heated to reflux in 58% aqueous dimethylsulfoxide for 26 hours. The reaction was cooled to room temperature, poured into water and extracted with ethyl acetate (x2). The combined organic layers were dried (MgSO$_4$) and concentrated. The residue was purified using column chromatography on silica eluting with ethyl acetate:iso-hexane 1:4 to give the title compound (12 mg).

$^1$H NMR (CDCl$_3$) δ 7.31–7.38 (4H, m), 7.00–7.10 (2H, m), 6.79–6.87 (1H, m), 2.85 (3H, s), 2.71–2.76 (1H, m), 2.41 (4H, d, J=0.7 Hz), 1.51–2.04 (11H, m), 1.13 (3H, t, J=7.54 Hz). MS (ES+) 519 ([MH]$^+$).

Example 115

(2,2,2-Trifluoro-ethyl)-sulfamic acid 4-(2,5-difluoro-phenyl)-4-(4-trifluoromethyl-benzenesulfonyl)-cyclohexyl ester

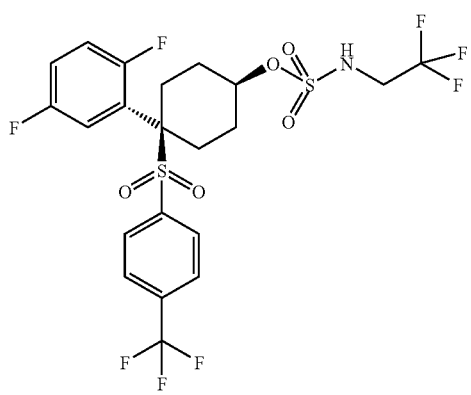

Intermediate O (200 mg, 0.48 mmol) in dry dichloromethane (4 mL) under nitrogen was treated with triethylamine (0.1 mL, 0.71 mmol) and trifluoroethyl sulfamoyl chloride (105 mg, 0.52 mmol). The reaction was stirred at room temperature for 18 h., diluted with dichloromethane, washed with water and brine, dried (MgSO$_4$) and evaporated. The residue was purified by flash chromatography on silica eluting with iso-hexane/ethyl acetate (2:1) to give a white solid (195 mg).

$^1$H NMR δ (ppm) (CDCl3): 1.50 (2H, m), 2.22 (1H, m), 2.26 (1H, m), 2.48–2.78 (4H, m), 3.77–3.79 (2H, m), 4.74 (1H, t, J=2.6 Hz), 4.98 (1H, d, J=2.6 Hz), 6.82–6.90 (1H, m), 7.06–7.14 (2H, m), 7.58 (2H, d, J=9 Hz), 7.68 (2H, d, J=9 Hz).

Example 116

Acetic acid 2-[4-(4-chloro-benzenesulfonyl)-4-(2,5-difluoro-phenyl)-cyclohexyloxysulfonylamino]-ethyl ester

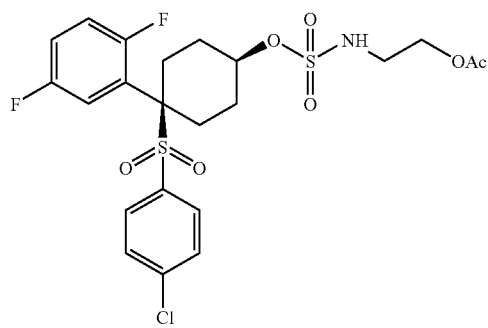

To a stirred solution of 2-(N-BOC-amino)ethanol (4.35 g, 27 mmol) in dichloromethane (50 mL) was added acetic anhydride (2.8 mL, 30 mmol), triethylamine (4.1 mL, 30 mmol) and dimethylaminopyridine (50 mg) and the reaction stirred at ambient temperature for one hour. The mixture was washed with 2N aqueous hydrochloric acid (50 mL) and brine (50 mL), dried (MgSO$_4$) and evaporated to leave a residue which was dissolved in ethyl acetate (100 mL). Hydrogen chloride gas was bubbled through for 5 minutes and the mixture stirred at ambient temperature for one hour. The resulting precipitate was filtered off and washed with ethyl acetate to leave 2-(aminoethyl)acetate hydrochloride salt (3.15 g).

To a stirred suspension of the foregoing acetate (607 mg, 4.3 mmol) in acetonitrile (20 mL) cooled to 0° C. was added sulfuryl chloride (1.05 mL, 13 mmol) and the mixture stirred at 70° C. for 20 hours. The solvent was evaporated to leave the crude sulfamoyl chloride as a solid which was used without further purification.

To a stirred solution of Intermediate G (122 mg, 0.32 mmol) in N,N-dimethylacetamide (10 mL) was added triethylamine (0.44 mL, 3.2 mmol) and crude sulfamoyl chloride from the foregoing step (320 mg, ca. 1.6 mmol) and the mixture stirred at ambient temperature for 2 hours. Further triethylamine (0.50 mL) and sulfamoyl chloride (300 mg) were added, the mixture warmed to 60° C. for 3 hours, then ethyl acetate (30 mL) was added and the solution washed with water (5×20 mL) and brine (20 mL), dried (MgSO$_4$) and evaporated to leave a residue which was purified by column chromatography on silica eluting with ethyl acetate:dichloromethane:iso-hexane 1:2:2, to afford the desired product (73 mg). MS (ES+) 574 ([MNa]$^+$).

Example 117

(2-Hydroxy-ethyl)-sulfamic acid 4-(4-chloro-benzenesulfonyl)-4-(2,5-difluoro-phenyl)-cyclohexyl ester

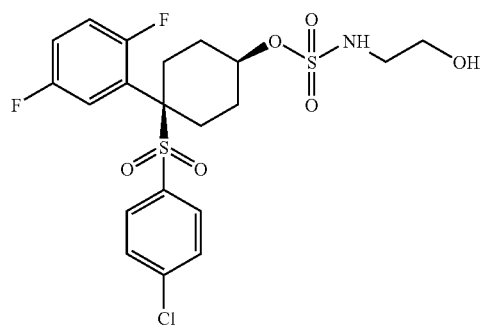

To a stirred solution of the product from Example 116 (54 mg, 0.1 mmol) in tetrahydrofuran (2 mL) was added lithium hydroxide (35 mg, 1.5 mmol) in water (2 mL) and the mixture stirred for 2 hours. Ethyl acetate (20 mL) was added, the solution washed with saturated aqueous ammonium chloride (10 mL), saturated aqueous sodium bicarbonate (10 mL) and brine (20 mL), dried (MgSO$_4$) and evaporated to leave a residue which was purified by column chromatography on silica eluting with ethyl acetate:iso-hexane 1:1, to afford the title compound. (33 mg).

$^1$H NMR (CDCl$_3$) δ 7.40–7.33 (4H, m), 7.12–7.05 (2H, m), 6.91–6.83 (1H, m), 5.07 (1H, t, J=6 Hz), 4.72 (1H, t, J=2.5 Hz), 3.84 (2H, q, J=5 Hz), 3.34 (2H, q, J=5 Hz), 2.70–2.50 (4H, m), 2.24 (2H, br d, J=15.5 Hz), 2.08 (1H, t, J=5 Hz) and 1.52–1.38 (2H, m). MS (ES+) 510 ([MH]$^+$).

Example 118

Sulfinamic acid 4-(4-chloro-benzenesulfonyl)-4-(2,5-difluoro-phenyl)-cyclohexyl ester

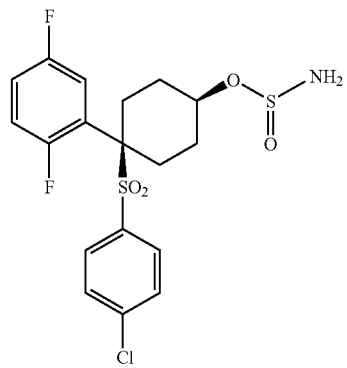

A solution of Intermediate G (100 mg, 0.26 mmol), in dichloromethane (3 mL) and pyridine (1 mL) was cooled to −78° C. and thionyl chloride added (47 mL). After two hours at −78° C., ammonia gas was bubbled through keeping the temperature at −78° C. After 20 minutes, the reaction vessel was sealed and left to stir for 19 hours slowly warming to room temperature. The mixture was then extracted into ethyl acetate, washed with water, dried (MgSO$_4$) and evaporated

Example 119

Sulfamic acid 4-(4-chloro-benzenesulfonyl)-4-(2,5-difluoro-phenyl)-cyclohexyl ester

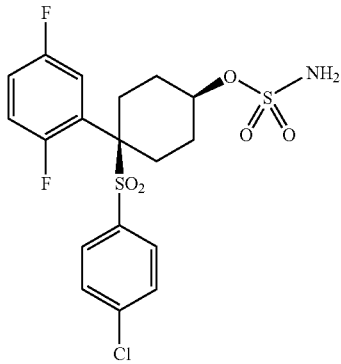

Intermediate G (1.45 g, 3.76 mmol) in N,N-dimethylacetamide (10 mL) at 0° C. was treated with sulfamoyl chloride (1.73 g, 15 mmol) (prepared as in DE 19740785) and the reaction stirred at room temperature for 90 minutes. The reaction was then diluted with ethyl acetate, washed with water, dried (MgSO$_4$) and evaporated to an oil which crystallised on standing (1.7 g).

$^1$H NMR (360 MHz, CDCl$_3$) δ 7.40–7.35 (4H, m), 7.1–7.02 (2H, m), 6.90–6.80 (1H, m), 5.13 (2H, s), 4.75–4.74 (1H, m) 2.59–2.50 (4H, m), 2.30–2.24 (2H, m), 1.50–1.40 (2H, m). MS (ES+) 488 ([MNa]$^+$).

Example 120

Sulfamic acid 4-(2,5-difluoro-phenyl)-4-(4-trifluoromethyl-benzenesulfonyl)-cyclohexyl ester

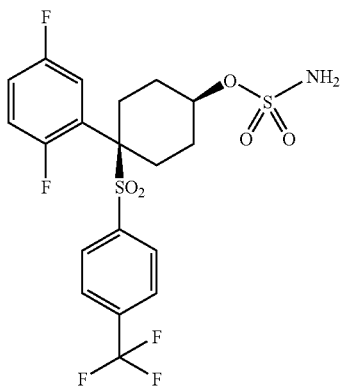

Prepared from Intermediate O by the procedure of Example 119.
MS (ES+) 522 ([MNa]$^+$).

Example 121

Dimethyl-sulfamic acid 4-(4-chloro-benzenesulfonyl)-4-(2,5-difluoro-phenyl)-cyclohexyl ester

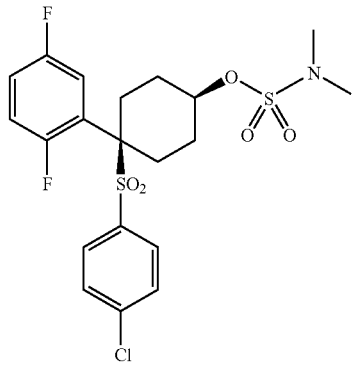

To a solution of the product of Example 119 (108 mg, 0.23 mmol) in tetrahydrofuran (2 mL) cooled to −78° C. was added lithium bis(trimethylsilyl)amide (1M solution in tetrahydrofuran, 561 μL). After stirring for 1 hour at −78° C., methyl iodide (84 μL, 1.4 mmol) was added, the reaction stirred at −78° C. for 2 hours then at room temperature for 2 hours, quenched with water (10 mL), extracted into ethyl acetate, dried (MgSO$_4$) and evaporated to an oil. The product was purified by flash chromatography on silica eluting with 50% diethyl ether/iso-hexane to yield desired product (51 mg). MS (ES+) 516 ([MNa]$^+$).

Example 122

Ethyl-sulfamic acid 4-(4-chloro-benzenesulfonyl)-4-(2,5-difluoro-phenyl)-cyclohexyl ester

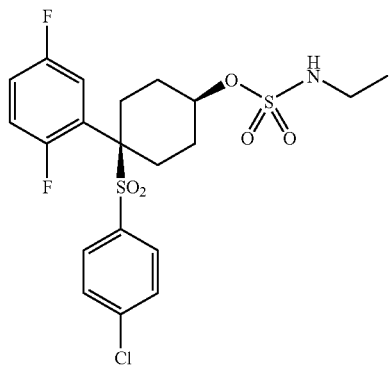

Prepared as for Example 119 using N-ethyl sulfamoyl chloride (prepared as in *JOC*. 1976, 41) to obtain a white solid which was purified by flash chromatography on silica eluting with 30% ethyl acetate/iso-hexane.
MS (ES+) 516 ([MNa]$^+$).

Example 123

(2,2,2-Trifluoro-ethyl)-sulfamic acid 4-(4-chloro-benzenesulfonyl)-4-(2,5-difluoro-phenyl)-cyclohexyl ester

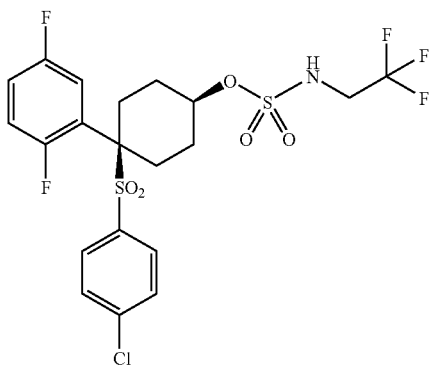

Prepared as for Example 119 using 2,2,2-trifluoroethyl sulfamoyl chloride (prepared as in DE 3429048) to obtain a colourless oil which was purified by flash chromatography on silica eluting with 30% ethyl acetate/iso-hexane.
MS (ES−) 546 ([MH]⁻).

Example 124

Tert-butyl-sulfamic acid 4-(4-chloro-benzenesulfonyl)-4-(2,5-difluoro-phenyl)-cyclohexyl ester

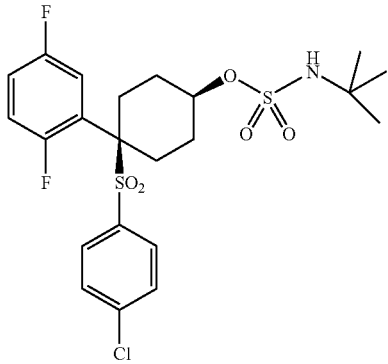

Prepared as for Example 119 using tert-butyl sulfamoyl chloride (prepared as in *J. Heterocyclic Chem* 2000, 773).
MS (ES−) 520 ([MH]⁻).

Example 125

Acetyl-sulfamic acid 4-(4-chloro-benzenesulfonyl)-4-(2,5-difluoro-phenyl)-cyclohexyl ester

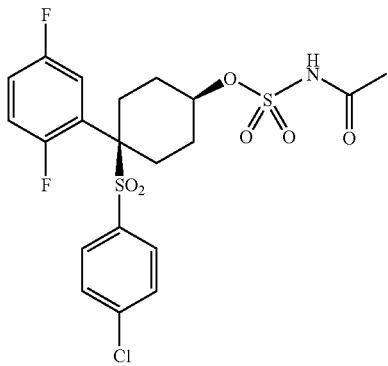

A solution of the product from Example 119 (69 mg, 0.15 mmol) in pyridine (2 mL) was treated with acetic anhydride (2 μL) at room temperature. After stirring for 2.5 hours, ice was added to the mixture until a white precipitate formed. The mixture was extracted with ethyl acetate, washed with water and brine, dried (MgSO₄) and evaporated. The product was purified by flash chromatography on silica eluting with 50% ethyl acetate/iso-hexane to obtain the title compound as a white solid (14 mg). MS (ES+) 530 ([MNa]⁺).

Example 126

Sulfamic acid 4-(2,5-difluoro-phenyl)-4-(6-trifluoromethyl-pyridine-3-sulfonyl)-cyclohexyl ester

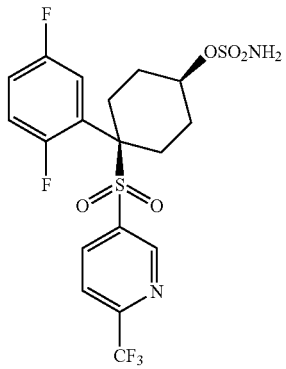

4-(2,5-Difluoro-phenyl)-4-(6-trifluoromethyl-pyridine-3-sulfonyl)-cyclohexanone (Intermediate T, steps 1–4) (100 mg, 0.24 mmol) in tetrahydrofuran (2 mL) at −78° C. was treated with L-Selectride™ (1M in tetrahydrofuran, 0.24 μL, 0.24 mmol). The reaction mixture was stirred for 2 h., quenched with 2 N aqueous hydrochloric acid, diluted with diethyl ether, warmed to room temperature, then partitioned between diethyl ether and water. The organic layer washed with water, dried (MgSO₄) and evaporated in vacuo. Purification by column chromatography on silica gave the axial (cis) alcohol (68 mg, 67%) as a white solid. $^1$H NMR (400 MHz, d₆-DMSO) δ 8.68 (1H, s), 8.15–8.13 (2H, m), 7.39–7.12 (3H, m), 4.63 (1H, d, J=2.7 Hz), 3.74–3.68 (1H, m), 2.70–2.40 (4H, m), 1.75–1.68 (2H, m), 1.30–1.20 (2H, m).

This alcohol (100 mg, 0.24 mmol) in N,N-dimethylacetamide (5 ml) was treated with sulfamoyl chloride (111 mg, 0.96 mmol) and stirred at room temperature for 2 days. The reaction mixture was evaporated in vacuo and purified by chromatography on silica to give the desired product (35 mg, 29%) as a white solid. MS (ES+) 501 ([MH]⁺).

Example 127

2-[4-(4-Chloro-benzenesulfonyl)-4-(2,5-difluoro-phenyl)-cyclohexyl]-1-(2,2-difluoro-benzo[1,3]dioxol-4-yl)-ethanone

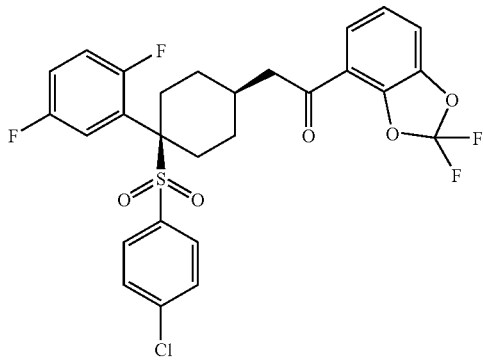

The Grignard reagent derived from 3-bromo-1,2-(difluoromethylenedioxy)-benzene (5.5 ml 0.28M solution in THF, 1.5 mmol) was added dropwise to a cooled solution at 0° C. of Intermediate H (130 mg, 0.28 mmol) in THF (10 mL) under nitrogen. The resulting mixture was stirred at 0° C. for 1.5 h, left to warm to room temperature for 16 h., diluted with water and extracted with ethyl acetate. The combined organic layers were washed with brine, dried (MgSO$_4$) and evaporated to leave a residue which was purified by preparative thin layer chromatography eluting with diethyl ether:dichloromethane:iso-hexane 1:1:6 to afford the desired product (32 mg).

$^1$H NMR (CDCl$_3$) δ 7.65–7.63 (1H, dd, J=8.2, 1.4 Hz), 7.36–7.35 (4H,m), 7.26 (1H, dd, J=8.2, 1.2 Hz), 7.20–7.18 (1H, t, J=8.0 Hz), 7.10–7.00 (2H, m), 6.87–6.80 (1H, m), 3.13–3.11 (2H, d, J=6.9 Hz), 2.47 (4H, m), 2.38–2.32 (1H, m), 1.84–1.79 (2H, m) and 1.65–1.56 (2H, m). MS (ES+) 393 ([M-ArSO$_2^-$]$^+$), 591 ([MNa]$^+$).

Example 128

1-(3-Allyloxy-phenyl)-2-[4-(4-chloro-benzenesulfonyl)-4-(2,5-difluoro-phenyl)-cyclohexyl]-ethanone

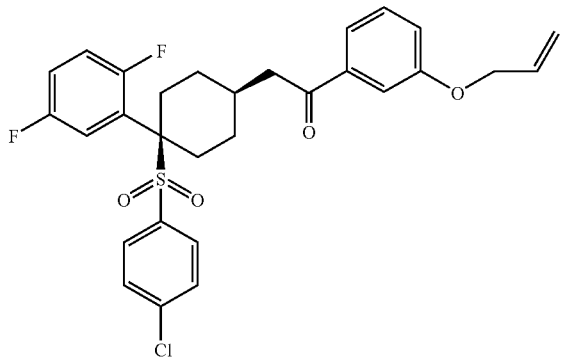

Prepared from 3-allyloxy-bromobenzene by the procedure used in Example 127.

$^1$H NMR (CDCl$_3$) δ 7.55–7.50 (2H, m), 7.42–7.31 (5H, m), 7.16–7.00 (3H, m), 6.86–6.79 (1H, m), 6.12–6.03 (1H, m), 5.47 (1H, d, J=12.5 Hz), 5.34–5.31 (1H, dd, J=10.6, 1.5 Hz), 4.62–4.60 (2H, m), 3.11–3.10 (2H, d, J=7.0 Hz), 2.48–2.46 (5H, m), 1.80–1.75 (2H, m) and 1.62–1.57 (2H, m).

MS (ES+) 567 ([MNa]$^+$).

Example 129

(2-{2-[4-(4-Chloro-benzenesulfonyl)-4-(2,5-difluoro-phenyl)-cyclohexyl]-acetyl}-phenoxy)-acetic acid methyl ester

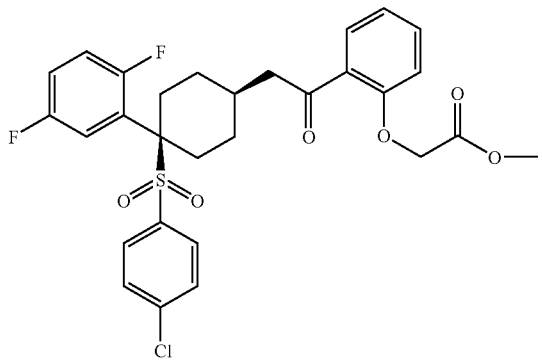

The procedure of Example 127 was followed, using 2-allyloxy-bromobenzene. Cleavage of the allyl group took place during the reaction, giving 2-[4-(4-chloro-benzenesulfonyl)-4-(2,5-difluoro-phenyl)-cyclohexyl]-1-(2-hydroxy-phenyl)-ethanone as the product.

To a stirred solution of this phenol (100 mg, 0.20 mmol) in acetone (10 mL) under nitrogen was added methyl bromoacetate (21 µL, 0.22 mmol) and potassium carbonate (55 mg, 0.40 mmol). The mixture was heated to reflux for 14 h., cooled to room temperature, filtered and the filtrate evaporated to afford a residue (100 mg) which was purified using preparative thin layer chromatography eluting with diethyl ether:dichloromethane:iso-hexane 1:1:5 to give the desired product (25 mg).

$^1$H NMR (CDCl$_3$) δ 7.67–7.65 (1H, dd, J=7.7, 1.8 Hz), 7.47–7.42 (1H, m), 7.36–7.30 (4H, m), 7.08–7.00 (3H, m), 6.85–6.79 (2H, m), 4.80 (2H, s), 3.86 (3H, s), 3.32–3.30 (2H, d, J=7.2 Hz), 2.46–2.38 (5H, m), 1.78–1.74 (2H, m) and 1.53–1.48 (2H, m). MS (ES+) 401 ([M-ArSO$_2^-$]$^+$), 599 ([MNa]$^+$).

Example 130

(2-{2-[4-(4-Chloro-benzenesulfonyl)-4-(2,5-difluoro-phenyl)-cyclohexyl]-acetyl}-phenoxy)-acetic acid

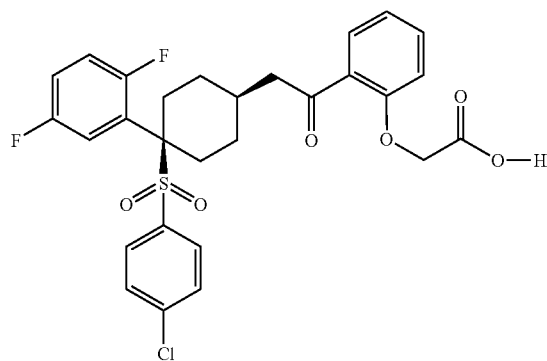

The product from Example 129 (70 mg, 0.12 mmol) in 2:1 tetrahydrofuran:water (6 mL) was stirred under nitrogen and lithium hydroxide (12 mg, 0.49 mmol) added. After 2 hours, the reaction was acidified and extracted with ethyl acetate. The combined organic layers were washed with brine, dried (MgSO$_4$) and evaporated to leave a residue which was purified by preparative thin layer chromatography eluting with diethyl ether:dichloromethane:iso-hexane 1:1:1 to afford the desired product (54 mg).

$^1$H NMR (CDCl$_3$) δ 7.79–7.77 (1H, dd, J=7.8, 1.7 Hz), 7.56–7.51 (1H, m), 7.36–7.28 (4H, m), 7.18–7.12 (1H, m), 7.08–6.94 (3H, m), 6.85–6.79 (1H, m), 4.77 (2H, s), 3.31–3.30 (2H, d, J=6.9 Hz), 2.46–2.41 (5H, m), 1.78–1.74 (2H, m), and 1.60–1.50 (2H, m). MS (ES+) 563 ([MH]$^+$), 387 ([M-ArSO$_2$]$^+$).

Example 131

2-[4-(4-Chloro-benzenesulfonyl)-4-(2,5-difluoro-phenyl)-cyclohexyl]-1-{3-[2-(1,1-dioxo-thiomorpholin-4-yl)-ethoxy]-phenyl}-ethanone

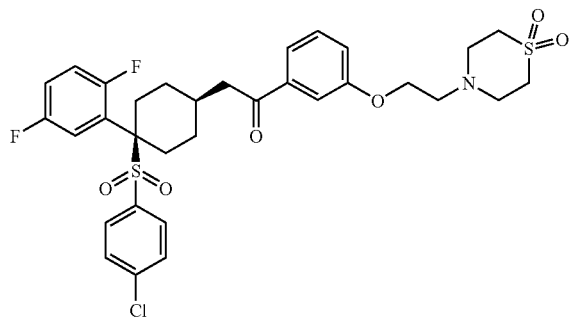

A stirred solution of the product from Example 128 (59 mg, 0.11 mmol) in 1:5 methanol:dichloromethane (12 mL) under nitrogen was cooled to −78° C. whilst oxygen was bubbled through. After 10 minutes stirring, ozone was bubbled into the solution until the reaction turned blue, then the mixture was purged with oxygen followed by nitrogen for 5 minutes. Dimethyl sulfide was added (83 µL, 1.14 mmol) and the reaction was warmed to ambient temperature over 90 minutes. Evaporation left a residue which was purified by preparative thin layer chromatography eluting with 2% methanol/dichloromethane to give the aldehyde derivative (44 mg).

To a stirred solution of this aldehyde (44 mg, 0.08 mmol.) and 1,1-dioxothiomorpholine (81 mg, 0.47 mmol) in methanol/dichloromethane (5 mL) was added triethylamine (40 µL, 0.27 mmol). The reaction mixture was stirred for 30 minutes followed by a dropwise addition of hydrochloric acid (0.12 mL of 3M solution in methanol, 0.36 mmol). The reaction was stirred for a further 30 minutes, then a solution of sodium cyanoborohydride (3.5 mg, 0.05 mmol) in methanol (0.1 mL) was added. The reaction mixture was stirred under nitrogen at ambient temperature for 16 h, the solvent evaporated, the residue taken up in 4N aqueous sodium hydroxide and extracted with diethyl ether. The combined organic layers were washed with water, dried (MgSO$_4$) and evaporated to give a residue (57 mg) which was purified by preparative thin layer chromatography eluting with diethyl ether:dichloromethane:iso-hexane 1:2:1 to afford the desired product (19 mg).

$^1$H NMR (CDCl$_3$) δ 7.60–7.58 (1H, d, J=7.7 Hz), 7.49–7.48 (1H, m), 7.43–7.29 (5H, m), 7.13–7.11 (1H, m), 7.09–7.01 (2H, m), 6.86–6.80 (1H, m), 4.18–4.15 (2H, t, J=5.2 Hz), 3.20–3.08 (10H, m), 3.04–3.02 (2H, t, J=5.3 Hz), 2.52–2.39 (5H, m), 1.80–1.75 (2H, m) and 1.62–1.50 (2H, m). MS (ES+) 666 ([MH]$^+$), 490 ([M-ArSO$_2^-$]$^+$).

Example 132

4-(2-{2-[4-(4-Chloro-benzenesulfonyl)-4-(2,5-difluoro-phenyl)-cyclohexyl]-acetyl}-phenoxy)-butyric acid

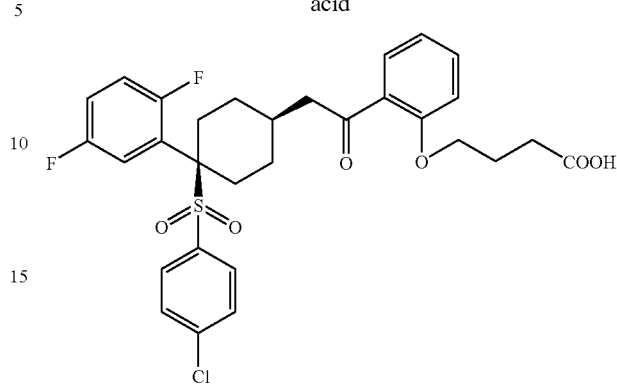

To a stirred solution of 2-[4-(4-chloro-benzenesulfonyl)-4-(2,5-difluoro-phenyl)-cyclohexyl]-1-(2-hydroxy-phenyl)-ethanone (Example 129, first step) (32 mg, 0.06 mmol) in N,N-dimethylformamide (5 mL) under nitrogen was added sodium hydride (10 mg of 60% suspension in oil, 0.42 mmol), followed by methyl-4-chlorobutyrate (2 eq.). The reaction mixture was stirred for 2 days at 50° C., then cooled to room temperature, diluted with water and extracted with ethyl acetate. The combined organic layers were washed with brine, dried (MgSO$_4$) and evaporated to give a residue (44 mg) which was used in the next step without further purification. To a stirred solution of the methyl ester intermediate from above (16 mg, 0.03 mmol) in 2:1 tetrahydrofuran:water (6 mL) under nitrogen was added lithium hydroxide (2.5 mg, 0.11 mmol) and the mixture was stirred at ambient temperature for 3 h. The reaction was acidified and extracted with ethyl acetate, and the combined organic layers washed with brine, dried (MgSO$_4$) and evaporated to leave a residue which was purified by preparative thin layer chromatography eluting with ethyl acetate:iso-hexane 1:1 to afford the desired product (10 mg).

$^1$H NMR (CDCl$_3$) δ 7.65–7.63 (1H, d, J=7.1 Hz), 7.46–7.43 (1H, t, J=7.2 Hz), 7.36–7.29 (4H, m), 7.02–6.96 (4H, m), 6.85–6.82 (1H, m), 4.20 (2H, t, J=6.2 Hz), 3.20–3.18 (2H, d, J=6.7 Hz), 2.68–2.62 (2H, t, J=7.2 Hz), 2.44–2.41 (5H, m), 2.27 (2H, br, s), 1.75–1.72 (2H, m) and 1.53–1.50 (2H, m).

Example 133

2-[4-(4-Chloro-benzenesulfonyl)-4-(2,5-difluoro-phenyl)-cyclohexyl]-1-(1-oxy-pyridin-2-yl)-ethanone

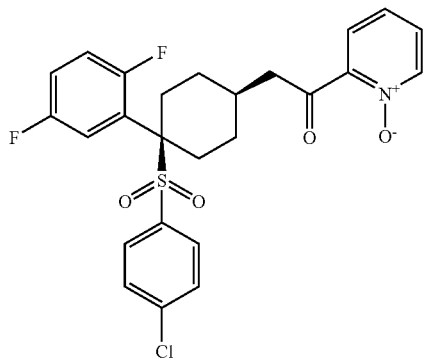

To a stirred solution of 2-pyridyllithium [prepared in situ from 2-bromopyridine (0.15 mL, 1.59 mmol) and nBuLi (1 mL of 1.6M solution in hexane, 1.59 mmol) in diethyl ether (10 mL) stirring under nitrogen at −78° C. for 30 minutes] was added dropwise Intermediate H (250 mg, 0.53 mmol) in diethyl ether (5 mL). The reaction mixture was stirred at −78° C. for a further 2 h, allowed to warm to room temperature for 2 h, then diluted with water and extracted with ethyl acetate. The combined organic layers were washed with water, dried (MgSO₄) and evaporated to give a residue (391 mg) which was purified by preparative thin layer chromatography eluting with diethyl ether:dichloromethane:iso-hexane 1:1:3 and 1% triethylamine to afford the 2-keto-pyridine intermediate (200 mg).

¹H NMR (CDCl₃) δ 8.72–8.71 (1H, d, J=4.3 Hz), 8.04–8.02 (1H, d, J=7.9 Hz), 7.86–7.82 (1H, m), 7.51–7.47 (1H, m), 7.38–7.32 (4H, m), 7.10–7.01 (2H, m), 6.87–6.80 (1H, m), 3.42–3.40 (2H, d, J=7.1 Hz), 2.54–2.40 (5H, m), 1.79–1.75 (2H, m) and 1.59–1.55 (2H, m)

To a stirred solution of the ketopyridine from the foregoing step (40 mg, 0.08 mmol) under nitrogen in dichloromethane (10 mL) was added urea hydrogen peroxide (15.4 mg, 0.16 mmol). The reaction mixture was cooled to 0° C. followed by a dropwise addition of trifluroacetic anhydride (23 μL, 0.16 mmol). The reaction mixture was then left to warm to ambient temperature over 1 h, quenched with sodium sulfite, diluted with water and extracted with dichloromethane. The combined organic layers were washed with water, dried (MgSO₄) and evaporated to give a residue (35 mg) which was purified by preparative thin layer chromatography eluting with ethyl acetate to afford the desired product (16 mg).

¹H NMR (CDCl₃) δ 8.21–8.19 (1H, d, J=6.4 Hz), 7.60–7.58 (1H, d, J=7.7 Hz), 7.40–7.29 (6H, m), 7.08–7.01 (2H, m), 6.86–6.79 (1H, m), 3.37–3.35 (2H, d, J=7.0 Hz), 2.46–2.39 (5H, m), 1.81–1.77 (2H, m) and 1.60–1.50 (2H, m). MS (ES+) 330 ([M-ArSO₂⁻]⁺), 506 ([MH]⁺), 528 ([MNa]⁺).

Example 134

1-[4-(4-Chloro-benzenesulfonyl)-4-(2,5-difluorophenyl)-cyclohexyl]-3-methanesulfonyl-propan-2-one

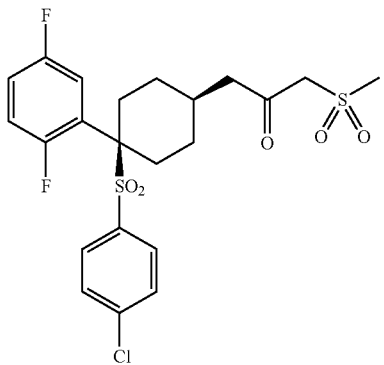

A solution of diisopropylamine (100 μL, 1.35 mmol) in tetrahydrofuran (3 mL) was cooled to −78° C. and butyllithium (400 μL, 1.35 mmol) was added dropwise. The resulting solution was warmed to 0° C., re-cooled to −78° C. and a solution of methyl sulfone (70 mg, 1.3 mmol) in tetrahydrofuran (1 mL) added. After 15 minutes at −78° C. a solution of Intermediate B (70 mg, 0.44 mmol) in tetrahydrofuran (1 mL) was added. The reaction was stirred at −78° C. for 30 minutes then at ambient temperature for 1 hour, quenched with saturated aqueous ammonium chloride solution and extracted into ethyl acetate. The dried (MgSO₄) extracts were evaporated and the residue purified by column chromatography on silica eluting with 35% ethyl acetate/iso-hexane to yield a white solid (30 mg).

¹H NMR (400 MHz, CDCl₃) δ 7.37–7.29 (4H, m), 7.06–7.01 (2H, m), 6.86–6.79 (1H, m), 4.05 (2H, s), 3.05 (3H, s), 2.89–2.87 (2H, d, J=7 Hz), 2.46–2.26 (5H, m), 1.72–1.51 (4H, m). MS (ES+) 505 ([MH]⁺).

Example 135

1-[4-(4-Chloro-benzenesulfonyl)-4-(2,5-difluorophenyl)-cyclohexyl]-3-methanesulfonyl-3-methylbutan-2-one

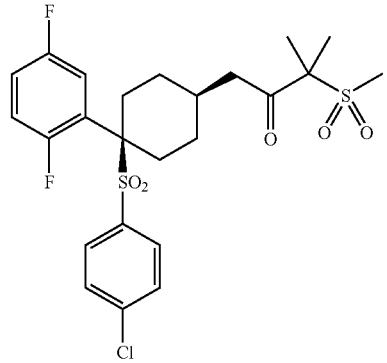

The product from Example 134 (50 mg, 0.099 mmol) in 1,2-dimethoxyethane (3 mL) was treated with sodium hydride (60% dispersion in mineral oil, 8 mg, 0.19 mmol) at room temperature. After stirring for 1.5 hours, methyl iodide (24 μL, 0.40 mmol) was added and the reaction stirred for 18 hours, then quenched with saturated aqueous ammonium chloride solution. The reaction was then extracted into ethyl acetate, dried (MgSO₄) and evaporated to a white solid which was purified by column chromatography on silica eluting with 35% ethyl acetate/iso-hexane to yield the desired product as a white solid (1 mg).

¹H NMR (400 MHz, CDCl₃) δ 7.37–7.29 (4H, m), 7.06–7.01 (2H, m), 6.86–6.79 (1H, m), 2.90–2.87 (5H, m), 2.41–2.20 (5H, m), 1.7–1.63 (8H, m), 1.59–1.49 (2H, m). MS (ES+) 555 ([MNa]⁺).

Example 136

1-[4-(4-Chloro-benzenesulfonyl)-4-(2,5-difluorophenyl)-cyclohexyl]-3-methanesulfonyl-butan-2-one

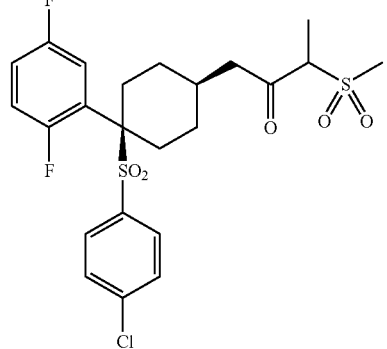

The product from Example 134 (28 mg, 0.056 mmol) in 1,2-dimethoxyethane (3 mL) was treated with sodium hydride (60% dispersion in mineral oil, 2 mg, 0.056 mmol) at room temperature. After stirring for 1.5 hours, methyl iodide (6 μL, 0.056 mmol) was added and the reaction stirred for 18 hours, then quenched with saturated aqueous ammonium chloride solution. The reaction was then extracted into ethyl acetate, dried (MgSO$_4$) and evaporated to a white solid which was purified by column chromatography on silica eluting with 35% ethyl acetate/iso-hexane to yield the desired product as a white solid (13 mg).

$^1$H NMR (400 MHz, CDCl$_3$) δ 7.37–7.29 (4H, m), 7.06–7.01 (2H, m), 6.86–6.79 (1H, m), 4.04–3.99 (1H, q, J=4 Hz), 3.09–3.03 (1H, dd, J=8, 20 Hz), 2.88 (3H, s), 2.80–2.73 (1H, dd, J=8, 20 Hz), 2.44–2.26 (5H, m), 1.71–1.64 (2H, m), 1.61–1.59 (3H, d, J=8 Hz) and 1.59–1.49 (2H, m).

MS (ES+) 541 ([MNa]$^+$).

Example 137

2-[4-(4-Chloro-benzenesulfonyl)-4-(2,5-difluoro-phenyl)-cyclohexyl]-1-(1,1-dioxo-tetrahy-drothiophen-2-yl)-ethanone

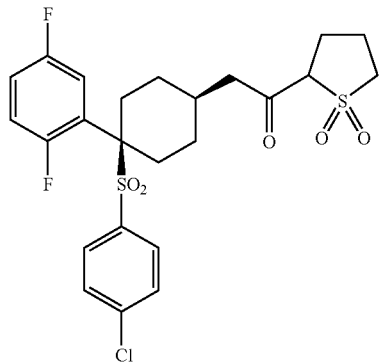

Prepared by the procedure of Example 134 using tetramethyl sulfone.

$^1$H NMR (400 MHz, CDCl$_3$) δ 7.38–7.32 (4H, m), 7.07–7.01 (2H, m), 6.87–6.79 (1H, m), 4.06–4.02 (1H, t, J=7 Hz), 3.18–2.99 (3H, m), 2.71–2.05 (10H, m), 1.74–1.70 (2H, m) and 1.60–1.49 (2H, m). MS (ES+) 553 ([MNa]$^+$).

Example 138

2-[4-(4-Chloro-benzenesulfonyl)-4-(2,5-difluoro-phenyl)-cyclohexyl]-1-(5-hydroxymethyl-furan-2-yl)-ethanone

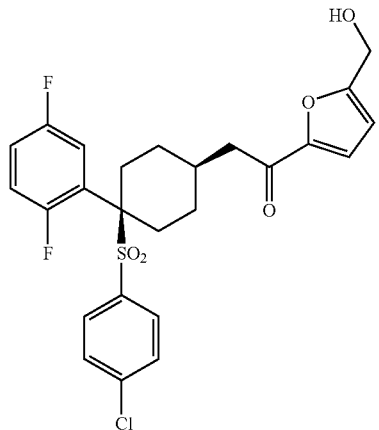

A solution of furfuryl alcohol (0.8 mL, 0.85 mmol) in tetrahydrofuran (3 mL) was cooled to −78° C. and treated with butyllithium (1M solution in hexane, 1.17 mL). After stirring at −78° C. for 1 hour, then at 0° C. for 1 hour, the reaction was re-cooled to −78° C. and a solution of Intermediate H (100 mg, 0.21 mmol) in tetrahydrofuran (1 mL) was added slowly over 20 minutes. The reaction was stirred and allowed to warm to room temperature over 20 hours, quenched with saturated aqueous ammonium chloride solution and extracted into ethyl acetate, washed with brine, dried and evaporated to an oil which was purified by column chromatography on silica eluting with 50% ethyl acetate/iso-hexane (80 mg). MS (ES+) 531 ([MNa]$^+$).

Example 139

5-{2-[4-(4-Chloro-benzenesulfonyl)-4-(2,5-difluoro-phenyl)-cyclohexyl]-acetyl}-furan-2-carbaldehyde

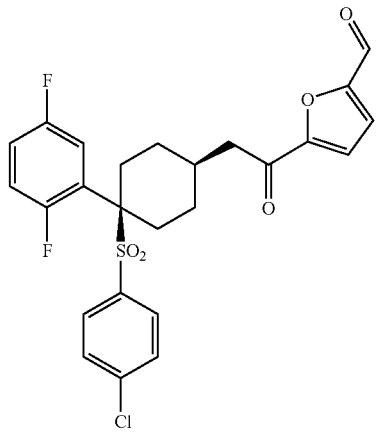

To a solution of the product from Example 138 (179 mg, 0.35 mmol) in dichloromethane (17 mL) was added Dess-Martin periodinane (374 mg, 0.88 mmol). The reaction was stirred at room temperature for one hour, filtered through Celite®, evaporated, and the residue purified by column chromatography on silica to afford the desired product (94 mg) as a white solid. MS (ES+) 507 ([MH]$^+$).

Example 140

5-{2-[4-(4-Chloro-benzenesulfonyl)-4-(2,5-difluoro-phenyl)-cyclohexyl]-acetyl}-furan-2-carboxylic acid

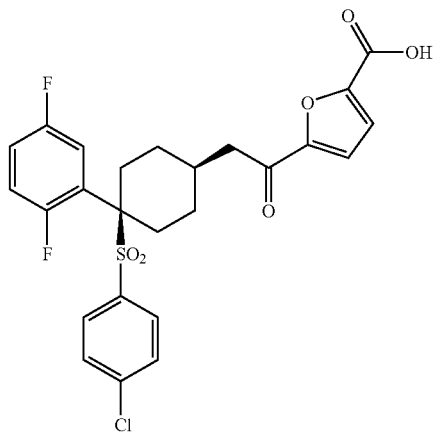

To a solution of the product from Example 139 (29 mg, 0.057 mmol) in dichloromethane (2 mL) and water (1 mL) cooled to 0° C. was added sulfamic acid followed by sodium chlorite. The reaction was left to stir, warming to room temperature over 2.5 hours. The layers were separated and the aqueous layer extracted further with dichloromethane. The combined organic layers were dried (MgSO$_4$) and evaporated to a cream foam, which was purified by column chromatography on silica (50% ethyl acetate/49% dichloromethane/1% acetic acid) to obtain a white solid (10 mg).

¹H NMR (400 MHz, CDCl₃) δ 7.35–7.17 (6H, m), 7.10–6.99 (2H, m), 6.87–6.78 (1H, m), 3.11–3.03 (2H, m), 2.55–2.20 (5H, m), 1.79–1.70 (2H, m), 1.60–1.50 (2H, m). MS (ES+) 523 ([MH]⁺).

Example 141

3-(5-{2-[4-(4-Chloro-benzenesulfonyl)-4-(2,5-difluoro-phenyl)-cyclohexyl]-acetyl}-furan-2-yl)-acrylic acid ethyl ester

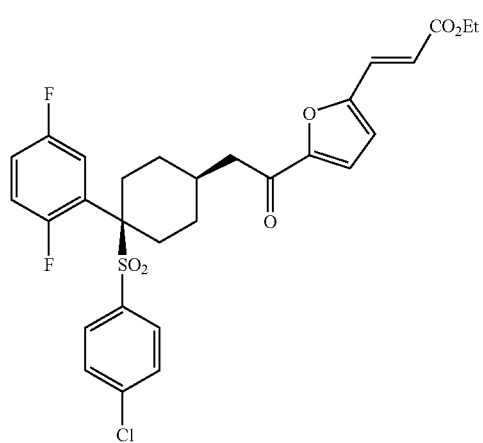

To a suspension of sodium hydride (60% dispersion, 10 mg) in tetrahydrofuran (4 mL) was added triethyl phosphonoacetate (0.25 mmol.) After stirring at room temperature for 1 hour a solution of the product from Example 139 (59 mg, 0.11 mmol) in tetrahydrofuran (2 mL) at 0° C. was added. After stirring at room temperature for another hour the reaction was quenched with water and extracted into ethyl acetate, dried (MgSO₄) and evaporated. The product was purified by column chromatography on silica eluting with 30% ethyl acetate/hexane to afford 15 mg of the desired product as a white solid. MS (ES+) 577 ([MH]⁺).

Example 142

2-[4-(4-Chloro-benzenesulfonyl)-4-(2,5-difluoro-phenyl)-cyclohexyl]-1-(3-hydroxymethyl-furan-2-yl)-ethanone

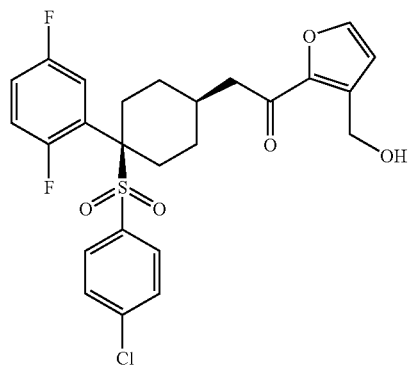

Prepared from 3-(hydroxymethyl)furan (167 mg, 1.7 mmol), following the procedure of Example 138. Column chromatography on silica eluting with ethyl acetate:iso-hexane 1:1, afforded the desired compound (62 mg) still contaminated with a little 3-(hydroxymethyl)furan. A pure sample was obtained by further careful chromatography on silica eluting with ethyl acetate:iso-hexane 2:3.

¹H NMR (CDCl₃) δ 7.52 (1H, d, J=1.5 Hz), 7.38–7.31 (4H, m), 7.09–7.01 (2H, m), 6.86–6.79 (1H, m), 6.55 (1H, d, J=1.5 Hz), 4.71 (2H, d, J=7 Hz), 4.26 (1H, t, J=7 Hz), 3.08 (2H, d, J=7.0 Hz), 2.47 (4H, m), 2.36 (1H, m), 1.78–1.73 (2H, m) and 1.6–1.5 (2H, m). MS (ES+) 509 ([MH]⁺).

Example 143

2-{2-[4-(4-Chloro-benzenesulfonyl)-4-(2,5-difluoro-phenyl)-cyclohexyl]-acetyl}-furan-3-carbaldehyde

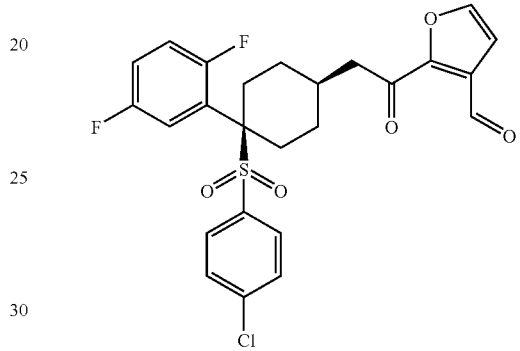

Prepared from the product of Example 142 (46 mg, 0.09 mmol) following the procedure of Example 139. The product was purified by column chromatography on silica eluting with diethyl ether:dichloromethane:iso-hexane 1:1:3 to afford the desired compound (27 mg).

¹H NMR (CDCl₃) δ 10.54 (1H, s), 7.55 (1H, d, J=1.5 Hz), 7.38–7.31 (4H, m), 7.09–7.02 (2H, m), 6.97 (1H, d, J=1.5 Hz), 6.87–6.82 (1H, m), 3.14 (2H, d, J=7.0 Hz), 2.48 (4H, m), 2.40 (1H, m), 1.81–1.76 (2H, m) and 1.62–1.55 (2H, m). MS (ES+) 529 ([MNa]⁺).

Example 144

2-{2-[4-(4-Chloro-benzenesulfonyl)-4-(2,5-difluoro-phenyl)-cyclohexyl]-acetyl}-furan-3-carboxylic acid

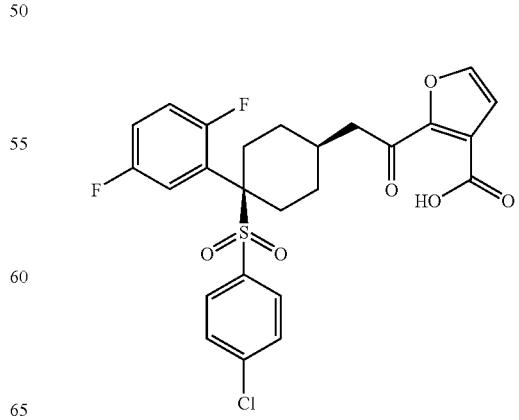

Prepared from the product of Example 143 (24 mg, 0.05 mmol) by the procedure of Example 140. Yield 26 mg.

¹H NMR (CDCl₃) δ 7.68 (1H, s), 7.4–7.2 (5H, m), 7.09–7.03 (2H, m), 6.87–6.80 (1H, m), 3.25 (2H, d, J=7.0 Hz), 2.55–2.35 (5H, m), 1.82–1.77 (2H, m) and 1.65–1.58 (2H, m). MS (ES+) 523 ([MH]⁺).

Example 145

3-(2-{2-[4-(4-Chloro-benzenesulfonyl)-4-(2,5-difluoro-phenyl)-cyclohexyl]-acetyl}-furan-3-yl)-acrylic acid ethyl ester

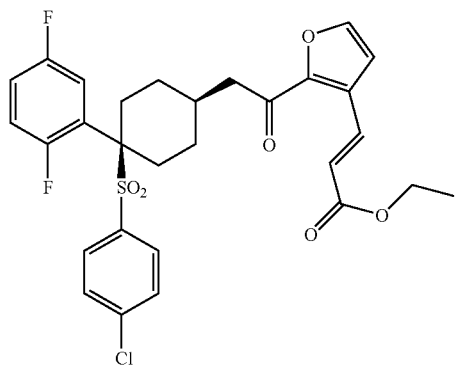

Prepared from the product of Example 143 by the procedure of Example 141. MS (ES+) 577 ([MH]⁺).

Example 146

3-(2-[2-{4-(4-Chloro-benzenesulfonyl)-4-(2,5-difluoro-phenyl)-cyclohexyl]-acetyl}-furan-3-yl)-propionic acid ethyl ester

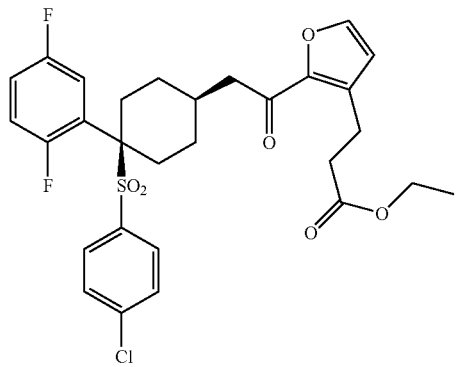

Rhodium on carbon catalyst (15 mg) was added to a solution of the product from Example 145 (100 mg, 0.17 mmol) in methanol (30 mL) and the reaction hydrogenated at 30 psi for 4 hours. The mixture was then filtered through Celite® and evaporated to give an oil. (100 mg). MS (ES+) 579 ([MH]⁺).

Example 147

3-(2-{2-[4-(4-Chloro-benzenesulfonyl)-4-(2,5-difluoro-phenyl)-cyclohexyl]-acetyl}-furan-3-yl)-propionic acid

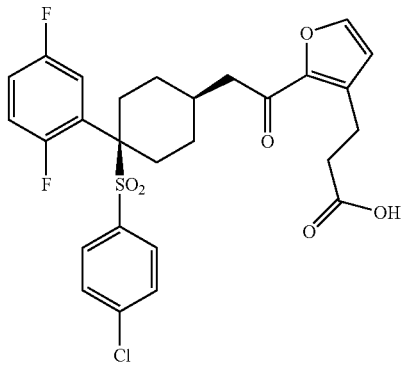

A solution of the product from Example 146 (100 mg, 0.17 mmol) in tetrahydrofuran (2 mL) was treated with a solution of lithium hydroxide (80 mg, 3.3 mmol) in water (2 mL). The reaction was stirred at room temperature for 3 hours, then evaporated and the residue taken up in water and ethyl acetate. The ethyl acetate layer was evaporated and purified by preparative thin layer chromatography (1% acetic acid, 33% ethyl acetate, 33% hexane, 33% dichloromethane).

¹H NMR (400 MHz, CDCl₃) δ 7.57 (1H, s, broad), 7.38–7.32 (4H, m), 7.07–7.01 (2H, m), 6.87–6.79 (1H, m), 6.57–6.49 (1H, m), 3.13–2.91 (3H, m), 2.86–2.26 (6H, m), 2.26–2.00 (2H, m), 1.80–1.67 (2H, m), 1.62–1.49 (2H, m). MS (ES+)=551 ([MH]⁺).

Example 148

3-(5-{2-[4-(4-Chloro-benzenesulfonyl)-4-(2,5-difluoro-phenyl)-cyclohexyl]-acetyl}-furan-2-yl)-propionic acid

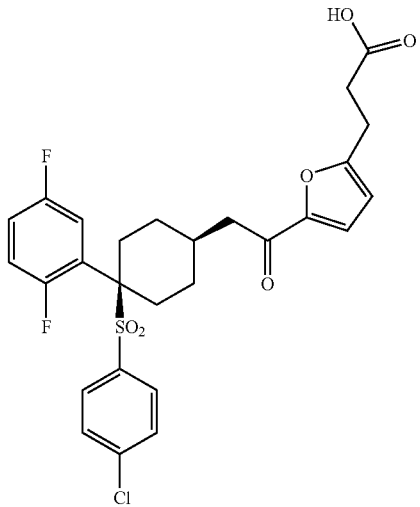

Prepared from the product of Example 141 by the procedures of Examples 146 and 147.

$^1$H NMR (400 MHz, CDCl$_3$) δ 7.49–7.30 (4H, m), 7.15–7.14 (1H, d, J=3.5 Hz), 7.07–7.01 (2H, m), 6.87–6.79 (1H, m), 6.24–6.23 (1H, d, J=3.5 Hz), 3.14–3.11 (1H, t, J=6 Hz), 2.98–2.96 (1H, d, J=7 Hz), 2.78–2.74 (1H, t, J=6 Hz), 2.53–2.27 (7H, m), 1.95–1.68 (3H, m) and 1.60–1.49 (2H, m). MS (ES+) 573 [(MNa]$^+$].

Example 149

2-[4-(4-Chloro-benzenesulfonyl)-4-(2,5-difluoro-phenyl)-cyclohexyl]-1-(3-morpholin-4-ylmethyl-furan-2-yl)-ethanone

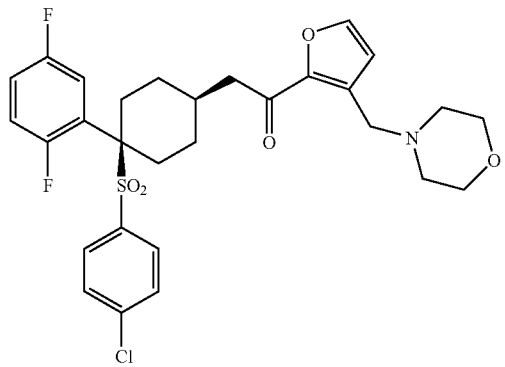

To a stirred solution of the product of Example 143 (100 mg, 0.19 mmol) in methanol (2.5 mL) was added morpholine (100 µL, 1.7 mmol) and sodium cyanoborohydride (9 mg, 0.19 mmol) followed by hydrochloric acid (3M solution in methanol, 0.3 mL) dropwise. The reaction was stirred at room temperature for 20 hours then diluted with diethyl ether and 4N aqueous sodium hydroxide. The organic layer was washed with water, dried (MgSO$_4$) and evaporated to dryness, yielding a yellow oil which was purified by column chromatography on silica eluting with 1:1:1 iso-hexane: dichloromethane:ethyl acetate +1% triethylamine to yield the desired product as a white solid (25 mg).

$^1$H NMR (400 MHz, CDCl$_3$) δ 7.48 (1H, s), 7.37–7.26 (4H, m), 7.07–7.01 (2H, m), 6.87–6.79 (1H, m), 6.66 (1H, s), 3.79 (2H, s), 3.72–3.70 (4H, m), 3.04–3.02 (2H, d, J=8 Hz), 2.79–2.74 (1H, q, J=8 Hz), 2.51–2.32 (8H, m), 1.76–1.71 (2H, m) and 1.58–1.50 (2H, m). MS (ES+) 578 ([MH]$^+$).

Example 150

2-[4-(4-Chloro-benzenesulfonyl)-4-(2,5-difluoro-phenyl)-cyclohexyl]-1-(3-[1, 3]dioxolan-2-yl-phenyl)-ethanone

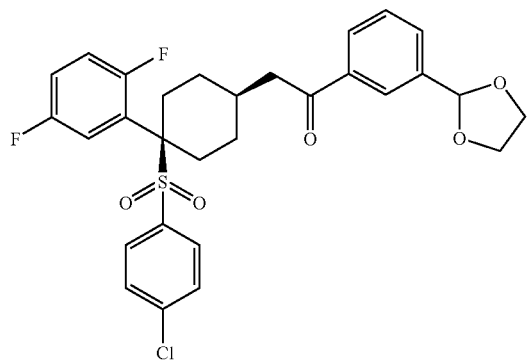

Prepared from 2-(3-bromophenyl)-[1,3]-dioxolane (1.46 g, 6.4 mmol) by the procedure of Example 127. Purification by column chromatography on silica, eluting with diethyl ether:dichloromethane:iso-hexane 1:1:3, afforded the desired compound (85 mg).

$^1$H NMR (CDCl$_3$) δ 8.09 (1H, s), 7.98 (1H, d, J=8.0 Hz), 7.70 (1H, d, J=8.0 Hz), 7.51 (1H, t, J=8.0 Hz), 7.37–7.33 (4H, m), 7.09–7.01 (2H, m), 6.86–6.79 (1H, m), 5.88 (1H, s), 4.21–4.06 (4H, m), 3.14 (2H, d, J=7.0 Hz), 2.48–2.39 (5H, m), 1.81–1.76 (2H, m) and 1.63–1.52 (2H, m). MS (ES+) 583 ([MNa]$^+$).

Example 151

3-{2-[4-(4-Chloro-benzenesulfonyl)-4-(2,5-difluoro-phenyl)-cyclohexyl]-acetyl}-benzaldehyde

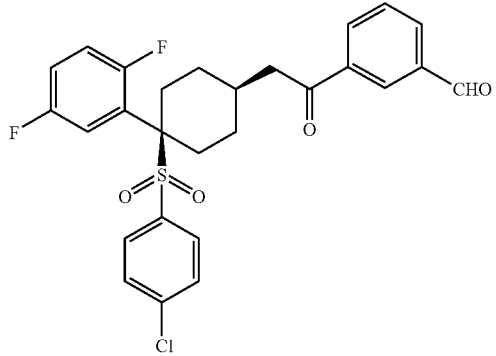

To a stirred solution of the product of Example 150 (73 mg, 0.13 mmol) in acetone (4 mL) and water (1 mL) was added pyridinium p-toluenesulfonate (33 mg, 0.13 mmol) and the mixture refluxed for 3.5 h. The acetone was evaporated and the residue diluted with water (10 mL) and extracted into ethyl acetate (2×10 mL). The combined organic layers were washed with saturated aqueous sodium bicarbonate (10 mL) and brine (20 mL), dried (MgSO$_4$) and evaporated to leave the desired product (64 mg). MS (ES+) 539 ([MNa]$^+$).

Example 152

3-{2-[4-(4-Chloro-benzenesulfonyl)-4-(2,5-difluoro-phenyl)-cyclohexyl]-acetyl}-benzoic acid

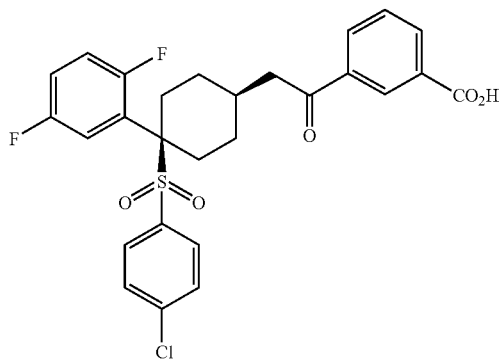

To a stirred solution of the product from Example 151 (58 mg, 0.11 mmol) in dichloromethane (3 mL) and water (3 mL) at 0° C. was added sulfamic acid (44 mg, 0.44 mmol) and sodium chlorite (30 mg, 0.33 mmol). The reaction was allowed to attain room temperature with stirring over 3 hours, the layers separated and the aqueous layer extracted with further dichloromethane (5 mL). The combined organic layers were dried (MgSO$_4$) and evaporated to leave a residue which was filtered through a plug of silica eluting with ether:dichloromethane:iso-hexane 1:1:3, then purified by column chromatography on silica eluting with ethyl acetate: dichloromethane 1:1 +1% acetic acid to afford the desired compound (40 mg).

$^1$H NMR (CDCl$_3$) δ 8.69 (1H, s), 8.33 (1H, d, J=8.0 Hz), 8.23 (1H, d, J=8.0 Hz), 7.63 (1H, t, J=8.0 Hz), 7.38–7.31 (4H, m), 7.10–7.01 (2H, m), 6.87–6.80 (1H, m), 3.19 (2H, d, J=7.0 Hz), 2.55–2.41 (5H, m), 1.84–1.79 (2H, m) and 1.68–1.61 (2H, m). MS (ES+) 555 ([MNa]$^+$).

Example 153

2-{2-[4-(4-Chloro-benzenesulfonyl)-4-(2,5-difluoro-phenyl)-cyclohexyl]-acetyl}-benzaldehyde

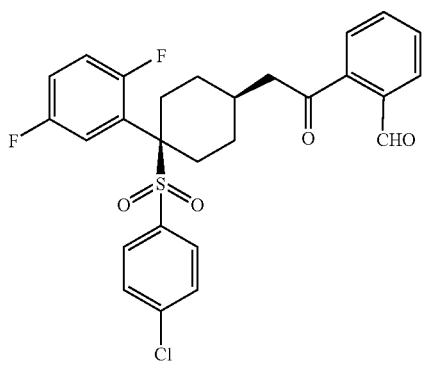

Prepared from 2-(2-bromophenyl)-[1,3]-dioxolane by the procedures of Examples 150 and 151.
MS (ES+) 517 ([MH]$^+$).

Example 154

2-{2-[4-(4-Chloro-benzenesulfonyl)-4-(2,5-difluoro-phenyl)-cyclohexyl]-acetyl}-benzoic acid

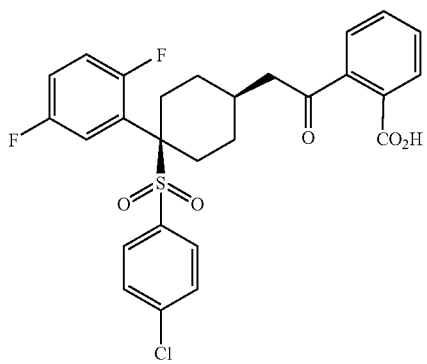

Prepared from the product of Example 153 by the procedure of Example 152. MS (ES+) 555 ([MNa]$^+$).

Example 155

N-[4-(4-Chloro-benzenesulfonyl)-4-(2,5-difluoro-phenyl)-cyclohexylmethyl]acetamide

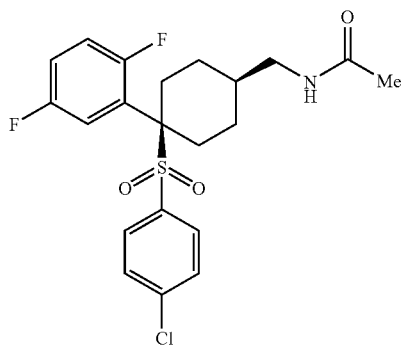

To a stirred solution of Intermediate J (69 mg, 0.17 mmol) in dichloromethane (10 mL) under nitrogen was added acetic anhydride (33 μL, 0.35 mmol), triethylamine (48 μL, 0.35 mmol) and a catalytic amount of dimethylaminopyridine. The reaction mixture was stirred at ambient temperature for 3 h, diluted with dichloromethane, washed with 2N aqueous hydrochloric acid and 1N aqueous sodium hydroxide, dried (MgSO$_4$) and evaporated to give a residue (75 mg) which was purified by preparative thin layer chromatography eluting with 5% methanol:dichloromethane to afford the desired product (48 mg).

$^1$H NMR (CDCl$_3$) δ 7.38–7.32 (4H, m), 7.08–7.01 (2H, m), 6.87–6.81 (1H, m), 5.51 (1H, br, s), 3.35 (2H, t, J=6.6 Hz), 2.45–2.42 (4H, m), 1.99 (3H, s), 1.78–1.75 (3H, m) and 1.52–1.45 (2H, m). MS (ES+) 442 ([MH]$^+$).

Example 156

N-[4-(4-Chloro-benzenesulfonyl)-4-(2,5-difluoro-phenyl)-cyclohexylmethyl]-methanesulfonamide

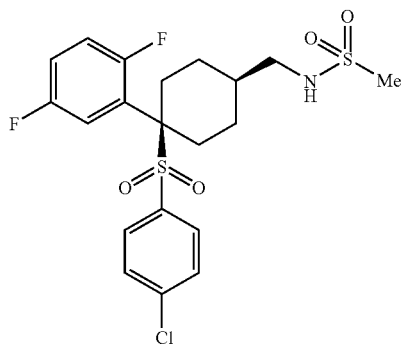

To a stirred solution of Intermediate J (70 mg, 0.18 mmol) and triethylamine (37 μL, 0.26 mmol) in dichloromethane (10 mL) under nitrogen at −30° C. was added mesyl chloride (16 μL, 0.21 mmol). The reaction mixture was stirred for 1 h at −30° C., diluted with water then warmed to ambient temperature and extracted with dichloromethane. The combined organic layers were washed with 10% aqueous citric acid and saturated aqueous sodium hydrogen carbonate, dried (MgSO₄) and evaporated to give a residue (76 mg) which was purified by preparative thin layer chromatography eluting with ethyl acetate:iso-hexane 1:1 to afford the desired product (36 mg).

¹H NMR (CDCl₃) δ 7.35–7.32 (4H, m), 7.08–7.01 (2H, m), 6.87–6.79 (1H, m), 4.25–4.20 (1H, m), 3.24 (2H, dd, J=6.7, 7.4 Hz), 2.99 (3H, s), 2.43–2.41 (4H, m), 1.90–1.70 (3H, m) and 1.52–1.50 (2H, m).

Example 157

[4-(4-Chloro-benzenesulfonyl)-4-(2,5-difluoro-phenyl)-cyclohexylmethyl]-carbamic acid methyl ester

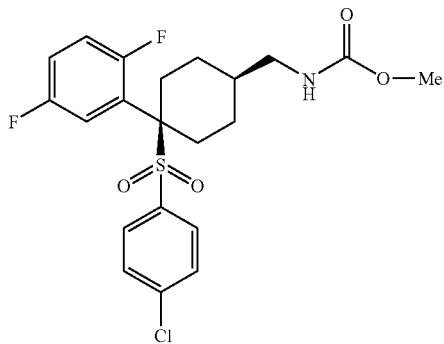

To a stirred solution of Intermediate J (60 mg, 0.15 mmol) and triethylamine (32 µL, 0.23 mmol) in dichloromethane (10 mL) under nitrogen at 0° C. was added methyl chloroformate (14 µL, 0.18 mmol). The reaction mixture was stirred for 3 h at ambient temperature, diluted with water and extracted with dichloromethane. The combined organic layers were washed with 2N aqueous hydrochloric acid, saturated aqueous sodium hydrogencarbonate, dried (MgSO₄) and evaporated to give a residue (100 mg) which was purified by preparative thin layer chromatography eluting with ethyl acetate:iso-hexane 1:4 to afford the desired product (29 mg).

¹H NMR (CDCl₃) δ 7.37–7.31 (4H, m), 7.06–7.04 (2H, m), 6.86–6.80 (1H, m), 4.77 (1H, br s), 3.67 (3H, br s), 3.28 (2H, br s), 2.42 (4H, m), 1.79–1.75 (3H, m) and 1.49–1.48 (2H, m). MS (ES+) 458 ([MH]⁺), 282 ([M-ArSO₂⁻]⁺).

Example 158

N-[4-(4-Chloro-benzenesulfonyl)-4-(2,5-difluoro-phenyl)-cyclohexylmethyl]-C,C,C-trifluoro-methanesulfonamide

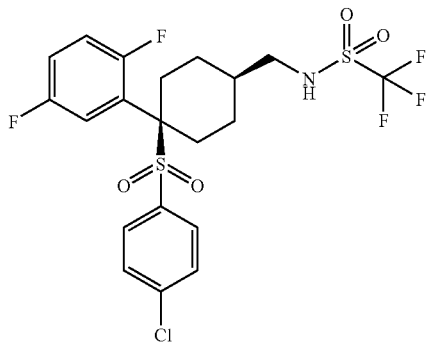

To a stirred solution of Intermediate J (60 mg, 0.15 mmol) and triethylamine (37 µL, 0.26 mmol) in dichloromethane (10 mL) at −70° C. under nitrogen was added trifluoromethanesulfonic anhydride (38 µL, 0.23 mmol). The reaction mixture was stirred for 1 h at −70° C., left to warm to ambient temperature and stirred for 5 h, diluted with saturated aqueous ammonium chloride and extracted with dichloromethane. The combined organic layers were washed with brine, dried (MgSO₄) and evaporated to give a residue (100 mg) which was purified by preparative thin layer chromatography eluting with ethyl acetate:iso-hexane 1:6 to afford the desired product (19 mg).

¹H NMR (CDCl₃) δ 7.38–7.30 (4H, m), 7.05–7.04 (2H, m), 6.84 (1H, m), 5.05 (1H, br s), 3.39 (2H, d, J=6.7 Hz), 2.42 (5H, m), 1.87–1.79 (4H, m).

Example 159

Pyrrolidine-1-sulfonic acid [4-(4-chloro-benzenesulfonyl)-4-(2,5-difluoro-phenyl)-cyclohexylmethyl]-amide

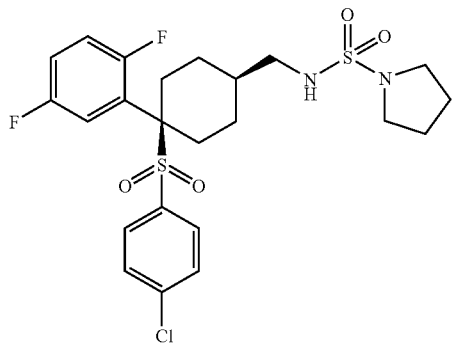

To a stirred solution of Intermediate J (100 mg, 0.25 mmol) in dry tetrahydrofuran (5 mL) under nitrogen at 0° C. was added catechol sulphate (52 mg, 0.30 mmol). The reaction mixture was stirred and allowed to warm to room temperature for 18 h, then diluted with ethyl acetate, washed with saturated aqueous ammonium chloride and brine, dried (MgSO₄) and evaporated to give a residue (130 mg) which was purified by preparative thin layer chromatography eluting with ethyl acetate:iso-hexane 1:3 to afford [4-(4-chlorobenzenesulfonyl)-4-(2,5-difluoro-phenyl)-cyclohexyl]-sulfamic acid 2-hydroxy-phenyl ester (44 mg). To a stirred solution of the sulfamate from the foregoing step (44 mg, 0.08 mmol) under nitrogen in dioxane (1 mL) was added pyrrolidine (23 µL, 0.28 mmol). The reaction mixture was stirred at 80° C. 4 h., cooled to ambient temperature, diluted with water and extracted with dichloromethane. The combined organic layers were washed with 2N aqueous sodium hydroxide and brine, dried (MgSO₄) and evaporated to give a residue (38 mg) which was purified by preparative thin layer chromatography eluting with ethyl acetate:iso-hexane 1:2 to afford the desired product (34 mg).

¹H NMR (CDCl₃) δ 7.38–7.31 (4H, m), 7.08–7.01 (2H, m), 6.87–6.80 (1H, m), 4.41 (1H, t, J=6.3 Hz), 3.33–3.30 (4H, m), 3.15 (2H, t, J=6.8 Hz), 2.45–2.34 (4H, m), 1.98–1.92 (4H, m), 1.87–1.74 (3H, m), 1.56–1.45 (2H, m). MS (ES+) 533 ([MH]⁺).

Example 160

[4-(4-Chloro-benzenesulfonyl)-4-(2,5-difluoro-phenyl)-cyclohexylmethyl]-sulfamic amide

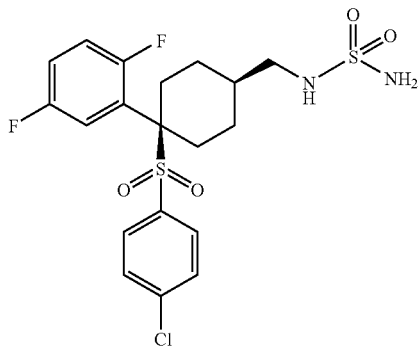

A solution of Intermediate J (36 mg, 0.09 mmol) and sulfamide (43 mg, 0.45 mmol) in dioxane (5 mL) under nitrogen was stirred under reflux for 90 minutes, then cooled to room temperature, diluted with ethyl acetate and washed with water. The combined organic layers were dried (MgSO$_4$) and evaporated to give a residue (18 mg) which was purified by preparative thin layer chromatography eluting with ethyl acetate:iso-hexane 1:2 to afford the desired product (6 mg).

$^1$H NMR (CDCl$_3$) δ 7.37–7.29 (4H, m), 7.07–7.02 (2H, m), 6.86–6.80 (1H, m), 4.77 (2H, s), 4.57 (1H, t, J=6.4 Hz), 3.25 (2H, t, J=7.0 Hz), 2.43 (4H, m), 1.89–1.78 (3H, m) and 1.55–1.49 (2H, m).

Example 161

[4-(4-Chloro-benzenesulfonyl)-4-(2,5-difluoro-phenyl)-cyclohexylmethyl]-sulfamic acid ethyl amide

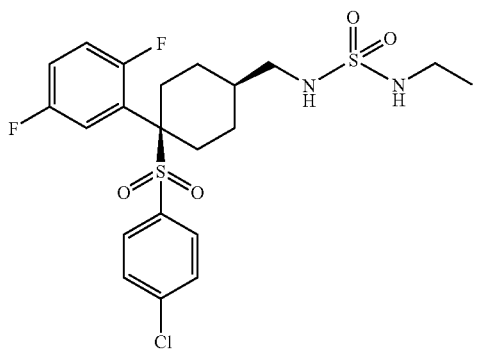

Prepared from Intermediate J using ethylamine by the procedure of Example 159.

$^1$H NMR (MeOD) δ 7.51–7.36 (4H, m), 7.19–7.11 (2H, m), 7.01–6.94 (1H, m), 3.05–2.98 (4H, m), 2.51–2.48 (2H, m), 2.37–2.30 (2H, m), 1.89–1.76 (3H, m), 1.53–1.45 (2H, m) and 1.19 (3H, t, J=7.3 Hz). MS (ES+) 507 ([MH]$^+$), 529 ([MNa]$^+$).

Example 162

1-{[4-(4-Chloro-benzenesulfonyl)-4-(2,5-difluoro-phenyl)-cyclohexvlmethyl]-sulfamoyl}-pyrrolidine-2-carboxylic acid methyl ester

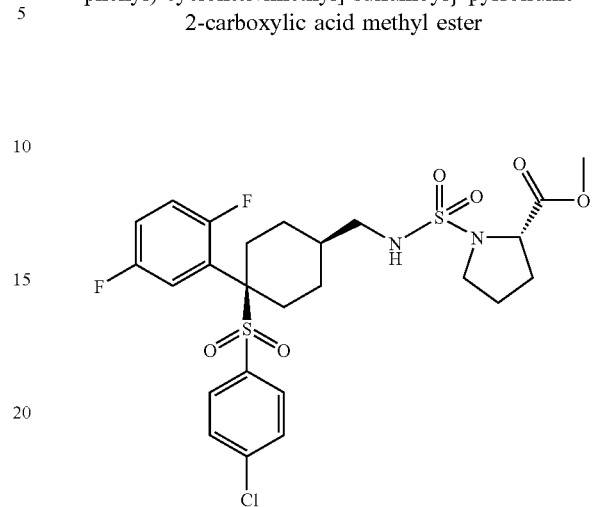

Prepared from Intermediate J using (L)-proline methyl ester by the procedure of Example 159.

$^1$H NMR (CDCl$_3$) δ 7.38–7.31 (4H, m), 7.09–7.00 (2H, m), 6.86–6.80 (1H, m), 4.61 (1H, t, J=6.5 Hz), 4.44 (1H, dd, J=8.8, 4.2 Hz), 3.77 (3H, s), 3.51–3.46 (2H, m), 3.25 (2H, m), 2.42 (4H, m), 2.36–2.28 (1H, m), 2.01–2.00 (3H, m), 1.88–1.77 (3H, m) and 1.50–1.48 (2H, m). MS (ES+) 591 ([MH]$^+$).

Example 163

1-{[4-(4-Chloro-benzenesulfonyl)-4-(2,5-difluoro-phenyl)-cyclohexvlmethyl]-sulfamoyl}-pyrrolidine-2-carboxylic acid

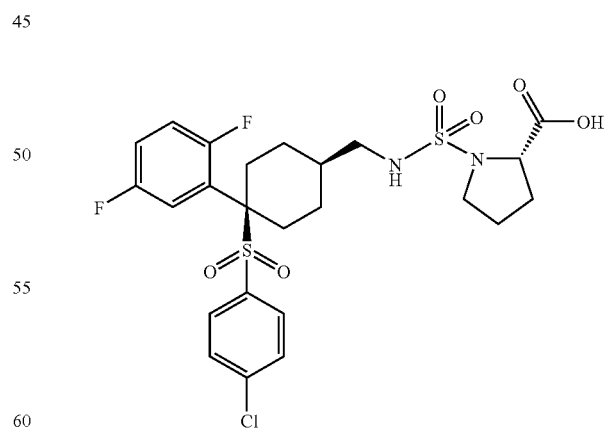

Prepared from the product of Example 162 following the procedure described in Example 130.

MS (ES+) 577 ([MH]$^+$).

Example 164

N-[4-(4-Chloro-benzenesulfonyl)-4-(2,5-difluoro-phenyl)-cyclohexylmethyl]-3,3,3-trifluoro-propionamide

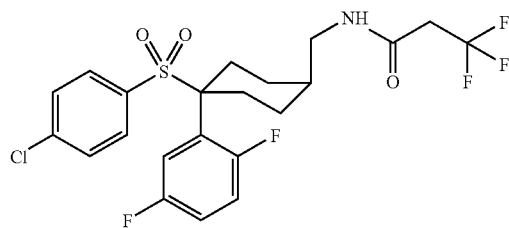

A solution of Intermediate J (84 mg, 0.21 mmol) in N,N-dimethylformamide (2 mL) was treated with 3,3,3-trifluoropropionic acid (30 mg, 0.21 mmol), 1-(3-dimethylaminopropyl)-3-ethylcarbodiimide hydrochloride (60 mg, 0.31 mmol), hydroxybenzotriazole (42 mg, 0.31 mmol) and triethylamine (88 μL, 0.63 mmol) and stirred for 18 hours. The reaction was diluted with water (30 mL) and the product extracted with ethyl acetate (3×20 mL). The combined organic layers were washed with 1N aqueous hydrochloric acid (20 mL), saturated aqueous sodium hydrogencarbonate (20 mL) and brine (20 mL), dried (MgSO$_4$) and evaporated. The product was purified on silica gel chromatography eluting with ethyl acetate/iso-hexane mixtures to give pure product (0.065 g).

$^1$H NMR (360 MHz, CDCl$_3$) δ 7.38–7.30 (4H, m), 7.01–7.06 (2H, m), 6.84–6.81 (1H, m), 5.87 (1H, br s), 3.41 (2H, t, J=6.7 Hz), 3.07 (2H, m), 2.46–2.42 (4H, m), 1.81–1.73 (3H, m) and 1.54–1.47 (2H, m). MS (ES+) 510 ([MH]$^+$).

Example 165

N-[4-(4-Chloro-benzenesulfonyl)-4-(2,5-difluoro-phenyl)-cyclohexvlmethyl]-3,3,3-trifluoro-2-hydroxy-propionamide

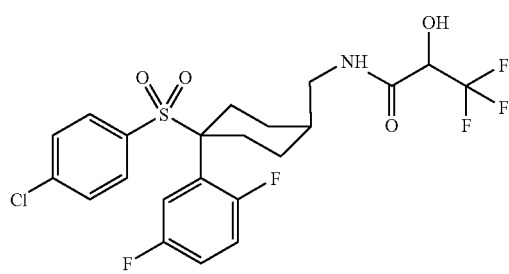

Prepared from Intermediate J by the procedure of Example 164 using 3,3,3-trifluorolactic acid.

$^1$H NMR (360 MHz, CDCl$_3$) δ 7.38–7.31 (4H, m), 7.01–7.06 (2H, m), 6.84–6.81 (1H, m), 6.67 (1H, m), 4.46 (2H, q, J=7.1 Hz), 3.42–3.54 (2H, m), 2.43–2.46 (3H, m), 1.73–1.86 (4H, m) and 1.54–1.45 (2H, m). MS (ES+) 526 ([MH]$^+$).

Example 166

1-[4-(4-Chloro-benzenesulfonyl)-4-(2,5-difluoro-phenyl)-cyclohexylmethyl]-3-methyl-urea

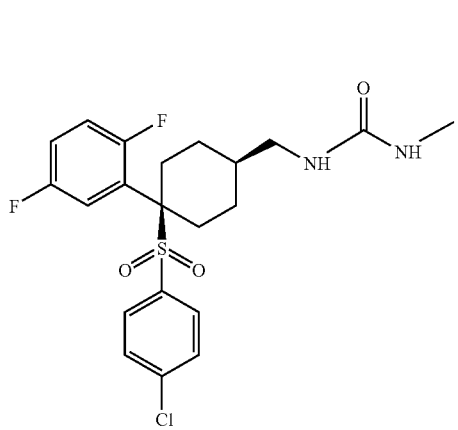

To a stirred solution of Intermediate C (32 mg, 0.08 mmol) in toluene (5 mL) was added triethylamine (0.021 mL, 0.15 mmol) and diphenylphosphoryl azide (0.032 mL, 0.15 mmol) and the resulting solution heated at 110° C. for 3 hours. Upon cooling, methylamine (1 mL of 8M solution in ethanol, 8 mmol) was added and stirring continued for a further 18 hours at ambient temperature. The mixture was diluted with ethyl acetate (10 mL) and water (10 mL) and the layers separated. The organic phase was washed with 2N aqueous hydrochloric acid (10 mL), saturated aqueous sodium hydrogencarbonate (10 mL) and brine (10 mL), dried (MgSO$_4$) and evaporated to leave a residue which was purified by column chromatography on silica eluting with ethyl acetate:iso-hexane 4:1 to afford the desired compound (29 mg).

$^1$H NMR (CDCl$_3$) δ 7.37–7.30 (4H, m), 7.06–7.00 (2H, m), 6.86–6.80 (1H, m), 4.61 (1H, t, J=6.0 Hz), 4.46 (1H, q, J=5.0 Hz), 3.27 (2H, t, J=6.5 Hz), 2.78 (3H, d, J=6.0 Hz), 2.46–2.41 (4H, m), 1.81–1.74 (3H, m) and 1.52–1.44 (2H, m). MS (ES+) 457 ([MH]$^+$).

Example 167

[4-(4-Chloro-benzenesulfonyl)-4-(2,5-difluoro-phenyl)-cyclohexylmethyl]-urea

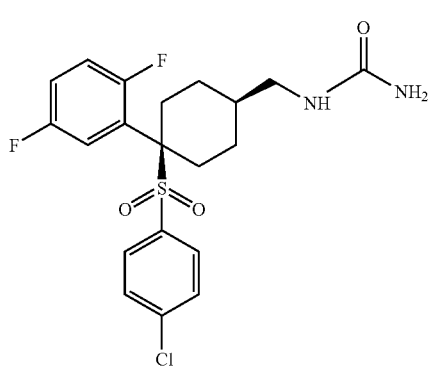

To a stirred solution of Intermediate C (50 mg, 0.12 mmol) in toluene (5 mL) was added triethylamine (0.033 mL, 0.24 mmol) and diphenylphosphoryl azide (0.050 mL, 0.24 mmol) and the resulting solution heated at 110° C. for 3 hours. Upon cooling, ammonia (1 mL of 1M solution in dioxan, 1 mmol) was added and stirring continued for a further 18 hours at ambient temperature. The mixture was diluted with ethyl acetate (10 mL) and water (10 mL) and the layers separated. The organic phase was washed with 2N aqueous hydrochloric acid (10 mL), saturated aqueous sodium hydrogencarbonate (10 mL) and brine (10 mL), dried (MgSO$_4$) and evaporated to leave a residue which was triturated with diethyl ether to afford a solid (21 mg) which was further purified by column chromatography on silica eluting with ethyl acetate:iso-hexane 4:1 to afford the desired compound (5 mg).

$^1$H NMR (CDCl$_3$) δ 7.38–7.31 (4H, m), 7.07–7.01 (2H, m), 6.86–6.80 (1H, m), 4.55 (1H, t, J=6.5 Hz), 4.32 (2H, s), 3.28 (2H, t, J=6.5 Hz), 2.45–2.35 (4H, m), 1.87–1.74 (3H, m) and 1.5–1.4 (2H, m). MS (ES+) 443 ([MH]$^+$).

Example 168

3-[4-(4-Chloro-benzenesulfonyl)-4-(2,5-difluoro-phenyl)-cyclohexylmethyl]-1,1-dimethyl-urea

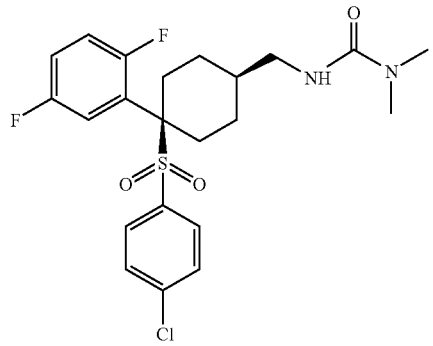

To a stirred solution of Intermediate C (70 mg, 0.16 mmol) in toluene (5 mL) was added triethylamine (0.050 mL, 0.32 mmol) and diphenylphosphoryl azide (0.070 mL, 0.32 mmol) and the resulting solution heated at 110° C. for 3 hours. Upon cooling, dimethylamine (1 mL of 2M solution in methanol, 2 mmol) was added and stirring continued for a further 18 hours at ambient temperature. The mixture was diluted with ethyl acetate (10 mL) and water (10 mL) and the layers separated. The organic phase was washed with 2N aqueous hydrochloric acid (10 mL), saturated aqueous sodium hydrogencarbonate (10 mL) and brine (10 mL), dried (MgSO$_4$) and evaporated to leave a residue which was purified by column chromatography on silica eluting with ethyl acetate:iso-hexane 4:1 to afford the desired compound (47 mg).

$^1$H NMR (CDCl$_3$) δ 7.37–7.31 (4H, m), 7.08–7.01 (2H, m), 6.86–6.79 (1H, m), 4.49 (1H, t, J=6.0 Hz), 3.33 (2H, t, J=6.0 Hz), 2.91 (6H, s), 2.49–2.37 (4H, m), 1.83–1.75 (3H, m) and 1.52–1.41 (2H, m). MS (ES+) 471 ([MH]$^+$).

Example 169

N-[4-(4-Chloro-benzenesulfonyl)-4-(2,5-difluoro-phenyl)-cyclohexylmethyl]-2,2 dimethyl-propionamide

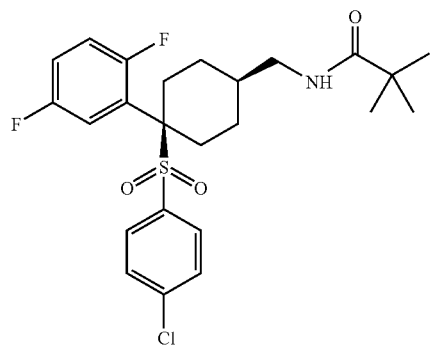

Intermediate J (34 mg, 0.07 mmol.) was dissolved in dichloromethane (5 mL) and triethylamine (0.015 mL, 0.1 mmol), pivaloyl chloride (0.01 mL, 0.09 mmol) and dimethylaminopyridine (1 crystal) added. The solution was stirred at ambient temperature for 2 hours then diluted with further dichloromethane (20 mL) and washed with 2N aqueous hydrochloric acid (2×10 mL) and 1N aqueous sodium hydroxide (10 mL), dried (MgSO$_4$) and evaporated to leave the desired compound (31 mg).

$^1$H NMR (CDCl$_3$) δ 7.37–7.30 (4H, m), 7.07–7.00 (2H, m), 6.86–6.79 (1H, m), 5.72 (1H, t, J=6.5 Hz), 3.28 (2H, t, J=6.5 Hz), 2.52–2.33 (4H, m), 1.80–1.69 (3H, m), 1.65–1.44 (2H, m) and 1.41 (9H, s). MS (ES+) 484 ([MH]$^+$).

Example 170

[4-(4-Chloro-benzenesulfonyl)-4-(2,5-difluoro-phenyl)-cyclohexyl]-sulfamic amide

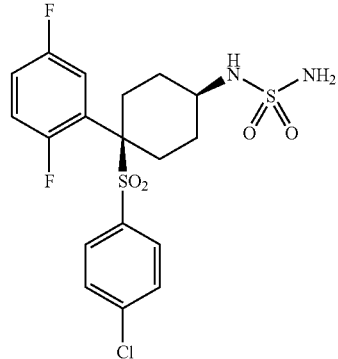

Intermediate R (100 mg, 0.26 mmol in dioxane (4 ml) was treated with sulfamide (125 mg, 1.30 mmol) and heated to reflux for 1 hour, then cooled to room temperature, diluted with ethyl acetate, washed with H$_2$O, dried (MgSO$_4$) and evaporated. Trituration of the residue in ether afforded the desired product (50 mg, 42% yield). $^1$H NMR (360 MHz, CDCl$_3$) δ 7.40–7.30 (4H, m), 7.09–7.02 (2H, m), 6.90–6.80 (1H, m), 5.51–5.46 (1H, m), 5.14–5.07 (2H, broad, s)

3.70–3.61 (1H, m), 2.60–2.49 (3H, m), 2.19–2.10 (2H, m) and 1.99–1.45 (3H, m). m/z=465, 467 [MH]+

Example 171

[4-(4-Chloro-benzenesulfonyl)-4-(2,5-difluoro-phenyl)-cyclohexyl]-sulfamic acid dimethylamide

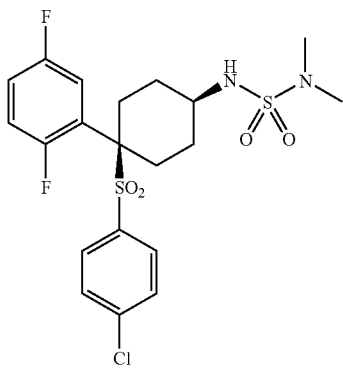

Intermediate R (102 mg, 0.26 mmol) in dichloromethane (3 ml) was treated with N,N dimethylsulfamoyl chloride (112 μL, 0.80 mmol) followed by triethylamine (74 μl, 0.52 mmol) and dimethylacetamide (1 ml). After 2 hours stirring at room temperature the reaction was diluted with ethyl acetate and washed with H₂O and brine, dried (MgSO₄) and evaporated to an oil which crystallised on standing. ¹H NM (360 MHz, CDCl₃) δ 7.39–7.31 (4H, m), 7.09–7.04 (2H, m), 6.89–6.87 (1H, m), 4.56–4.54 (1H, d, J=7.2 Hz), 3.55–3.49 (1H, m), 2.82 (6H, s), 2.61–2.35 (4H, m), 2.06–1.97 (2H, m), 1.57–1.44 (2H, m). m/z=491, 493 [MH]⁻

Examples 172–178 were prepared by the method of Example 171, using the appropriate sulfamoyl chlorides which were prepared by published methods (DE 3429048; FR 2739858; *J. Org. Chem.*, 41, 4029-9, 1976; *J. Heterocyclic Chem.*, 2000, 773) or adaptations thereof.

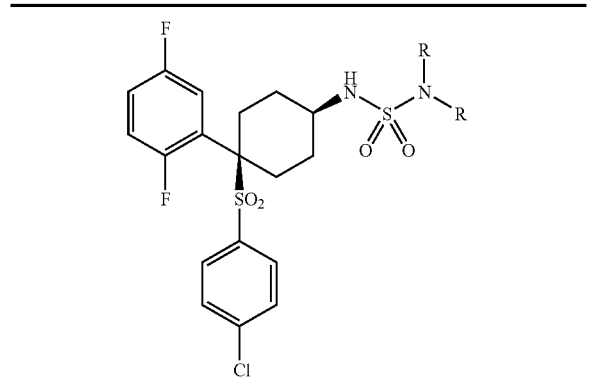

| Example | NR₂ | MS M/Z (ES⁻) |
|---|---|---|
| 172 | NHEt | 491, 493 |
| 173 | NHCH₂CF₃ | 545, 547 |
| 174 | NHᵗBu | 519, 521 |
| 175 | pyrrolidin-1-yl | 517, 519 |
| 176 | azetidin-1-yl | 503, 505 |

-continued

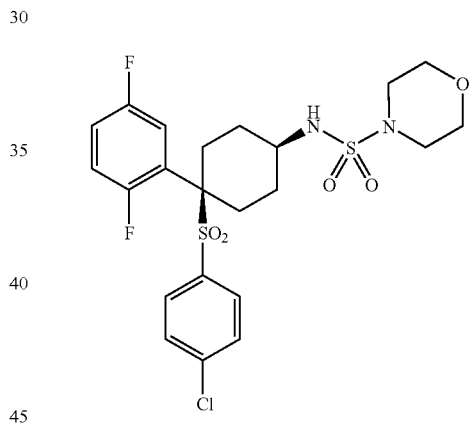

| Example | NR₂ | MS M/Z (ES⁻) |
|---|---|---|
| 177 | 3,3-difluoroazetidin-1-yl | 539, 541 |
| 178 | 4-trifluoromethylpiperidin-1-yl | 599, 601 |

Example 179

Morpholine-4-sulfonic acid [4-(4-chloro-benzenesulfonyl)-4-(2,5-difluoro-phenyl)-cyclohexyl]-amide A solution of morpholine (200 μl, 2.3 mmol) and triethylamine (480 μL, 0.38 mmol) in dichloromethane (1 ml) was added dropwise to a solution of sulfuryl chloride (322 μL, 0.38 mmol) in dichloromethane (2 ml) at 0° C. After 1.25 hours the reaction was diluted with ethyl acetate and H₂O, the organic layer washed with 2N HCl, dried (MgSO₄) and evaporated to an oil which was taken up in acetonitrile (2 ml) and added to a solution of Intermediate R (100 mg, 0.26 mmol) in acetonitrile (2 ml) at room temperature, followed by Hünig's Base (100 μl, 0.52 mmol). Reaction was heated to 80° C. for 6 hours then diluted with ethyl acetate and washed with 2N sodium hydroxide, dried (MgSO₄) and evaporated to a brown oil which was purified by chromatography, eluting with 20% ethyl acetate/hexane to obtain a white solid (38 mg). ¹H NMR (360 MHz, CDCl₃) δ 7.39–7.30 (4H, m), 7.09–7.04 (2H, m) 6.88–6.81 (1H, m), 4.50–4.48 (1H, d, J=6.6 Hz), 3.76–3.74 (4H, m), 3.58–3.56 (1H, m), 3.22–3.20 (4H, m), 2.43–2.35 (4H, m), 2.04–1.99 (2H, m), 1.57–1.50 (2H, m). m/z=533, 535 [MH]⁻

Example 180

(R)-3-(Trimethylacetoxy)pyrrolidine-1-sulfonic acid [4-(4-chloro-benzenesulfonyl)-4-(2,5-difluoro-phenyl)-cyclohexyl]-amide

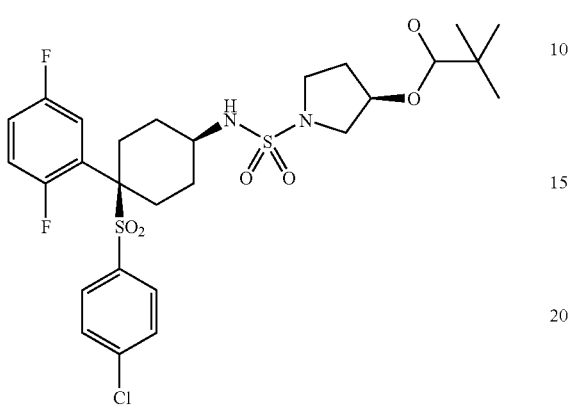

(1) To a solution of (R)-3-pyrrolidinol (2.05 g, 23.5 mmol) in dichloromethane cooled to 0° C. was added triethylamine (16.4 ml, 0.11 mol) followed by benzyl chloroformate (13.44 ml, 94 mmol) dropwise. The reaction was left to stir overnight at room temperature then quenched with 2N HCl. The organic layer was then washed with NaHCO$_3$ solution, dried (MgSO$_4$) and evaporated to an oil which was treated with hexane. The hexane layer was decanted off to leave a viscous oil (5.02 g).

(2) The obtained oil was taken up in dichloromethane (10 ml) and treated with pivaloyl chloride (7 ml, 57 mmol) followed by pyridine (20 ml) and stirred at room temperature for 19 hours. The reaction was then diluted with dichloromethane and washed with 2N HCl, 2N sodium hydroxide, dried (MgSO$_4$) and evaporated to an oil which was purified by chromatography (20% Et$_2$O/hexane) affording the desired intermediate as an oil (1.5 g).

(3) This oil was dissolved in methanol (80 ml) and Pd/C (20 mg) added. The mixture was hydrogenated on a Parr apparatus at 38 psi for 18 hours, filtered through celite then evaporated to a solid (500 mg).

(4) This solid and Et$_3$N (504 μl, 4.3 mmol) in dichloromethane (2 ml) was added dropwise to a solution of sulfuryl chloride (352 μl, 4.3 mmol) at 0° C. After stirring at room temperature for 2 hours the reaction mixture was diluted with ethyl acetate and washed with H$_2$O, dried (MgSO$_4$) and evaporated to an oil (600 mg).

(5) This oil was taken up in acetonitrile (5 ml) and added to a solution of Intermediate R (430 mg) and Hünig's Base (400 μl, 2.7 mmol) in acetonitrile (1 ml). The reaction was heated to 80° C. for 5 hours then diluted with ethyl acetate and washed with 2N HCl, dried (MgSO$_4$) and evaporated to a foam which was purified by chromatography (20% ethyl acetate/hexane) to obtain the desired product as a white solid (495 mg). $^1$H NMR (360 MHz, CDCl$_3$) δ 7.39–7.31 (4H, m), 7.07–7.03 (2H, m) 6.89–6.80 (1H, m), 5.28–5.27 (1H, m), 4.64 (1H, d, J=6.5 Hz), 3.58–3.34 (5H, m), 2.62–2.48 (4H, m), 2.26–2.13 (1H, m), 2.09–1.97 (3H, m), 1.57–1.43 (2H, m) 1.19 (9H, s). m/z=619, 621 [MH]$^+$

Example 181

(R)-3-Hydroxypyrrolidine-1-sulfonic acid [4-(4-chloro-benzenesulfonyl)-4-(2,5-difluoro-phenyl)-cyclohexyl]-amide

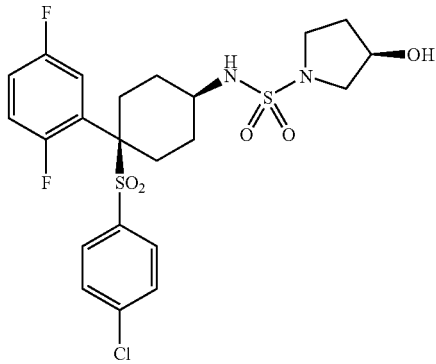

The product from Example 180 (480 mg, 0.77 mmol) in toluene (30 ml) and dichloromethane (25 ml) was treated with DIBAL-H (1M solution in toluene, 3.5 ml) at room temperature and stirred for 19 hours. The reaction was quenched with methanol (2 ml) and stirred for 15 minutes with Na$_2$SO$_4$.10H$_2$O (4 g), then filtered through celite and evaporated to an oil. The oil was diluted with ethyl acetate and washed with 2N HCl, dried (MgSO$_4$) and evaporated. The product was purified by chromatography (40% ethyl acetate/hexane) to afford the desired product as a white solid (110 mg). $^1$H NMR (360 MHz, CDCl$_3$) δ 7.39–7.31 (4H, m), 7.08–7.03 (2H, m) 6.89–6.80 (1H, m), 5.00–4.98 (1H, d, J=7 Hz), 4.53 (1H, s, broad), 3.58–3.44 (5H, m), 2.62–2.37 (4H, m), 2.26–2.06 (5H, m), 1.57–1.43 (2H, m). m/z (ES–)=533, 535

Example 182

3-Oxo-pyrrolidine-1-sulfonic acid [4-(4-chloro-benzenesulfonyl)-4-(2,5-difluoro-phenyl)-cyclohexyl]-amide

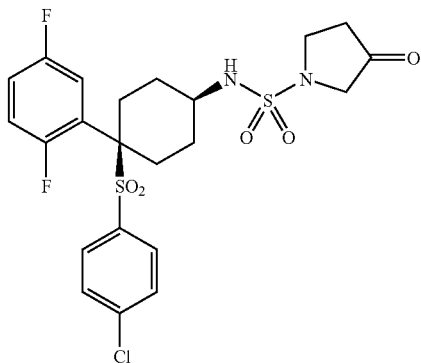

The product from Example 181 (89 mg, 0.17 mmol) in dichloromethane (5 ml) was treated with Dess Martin periodinane (212 mg, 0.5 mmol) and stirred at room temperature for 2 hours. The resulting mixture was filtered through celite and evaporated to an oil which was purified by chromatography (50% ethyl acetate/hexane) to yield a white solid (69 mg). $^{1}$H NMR (360 MHz, CDCl$_{3}$) δ 7.39–7.29 (4H, m), 7.08–7.04 (2H, m) 6.88–6.82 (1H, m), 5.00 (1H, d, J=6.8 Hz), 3.70–3.60 (5H, m), 2.65–2.56 (4H, m), 2.46–2.38 (2H, m), 2.04–2.00 (2H, m), 1.58–1.50 (2H, m). m/z=533, 535 [MH]+

Example 183

3-Hydroxy-3-methylpyrrolidine-1-sulfonic acid [4-(4-chloro-benzenesulfonyl)-4-(2,5-difluoro-phenyl)-cyclohexyl]-amide

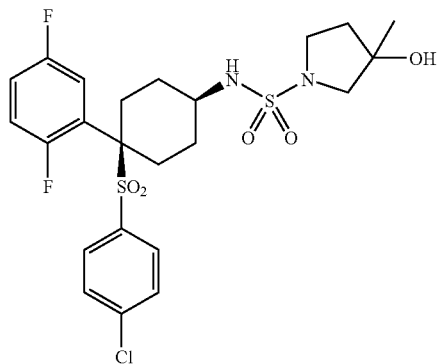

The product from Example 182 (65 mg, 0.12 mmol) in tetrahydrofuran (10 ml) at 0° C. was treated with methyl magnesium bromide (3M solution in tetrahydrofuran, 0.4 ml). The reaction was stirred at 0° C. for 45 minutes then quenched with NH$_{4}$Cl solution, extracted into ethyl acetate and evaporated. The residue was purified by chromatography on silica (diethyl ether) to afford the desired compound (18 mg). $^{1}$H NMR (360 MHz, CDCl$_{3}$) δ 7.38–7.31 (4H, m), 7.07–7.06 (2H, m) 6.89–6.80 (1H, m), 4.90–4.98 (1H, d, J=4 Hz), 3.58–3.55 (2H, m), 3.49–3.40 (2H, m), 3.24–3.23 (1H, m), 2.56–2.39 (4H, m), 2.12 (1H, s), 2.04–1.94 (4H, m), 1.52–1.46 (2H, m), 1.45 (3H, s). m/z=571, 573 [MNa]+

Example 184

3-Hydroxy-azetidine-1-sulfonic acid [4-(4-chloro-benzenesulfonyl)-4-(2,5-difluoro-phenyl)-cyclohexyl]-amide

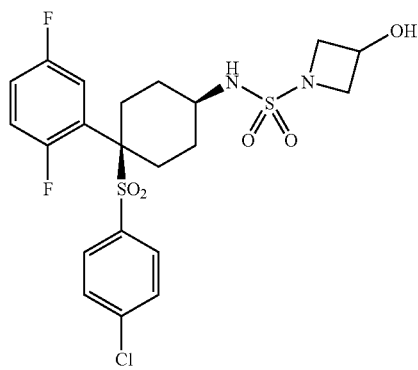

Prepared by the procedures of Example 180 (steps 2–5) and Example 181, starting with 1-benzhydryl-3-hydroxyazetidine (950 mg, 4 mmol). Purification by chromatography (20% ethyl acetate/lexane) afforded the desired product as a white solid (35 mg). $^{1}$H NMR (360 MHz, CDCl$_{3}$) δ 7.39–7.29 (4H, m), 7.07–7.04 (2H, m) 6.85–6.83 (1H, m), 5.44–5.42 (1H, d, J=7 Hz), 4.55–4.53 (1H, m), 4.05–4.01 (2H, t, J=7), 3.91–3.87 (2H, t, J=7), 3.60–3.58 (1H, m), 2.96–2.94 (1H, d, J=10), 2.56–2.47 (4H, m), 2.04–2.01 (2H, m), 1.58–1.48 (2H, m). m/z=521, 523 [MH]+

Example 185

3-Oxo-azetidine-1-sulfonic acid [4-(4-chloro-benzenesulfonyl)-4-(2,5-difluoro-phenyl)-cyclohexyl]-amide

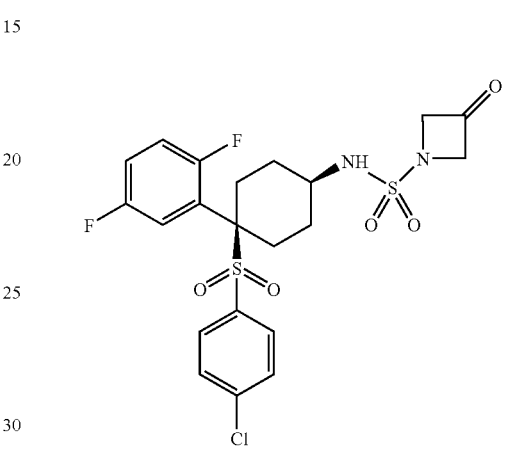

Prepared from the product from Example 184 (420 mg, 0.81 mmol.) by the procedure of Example 182. Purified by column chromatography on silica, eluting with ethyl acetate:dichloromethane:iso-hexane (1:1:2), to afford the desired product $^{1}$H NMR (CDCl$_{3}$) δ 7.38 (2H, d, J=8.6 Hz), 7.31 (2H, d, J=8.6 Hz), 7.11–7.05 (2H, m), 6.88–6.80 (1H, m), 4.90 (1H, d, J=6 Hz), 4.74 (4H, s), 3.68 (1H, m), 2.65–2.50 (2H, m), 2.45–2.35 (2H, m), 2.1–2.0 (2H, m) and 1.6–1.5 (2H, m).

Example 186

3-Hydroxy-3-methyl-azetidine-1-sulfonic acid [4-(4-chloro-benzenesulfonyl)-4-(2,5-difluoro-phenyl)-cyclohexyl]-amide

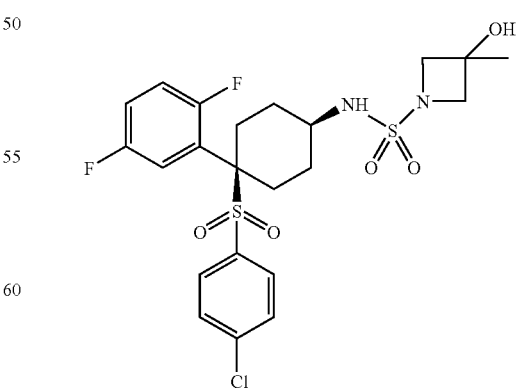

Prepared from the product from Example 185 (88 mg, 0.17 mmol.) by the procedure of Example 183 Purified by column chromatography on silica, eluting with ethyl acetate:dichloromethane:iso-hexane (1:1:1), to afford the desired product (71 mg). $^1$H NMR (CDCl$_3$) δ 7.37 (2H, d, J=8.6 Hz), 7.30 (2H, d, J=8.6 Hz), 7.08–7.04 (2H, m), 6.88–6.81 (1H, m), 5.80 (1H, d, J=6.7 Hz), 3.99 (2H, d, J=8.2 Hz), 3.67 (2H, d, J=8.2 Hz), 3.61 (1H, m), 3.41 (1H, s), 2.7–2.44 (4H, m), 2.06–1.98 (2H, m), 1.55 (3H, s) and 1.5–1.4 (2H, m). MS (ES+) 535 ([MH]$^+$).

Example 187

3-Dimethylamino-azetidine-1-sulfonic acid [4-(4-chloro-benzenesulfonyl)-4-(2,5-difluoro-phenyl)-cyclohexyl]-amide

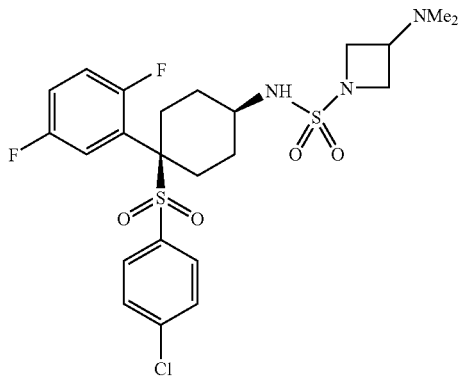

To a stirred solution of the product from Example 185 (74 mg, 0.14 mmol.) in methanol (5 ml) was added dimethylamine hydrochloride (58 mg, 0.7 mmol.). The mixture was stirred 5 minutes, sodium cyanoborohydride (27 mg, 0.42 mmol.) and sodium acetate (34 mg, 0.4 mmol.) added, and the mixture stirred a further 18 hours at ambient temperature. Ethyl acetate (20 ml) was added and the mixture washed with 1N sodium hydroxide and brine, dried (MgSO$_4$) and evaporated to leave a residue which was purified by column chromatography on silica, eluting with ethyl acetate to afford the desired product (21 mg). $^1$H NMR (CDCl$_3$) δ 7.37 (2H, d, J=8.6 Hz), 7.32 (2H, d, J=8.6 Hz), 7.09–7.04 (2H, m), 6.88–6.81 (1H, m), 4.49 (1H, d, J=6.4 Hz), 3.87–3.78 (4H, m), 3.59 (1H, m), 3.08 (1H, m), 2.6–2.5 (2H, m), 2.41–2.33 (2H, m), 2.17 (6H, s), 2.05–2.00 (2H, m) and 1.53–1.41 (2H, m). MS (ES+) 548 ([MH]$^+$).

Example 188

Pyrrolidine-1-sulfonic acid [4-(2,5-difluoro-phenyl)-4-(4-trifluoromethyl-benzenesulfonyl)-cyclohexyl]-amide

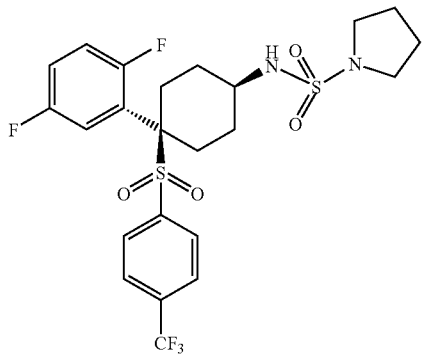

Sulfuryl chloride (236 µl, 2.9 mmol) in toluene (2 ml) was cooled to −30° C. and pyrrolidine (242 µl, 29 mmol) added dropwise over 10 min. The reaction was stirred for 1.5 h at −30° C., diluted with toluene, washed with water, aqueous HCl (2 M) and brine, dried (MgSO$_4$), filtered and evaporated to give an oil. This was dissolved in dichloromethane (1 ml) and added to a solution of Intermediate S (120 mg, 0.29 mmol) in dichloromethane (2 ml) at 0° C. and the reaction allowed to warm to room temperature and stirred for 18 h. The mixture was diluted with dichloromethane, washed with water, brine, dried (MgSO$_4$) filtered and evaporated. The residue was purified by flash chromatography eluting with iso-hexane/ethyl acetate (1:1) to give a white solid (62 mg). $^1$H NMR δ (ppm) (CDCl$_3$): 1.48–1.52 (3H, m), 1.89–2.02 (5H, m), 2.39–2.62 (4H, m), 3.31 (4H, m), 3.57 (1H, q, J=2.7 Hz), 4.42 (1H, d, J=6.3 Hz), 6.79–6.86 (1H, m), 7.05–7.10 (2H, m), 7.53 (2H, d, J=7.8 Hz), 7.66 (2H, d, J=7.8 Hz). MS [MH$^+$] 553

Example 189

Pyrrolidine-1-sulfonic acid [4-(2,5-difluoro-phenyl)-4-(6-trifluoromethyl-pyridyl-3-sulfonyl)-cyclohexyl]-amide

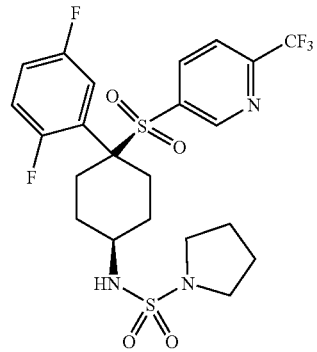

Prepared by the procedure described for Example 188, using Intermediate T.

m/z=554 (MH$^+$)

The invention claimed is:

1. A compound of formula I:

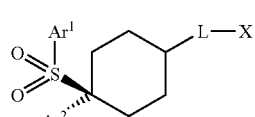

wherein

X represents SCN, SR$^1$, S(O)R$^1$, (CR$^a$R$^b$)$_m$SO$_2$R$^1$, SO$_2$N(R$^2$)$_2$, SO$_2$NHCOR$^1$, SO$_2$NHN(R$^2$)$_2$, OSO$_2$N(R$^2$)$_2$, OS(O)N(R$^2$)$_2$, OSO$_2$NHCOR$^1$, COR$^4$, NHCOR$^1$, NHCO$_2$R$^1$, NHCON(R$^2$)$_2$, NHSO$_2$R$^1$ or NHSO$_2$N(R$^2$)$_2$;

m is 0 or 1

R$^a$ represents H or C$_{1-4}$alkyl;

R$^b$ represents H, C$_{1-4}$alkyl, CO$_2$H, C$_{1-4}$alkoxycarbonyl or C$_{1-4}$alkylsulphonyl; or R$^b$ may combine with R$^1$ to form a 5- or 6-membered ring;

L represents a bond, =CH— or —(CHR$^a$)$_n$—; with the proviso that L does not represent a bond when X represents NHCOR$^1$, NHCO$_2$R$^1$ or NHSO$_2$R$^1$; and with the proviso that if L represents =CH—, X represents SO$_2$R$^1$ or COR$^4$;

n is 1, 2 or 3;

R$^1$ represents CF$_3$ or C$_{1-6}$alkyl, C$_{2-6}$alkenyl, C$_{3-9}$cycloalkyl or C$_{3-6}$cycloalkylC$_{1-6}$alkyl, any of which may bear up to 2 substituents selected from halogen, CN, CF$_3$, OR$^3$, COR$^3$, CO$_2$R$^3$, OCOR$^{3a}$, SO$_2$R$^{3a}$, N(R$^5$)$_2$, and CON(R$^5$)$_2$, or R$^1$ represents aryl, arylC$_{1-6}$alkyl, C-heterocyclyl or C-heterocyclylC$_{1-6}$alkyl;

or R$^1$ may combine with R$^b$ to form a 5- or 6-membered ring;

each R$^2$ independently represents H, C$_{1-6}$alkoxy, or C$_{1-6}$alkyl, C$_{2-6}$alkenyl, C$_{3-9}$cycloalkyl or C$_{3-6}$cycloalkylC$_{1-6}$alkyl, any of which may bear up to 2 substituents selected from halogen, CN, CF$_3$, OR$^3$, COR$^3$, CO$_2$R$^3$, OCOR$^{3a}$, and CON(R$^5$)$_2$; or aryl, arylC$_{1-6}$alkyl, C-heterocyclyl or C-heterocyclylC$_{1-6}$alkyl;

or two R$^2$ groups together with a nitrogen atom to which they are mutually attached complete an N-heterocyclyl group;

R$^3$ represents H, C$_{1-4}$alkyl, phenyl or heteroaryl;

R$^{3a}$ represents C$_{1-4}$alkyl, phenyl or heteroaryl;

R$^4$ represents (CR$^a$R$^b$)SO$_2$R$^1$, pyridine N-oxide, or phenyl or heteroaryl which bear a substituent selected from CO$_2$H, methylenedioxy, difluoromethylenedioxy, COR$^3$, C-heterocyclyl, C$_{1-4}$alkylsulphonyl and substituted C$_{1-6}$alkyl, C$_{1-6}$alkoxy, C$_{2-6}$alkenyl or C$_{2-6}$alkenyloxy wherein the substituent is selected from halogen, CN, CF$_3$, OR$^3$, CO$_2$R$^3$, OCOR$^{3a}$, N(R$^5$)$_2$ and CON(R$^5$)$_2$;

R$^5$ represents H or C$_{1-4}$alkyl, or two R$^5$ groups together with a nitrogen atom to which they are mutually attached complete an azetidine, pyrrolidine, piperidine, morpholine, thiomorpholine or thiomorpholine-1,1-dioxide ring;

Ar$^1$ and Ar$^2$ independently represent phenyl or heteroaryl, either of which bears 0–3 substituents independently selected from halogen, CN, NO$_2$, CF$_3$, CHF$_2$, OH, OCF$_3$, CHO, CH=NOH, C$_{1-4}$alkoxy, C$_{1-4}$alkoxycarbonyl, C$_{2-6}$acyl, C$_{2-6}$alkenyl and C$_{1-4}$alkyl which optionally bears a substituent selected from halogen, CN, NO$_2$, CF$_3$, OH and C$_{1-4}$alkoxy;

aryl at every occurrence thereof refers to phenyl or heteroaryl which optionally bear up to 3 substituents selected from halogen, CN, NO$_2$, CF$_3$, OCF$_3$, OR$^3$, COR$^3$, CO$_2$R$^3$, OCOR$^{3a}$, N(R$^5$)$_2$, CON(R$^5$)$_2$ and optionally-substituted C$_{1-6}$alkyl, C$_{1-6}$alkoxy, C$_{2-6}$alkenyl or C$_{2-6}$alkenyloxy wherein the substituent is selected from halogen, CN, CF$_3$, phenyl, OR$^3$, CO$_2$R$^3$, OCOR$^{3a}$, N(R$^5$)$_2$ and CON(R$^5$)$_2$; and C-heterocyclyl and N-heterocyclyl at every occurrence thereof refer respectively to a heterocyclic ring system bonded through carbon or nitrogen, said ring system being non-aromatic and comprising up to 10 atoms, at least one of which is O, N or S, and optionally bearing up to 3 substituents selected from oxo, halogen, CN, NO$_2$, CF$_3$, OCF$_3$, OR$^3$, COR$^3$, CO$_2$R$^3$, OCOR$^{3a}$, OSO$_2$R$^{3a}$, N(R$^5$)$_2$, CON(R$^5$)$_2$ and optionally-substituted phenyl, C$_{1-6}$alkyl, C$_{1-6}$alkoxy, C$_{2-6}$alkenyl or C$_{2-6}$alkenyloxy wherein the substituent is selected from halogen, CN, CF$_3$, OR$^3$, CO$_2$R$^3$, OCOR$^{3a}$, N(R$^5$)$_2$ and CON(R$^5$)$_2$;

or a pharmaceutically acceptable salt thereof.

2. A compound according to claim 1 wherein X is selected from SR$^1$, (CR$^a$R$^b$)$_m$SO$_2$R$^1$, SO$_2$N(R$^2$)$_2$, OSO$^2$N(R$^2$)$_2$, COR$^4$, NHCOR$^1$, NHCO$_2$R$^1$, NHCON(R$^2$)$_2$, NHSO$_2$R$^1$ and NHSO$_2$N(R$^2$)$_2$; with the proviso that L does not represent a bond when X represents NHCOR$^1$, NHCO$_2$R$^1$ or NHSO$_2$R$^1$.

3. A compound according to claim 1 which is in accordance with formula II:

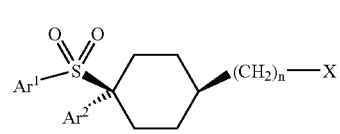

II or a pharmaceutically acceptable salt thereof.

4. A compound according to claim 1 which is in accordance with formula III:

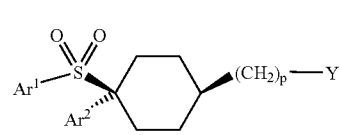

III wherein p is 0, 1, 2 or 3;

Y is SCN, SR$^1$, S(O)R$^1$, (CR$^a$R$^b$)$_m$SO$_2$R$^1$, SO$_2$N(R$^2$)$_2$, SO$_2$NHCOR$^1$, SO$_2$NHN(R$^2$)$_2$, OSO$_2$N(R$^2$)$_2$, OS(O)N(R$^2$)$_2$, OSO$_2$NHCOR$^1$, COR$^4$, NHCON(R$^2$)$_2$ or NHSO$_2$N(R$^2$)$_2$;

and m, R$^a$, R$^b$, R$^1$, R$^2$, R$^4$, Ar$^1$ and Ar$^2$ are as defined in claim 1;

or a pharmaceutically acceptable salt thereof.

5. A compound according to claim 1 which is in accordance with formula IV:

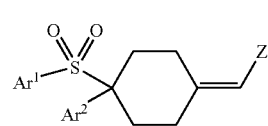

IV wherein Z represents SO$_2$R$^1$ or COR$^4$;

and R$^1$, R$^4$, Ar$^1$ and Ar$^2$ are as defined in claim 1;

or a pharmaceutically acceptable salt thereof.

6. A compound according to claim 1 wherein Ar$^1$ is 4-chlorophenyl or 4-trifluoromethylphenyl or 6-(trifluoromethyl)-3-pyridyl and Ar$^2$ is 2,5difluorophenyl.

7. A pharmaceutical composition comprising a compound according to claim 1 and a pharmaceutically acceptable carrier.

8. A method of treatment of a subject suffering from or prone to a condition associated with the deposition of β-amyloid wherein the condition is Alzheimer's disease, which comprises administering to that subject an effective amount of a compound according to claim 1.

* * * * *